United States Patent
Sierks et al.

(10) Patent No.: US 11,549,113 B2
(45) Date of Patent: Jan. 10, 2023

(54) HUMAN ALZHEIMER'S DISEASE AND TRAUMATIC BRAIN INJURY ASSOCIATED TAU VARIANTS AS BIOMARKERS AND METHODS OF USE THEREOF

(71) Applicant: ARIZONA BOARD OF REGENTS ON BEHALF OF ARIZONA STATE UNIVERSITY, Scottsdale, AZ (US)

(72) Inventors: Michael Sierks, Fort McDowell, AZ (US); Lalitha Venkataraman, Tempe, AZ (US); Wei Xin, Tempe, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 39 days.

(21) Appl. No.: 16/712,652

(22) Filed: Dec. 12, 2019

(65) Prior Publication Data
US 2021/0032634 A1 Feb. 4, 2021

Related U.S. Application Data

(63) Continuation of application No. 16/400,894, filed on May 1, 2019, now abandoned, which is a continuation of application No. 16/060,880, filed as application No. PCT/US2016/065908 on Dec. 9, 2016, now abandoned.

(60) Provisional application No. 62/266,461, filed on Dec. 11, 2015.

(51) Int. Cl.
| | | |
|---|---|---|
| *C12N 15/62* | (2006.01) |
| *C07K 16/18* | (2006.01) |
| *A61P 25/28* | (2006.01) |
| *C07K 1/22* | (2006.01) |
| *G01N 33/68* | (2006.01) |

(52) U.S. Cl.
CPC .............. *C12N 15/62* (2013.01); *A61P 25/28* (2018.01); *C07K 1/22* (2013.01); *C07K 16/18* (2013.01); *G01N 33/6896* (2013.01); *G01N 2800/2821* (2013.01)

(58) Field of Classification Search
None
See application file for complete search history.

(56) References Cited

U.S. PATENT DOCUMENTS

2022/0281943 A1* 9/2022 Bluestone ............ C12N 5/0637

FOREIGN PATENT DOCUMENTS

CN 104926940 * 6/2015

OTHER PUBLICATIONS

Kenkel "What is an ScFv?" accessed from blog.addgene.org on Feb. 24, 2022 (Year: 2021).*
Wikipedia "Single-domain antibody" accessed from wikipedia.org on Feb. 24, 2022 (Year: 2022).*
Google.com—machine translation of CN 104926940—accessed on Feb. 24, 22 (Year: 2015).*
Kussie "A Single Engineered Amino Acid Substitution Changes Antibody Fine Specificity" J immunol 152(1):146-52 (Year: 1994).*
Muyldermans "a guide to: generation and design of nanobodies" FEBS 288:2084-2102 (Year: 2021).*

* cited by examiner

*Primary Examiner* — Adam Weidner
(74) *Attorney, Agent, or Firm* — Duane Morris LLP

(57) ABSTRACT

The present invention provides detection reagents and method for determining risk of traumatic brain injury (TBI) and/or susceptibility to neurodegenerative disease in a subject.

11 Claims, 7 Drawing Sheets

Specification includes a Sequence Listing.

Phosphorylated tau AT8

Binding to BSA (round 1) at 20μm   Binding to BSA (round 34) at 20μm

Binding to aggregated α-syn (round 1) at 20μm   Binding to aggregated α-syn (round 12) at 20μm Binding to AD Braak I tissue
(round 1) at 5μm Binding to Braak I tissue
(round 15) at 5μm Binding to AD Braak I tau IP
(round 1) at 5μm Binding to Braak I tau IP
(round 8) at 5μm

HUMAN ALZHEIMER'S DISEASE AND TRAUMATIC BRAIN INJURY ASSOCIATED TAU VARIANTS AS BIOMARKERS AND METHODS OF USE THEREOF

CROSS-REFERENCE TO RELATED APPLICATIONS

This application is a continuation application of U.S. application Ser. No. 16/400,894 filed May 1, 2019, which is a continuation application of U.S. application Ser. No. 16/060,880, filed on Jun. 8, 2018, now abandoned, which is a 35 U.S.C. § 371 application of International Application No. PCT/US2016/065908, filed on Dec. 9, 2016, which claims the benefit of U.S. Provisional Application Ser. No. 62/266,461, filed on Dec. 11, 2015. The entire content of the applications referenced above are hereby incorporated by reference herein.

STATEMENT REGARDING FEDERALLY SPONSORED RESEARCH

This invention was made with government support under W81XWH-14-1-0467 awarded by the Department of Defense and R21 AG041472 awarded by the National Institutes of Health. The government has certain rights in the invention.

SEQUENCE LISTING

The instant application contains a Sequence Listing that has been submitted electronically in ASCII format and is hereby incorporated by reference in its entirety. Said ASCII copy, created on Feb. 10, 2017, is named 17555 036WO1 SL.TXT and is 139,742 bytes in size.

BACKGROUND

Numerous studies have implicated small soluble oligomeric aggregates of Aβ as toxic species in Alzheimer's disease (AD), and increasing evidence also implicates oligomeric forms of tau as having a direct role in disease pathogenesis of AD and other tauopathies such as Frontotemporal Dementia (FTD). As the focus of Aβ studies has slowly shifted toward soluble Aβ species and mechanisms, new reagents were needed that could specifically identify the variety of different aggregate species present. Indeed, many contradictory studies on the role of Aβ aggregation in AD were reported and progress impeded because suitably selective reagents were not available to characterize the aggregate species present. Increasing evidence from cell and animal models indicate that oligomeric rather than fibrillar forms of tau are toxic and correlate with neuronal degeneration, therefore well characterized reagents that can specifically recognize the diversity of tau morphologies present in the human brain are critically needed to facilitate studies to identify the most promising tau species for use as biomarkers of disease and to study toxic mechanisms.

The microtubule associating protein tau is a major component of the neurofibrillary tangles associated with AD and tauopathies that are characterized by hyperphosphorylation and aggregation of tau. Tau plays an important role in assembly and stabilization of microtubules. Tau is a natively unfolded protein, and similar to a number of other natively unfolded proteins, it can aberrantly fold into various aggregate morphologies including β-sheet rich fibrillar forms. The different types of post-translational modifications of tau in AD include phosphorylation, glycosylation, glycation, prolyl-isomerization, cleavage or truncation, nitration, polyamination, ubiquitination, sumoylation, oxidation and aggregation. Tau has 85 putative phosphorylation sites, and excess phosphorylation can interfere with microtubule assembly. Tau can be modified by phosphorylation or by reactive nitrogen and oxygen species among others. Elevated total tau concentration in CSF has been correlated with AD, as has the presence of various phosphorylated tau forms, and the ratio of tau to Aβ42. Reactive nitrogen and oxygen can modify tau facilitating formation of aggregate forms including oligomeric species. Levels of oligomeric tau have also been implicated as a potential early diagnostic for AD. Therefore, while determination of total tau and phosphorylated tau levels has demonstrated value for diagnosis of AD and other tauopathies, reagents that can selectively recognize the tau species that are most selectively involved in AD would have particular value in diagnostics for neurodegenerative diseases including tauopathies and AD.

Tau is an intrinsically unstructured protein due to its very low hydrophobic content containing a projection domain, a basic proline-rich region, and an assembly domain. Hexapeptide motifs in repeat regions of tau give the protein a propensity to form β-sheet structures which facilitate interaction with tubulin to form microtubules as well as self-interaction to form pathological aggregates such as paired helical filaments (PHF). Hyperphosphorylation of tau, particularly in the assembly domain, decreases the affinity of tau to the microtubules and impairs its ability to regulate microtubule dynamics and axonal transport. In addition, parts of the basic proline-rich domain and the pseudo-repeat also stabilize microtubules by interacting with its negatively charged surface. Alternative splicing of the second, third and tenth exons of tau results in six tau isoforms of varying length in the CNS. The assembly domain in the carboxyl-terminal portion of the protein contains either three or four repeats (3R or 4R) of a conserved tubulin-binding motif depending on alternative splicing of exon 10. Tau 4R isoforms have greater microtubule binding and stabilizing ability than the 3R isoforms. Human adult brains have similar levels of 3R and 4R isoforms, while only 3R tau is expressed at the fetal stage. Mutations altering splicing of tau transcript and the ratio of 3R to 4R tau isoforms are sufficient to cause neurodegenerative disease. Therefore tau in human brain tissue can exist in a variety of different lengths and morphologies and with multiple post-translational modifications.

Tau plays a critical role in the pathogenesis of AD and studies show that reduction of tau levels in AD animal models reverses disease phenotypes and that tau is necessary for the development of cognitive deficits in AD models caused by over-expression of Aβ. While NFTs have been implicated in mediating neurodegeneration in AD and tauopathies, animal models of tauopathy have shown that memory impairment and neuron loss do not associate well with accumulation of NFT. Animal studies showed improvement in memory and reduction in neuron loss despite the accumulation of NFTs, a regional dissociation of neuron loss and NFT pathology, and hippocampal synapse loss and dysfunction and microglial activation months before the accumulation of filamentous tau inclusions. The pathological structures of tau most closely associated with AD progression are tau oligomers. All these studies suggest that tau tangles are not acutely neurotoxic, but rather that pretangle oligomeric tau species are responsible for the neurodegenerative phenotype, similar to toxic role of oligomeric Aβ species.

Numerous studies suggest that extracellular tau species contribute to neurotoxicity through an "infectious" model of disease progression. For example, tau pathology spreads contiguously throughout the brain from early to late stage disease, extracellular tau aggregates can propagate tau misfolding from the outside to the inside of a cell, brain extract from a transgenic mouse with aggregated mutant human tau transmits tau pathology throughout the brain in mice expressing normal human tau, induction of pro-aggregation human tau induces formation of tau aggregates and tangles composed of both human and normal murine tau (co-aggregation), and levels of tau rise in CSF in AD, whereas Aβ levels decrease. A receptor-mediated mechanism for the spread of tau pathology by extracellular tau has been described.

Collectively, these studies all indicate that a variety of different tau forms including splice variants, post-translational modifications and different aggregated forms, both intracellular and extracellular, are vitally important in AD and other tauopathies. In order to more clearly define the role of individual tau forms in disease, there is a critical need to develop a series of well-defined reagents that selectively recognize individual tau species, and to use these reagents to identify which tau forms are the best biomarkers for AD, which forms are involved in toxicity, and which forms can distinguish between healthy and AD patients in brain tissue and CSF samples.

SUMMARY

Methods have been developed that enable generation of reagents that selectively bind disease related protein variants. The inventors have developed methods and reagents to assess neuronal damage following traumatic brain injury (TBI). The inventors have also developed methods and reagents to assess the staging of Alzheimer's Disease (AD). Phage display antibody libraries are used as a source to isolate the protein variant specific reagents.

The present invention discloses an antibody or antibody fragment that preferentially recognizes human traumatic brain injury (TBI)-associated tau and other antibody or antibody fragments that preferentially recognize different stages of AD. As used herein, the phrase "preferentially recognizes" indicates that it does not bind to or recognize non-TBI associated forms of tau or non-specific proteins. As used herein, the term "antibody" includes scFv (also called a "nanobody"), humanized, fully human or chimeric antibodies, single-chain antibodies, diabodies, and antigen-binding fragments of antibodies (e.g., Fab fragments).

In certain embodiments, the antibody is an antibody fragment that does not contain the constant domain region of an antibody.

In certain embodiments, the antibody fragment is less than 500 amino acids in length, such as between 200-450 amino acids in length, or less than 400 amino acids in length.

In certain embodiments, the antibody has an amino acid sequence having at least 80% sequence identity of any one of SEQ ID NO: 42, 44, 46, or 48. In certain embodiments, the amino acid sequence has at least 90% sequence identity of any one of SEQ ID NO: 42, 44, 46, or 48. In certain embodiments, the amino acid sequence has at least 95% sequence identity of any one of SEQ ID NO: 42, 44, 46, or 48. In certain embodiments, the amino acid sequence has 100% sequence identity of any one of SEQ ID NO: 42, 44, 46, or 48. In certain embodiments, the present invention discloses a nucleic acid that encodes an antibody that preferentially recognizes human traumatic brain injury (TBI)-associated tau. In certain embodiments, the present invention provides a nucleic acid encoding an antibody that preferentially recognizes TBI-associated tau, wherein the nucleic acid has at least 80% sequence identity of any one of SEQ ID NO: 41, 43, 45, or 47. In certain embodiments, the nucleic acid sequence has at least 90% sequence identity of any one of SEQ ID NO: 41, 43, 45, or 47. In certain embodiments, the nucleic acid sequence has at least 95% sequence identity of any one of SEQ ID NO: 41, 43, 45, or 47. In certain embodiments, the nucleic acid sequence has 100% sequence identity of any one of SEQ ID NO: 41, 43, 45, or 47.

In certain embodiments, the present invention provides an antibody that preferentially recognizes a human Alzheimer's Disease (AD)-associated Tau.

In certain embodiments, the antibody is an antibody fragment that does not contain the constant domain region of an antibody.

In certain embodiments, the antibody fragment is less than 500 amino acids in length, such as between 200-450 amino acids in length, or less than 400 amino acids in length. In certain embodiments, the antibody has an amino acid sequence having at least 80% sequence identity of any one of SEQ ID NO: 2, 4, 6, 8, 10, 12, 14, 16, 18, 20, 22, 24, 26, 28, 30, 32, 34, 36, 38, or 40. In certain embodiments, the amino acid sequence has at least 90% sequence identity of any one of SEQ ID NO: 2, 4, 6, 8, 10, 12, 14, 16, 18, 20, 22, 24, 26, 28, 30, 32, 34, 36, 38, or 40. In certain embodiments, the amino acid sequence has at least 95% sequence identity of any one of SEQ ID NO: 2, 4, 6, 8, 10, 12, 14, 16, 18, 20, 22, 24, 26, 28, 30, 32, 34, 36, 38, or 40. In certain embodiments, the amino acid sequence has 100% sequence identity of any one of SEQ ID NO: 2, 4, 6, 8, 10, 12, 14, 16, 18, 20, 22, 24, 26, 28, 30, 32, 34, 36, 38, or 40.

In certain embodiments, the present invention discloses a nucleic acid that encodes an antibody that preferentially recognizes human AD-associated tau. In certain embodiments, the present invention provides a nucleic acid encoding an antibody that preferentially recognizes a human AD-associated tau, wherein the nucleic acid has at least 80% sequence identity of any one of SEQ ID NO: 1, 3, 5, 7, 9, 11, 13, 15, 17, 19, 21, 23, 25, 27, 29, 31, 33, 35, 37, or 39. In certain embodiments, the nucleic acid has at least 90% sequence identity of any one of SEQ ID NO: 1, 3, 5, 7, 9, 11, 13, 15, 17, 19, 21, 23, 25, 27, 29, 31, 33, 35, 37, or 39. In certain embodiments, the nucleic acid has at least 95% sequence identity of any one of SEQ ID NO: 1, 3, 5, 7, 9, 11, 13, 15, 17, 19, 21, 23, 25, 27, 29, 31, 33, 35, 37, or 39. In certain embodiments, the nucleic acid has 100% sequence identity of any one of SEQ ID NO: 1, 3, 5, 7, 9, 11, 13, 15, 17, 19, 21, 23, 25, 27, 29, 31, 33, 35, 37, or 39.

In certain embodiments, the present invention provides a vector comprising a nucleic acid described above.

In certain embodiments, the present invention provides a phage comprising the vector described above.

In certain embodiments, the present invention provides a method for determining risk of traumatic brain injury (TBI), assessment of the amount of neuronal damage, and/or susceptibility to neurodegenerative disease in a human, comprising the steps of:

(A) providing a sample obtained from a subject post-injury;

(B) detecting levels of human TBI-associated tau in the sample;

(C) comparing the TBI-associated tau protein level in the sample with TBI-associated tau protein level in a normal control; and (D) determining whether the human has a risk of TBI in accordance with the result of step (C);

wherein a subject having elevated TBI-associated tau protein has a high risk of TBI.

In certain embodiments, the present invention provides a method for determining the stage of Alzheimer's disease (AD) in a human, comprising the steps of:

(A) providing a sample obtained from a human;

(B) detecting levels of stage-specific human AD-associated tau in the sample;

(C) comparing the AD-associated tau protein level in the sample with AD-associated tau protein level in a normal control; and (D) determining whether the subject has a risk of AD in accordance with the result of step (C);

wherein a subject having elevated AD-associated tau protein has a high risk of AD.

In certain embodiments, the samples and the normal control are blood product samples or cerebrospinal fluid (CSF) samples.

In certain embodiments, the blood product is serum.

In certain embodiments, the detecting in step (B) is by means of a ligand specific for the protein.

In certain embodiments, the ligand is an antibody.

In certain embodiments, the ligand is a scFv.

In certain embodiments, the protein levels are detected by means of ELISA.

BRIEF DESCRIPTION OF THE FIGURES

FIG. 3a: Western blot of human AD and control brain tissue homogenates. Staining with polyclonal tau antibody shows presence of increased molecular weight tau species in AD patient sample compared to ND sample. Staining with the anti-phosphorylated tau antibody, AT8 shows presence of high molecular weight phosphorylated tau species in the AD sample with no phosphorylated tau species in the ND sample. FIG. 3b: Western blot of human AD and control brain tissue homogenates after immunoprecipitation with polyclonal anti-tau antibody. Staining with anti-phosphorylated tau antibody AT8, shows presence of high molecular weight phosphorylated tau species in AD sample with its absence in the ND sample.

DETAILED DESCRIPTION

Figure 1:
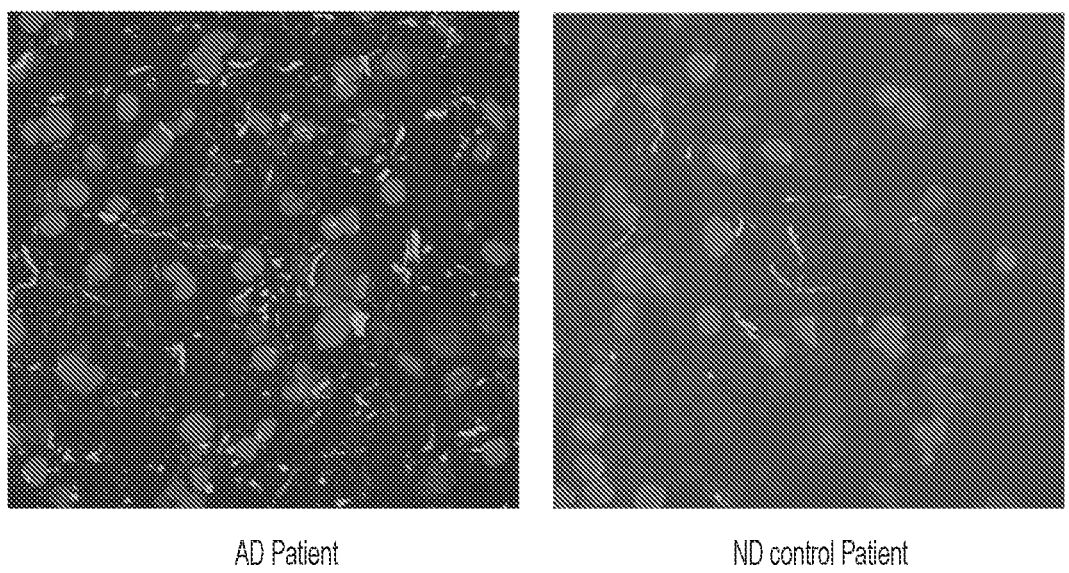
FIG. 1: Immunohistochemistry stain of human AD and control brain tissue slices showing increased presence of phosphorylated tau fibrils in the human AD tissue compared to the age matched cognitively normal sample. Tau was stained using the commercially available anti-phospho-tau antibody AT8.

A vast number of studies have correlated protein aggregation with neurodegenerative diseases including AD, Parkinson's and Dementia with Lewy Bodies. Numerous recent studies suggest that specific protein variants including selected oligomeric forms of these proteins are involved in neuronal toxicity and can interfere with important functions including long term potentiation. Various soluble oligomeric species of Aβ and a-syn have been shown to occur early during the course of AD and PD, and increasing evidence implicates oligomeric forms of tau in AD and other tauopathies.

A novel biopanning technology has been developed that combines the imaging capability of Atomic Force Microscopy (AFM) with the diversity of antibody libraries. This unique combination of antibody diversity and imaging capability allows for the isolation of single chain antibody variable domain fragment (scFv or nanobody) reagents to an array of morphologies of key proteins involved in neurodegenerative diseases including Aβ and alpha-synuclein (a-syn). Nanobodies have been isolated that specifically recognize monomeric, fibrillar, and two different oligomeric a-syn morphologies. The anti-oligomeric a-syn nanobodies do not cross react with oligomeric Aβ, and specifically label PD brain tissue but not AD or healthy tissue. In addition, nanobodies were isolated to different regions of full length Aβ and to three distinct naturally occurring oligomeric Aβ morphologies. One, A4, specifically recognizes a larger oligomeric Aβ species, inhibits aggregation and extracellular toxicity of Aβ, does not cross react with oligomeric a-syn, and specifically labels Aβ aggregates in human AD brain samples, but not PD or healthy brain tissue. A second nanobody, E1, recognizes a smaller trimeric or tetrameric Aβ species, and similar to A4 inhibits aggregation and extracellular toxicity of Aβ, does not cross react with oligomeric a-syn, and labels Aβ aggregates in human AD but not healthy brain tissue. Utilizing an AD brain derived oligomeric Aβ preparation, a third nanobody, C6, was isolated that specifically recognizes oligomeric Aβ species derived from human AD brain tissue, but does not recognize Aβ aggregates generated in vitro. The different specificities of each nanobody can be readily observed when each nanobody is expressed on the surface of a filamentous bacteriophage and antibody/antigen complexes are imaged by AFM. Therefore, the combination of antibody libraries and AFM imaging technologies enables the isolation and characterization of reagents that recognize specific protein variants including a variety of different naturally occurring aggregated forms of both a-syn and Aβ.

Another powerful advantage of this AFM panning protocol is that not only is it possible to isolate and characterize reagents to specific protein morphologies, but it is possible to do so using only picograms or less of material. In addition the sample does not need to be purified, and the protein does not need to be chemically modified in any way. It is possible to actually isolate nanobodies against a single molecule of the target antigen. This unique ability to generate and characterize reagents that specifically recognize individual protein variants provides the means to generate reagents that selectively recognize an array of different tau variants present in human AD brain.

While several reagents already exist that can recognize monomeric and phosphorylated tau, these reagents cannot distinguish between different aggregated states of tau. Reagents that can detect specific forms of tau can provide very powerful tools to facilitate diagnosis of AD and other tauopathies and to follow progression of these diseases or to evaluate therapeutic strategies. While many neurodegenerative diseases have overlapping clinical symptoms and cellular and biochemical mechanisms such as an increase in inflammatory markers, and aggregation of similar proteins, the reagents presently developed have well defined specificities and selectivities for selected tau forms and facilitate specific diagnoses of AD and other tauopathies. In combination with other protein and morphology specific reagents against Aβ and a-syn species, these reagents can be used to detect the presence of biomarkers which can readily detect and distinguish many related neurodegenerative diseases including AD, PD, FTD and LBD.

In addition to the unique reagents and ELISA protocol, other advantages of this proposal over previous studies include the use of postmortem tissue and CSF from cases with neuropathologically confirmed AD; the use of control subjects who have had standardized neuromotor assessment and postmortem neuropathologic examination, ensuring that they are not in preclinical stages of AD or other neurodegenerative disease, and the use of a significant number of cases, compensating for individual variation as well as allowing stratification for possible significant influences on disease severity.

Traumatic Brain Injury

It is well established that chronic stress and especially traumatic brain injury (TBI) can disrupt cognitive functioning. The brain is very sensitive to stress and injury and responds by expressing a variety of neuromorphological and neurochemical changes. Stress induces increases in expression levels in the hippocampus of the Amyloid Precursor Protein (APP) and BACE-1, a protease which cleaves APP. These increases are of particular relevance for soldiers suffering TBI since similar increases in hippocampal expression of APP and BACE-1 are strongly linked with the onset and progression of Alzheimer's disease (AD). BACE-1 cleavage of APP results in generation of the beta-amyloid (Aβ) protein, the primary component of the hallmark amyloid plaques associated with AD. Numerous studies have indicated that patients suffering brain trauma are at greater risk of developing AD and at an earlier age. The brain experiences very high sheer forces and mechanical deformation following TBI, and neuronal axons, particularly in the white matter are very susceptible to injury. Resulting damage to the neuronal axons can impair protein transport leading to accumulation of proteins and swelling causing the typical axon pathology observed with TBI. Various forms of stress induce memory deficits in mice and rats, with accompanying increases in APP, BACE-1 and Aβ levels.

Increased expression of APP and BACE-1 results in increased production of Aβ, which in turn can promote aggregation of this natively unstructured protein into a variety of soluble aggregate species some of which are potent neurotoxins that inhibit long term potentiation and other neuronal functions. Aβ can also self-assemble into much larger aggregates which eventually form the distinctive insoluble amyloid fibrils which are a hallmark of AD brain tissue. A vast amount of literature implicates Aβ accumulation as being central to the progression of AD, leading to formation of the Aβ hypothesis. The major weakness of the Aβ hypothesis however, is that the presence of amyloid plaques does not correlate well with the progression of AD. While Aβ can form amyloid plaques, it also forms a number of soluble intermediate or metastable structures which may contribute to toxicity. Cortical levels of soluble Aβ correlated well with the cognitive impairment and loss of synaptic function. Small, soluble aggregates of Aβ termed Aβ-derived diffusible ligands and spherical or annular aggregates termed protofibrils are neurotoxic. Oligomeric forms of Aβ, created in vitro or derived from cell cultures inhibit long term potentiation. The concentration of oligomeric forms of Aβ is also elevated in transgenic mouse models of AD and in human AD brain and CSF samples. Disruption of neural connections near Aβ plaques was also attributed to oligomeric Aβ species. A halo of oligomeric Aβ surrounds Aβ plaques causing synapse loss, and oligomeric Aβ was shown to disrupt cognitive function in transgenic animal models of AD. Different size oligomers of Aβ have been correlated with AD, including a 56 kD aggregate and smaller trimeric and tetrameric species. Therefore, the presence of oligomeric Aβ is strongly correlated with neuronal dysfunction and memory deficits following neuronal damage and plays a critical role in progression of AD.

Given the critical role of APP and BACE-1 in cognitive deficits associated with AD, it is likely that similar increases in APP and BACE-1 levels induced by stress and injury to the brain also lead to elevated Aβ levels, promoting formation of neurotoxic aggregate species, and subsequent memory loss and neuronal dysfunction. Following induced trauma to the brain, substantial deposition of non-fibrillar Aβ aggregates has been observed throughout the brain, even after only a single event. Significantly, when TBI is induced in animal models of AD, there is a substantial increase in neuronal death, memory disorders, and Aβ accumulation, but no corresponding increase in Aβ plaque deposition, there was even a decrease in observed plaques. A preponderance of studies now indicate that various soluble oligomeric Aβ aggregates play a very critical role in neuronal dysfunction rather than the hallmark fibrillar Aβ plaques that have long been associated with AD. An observed increase in Aβ levels in CSF samples from TBI patients suggests that detection of specific Aβ species in CSF and serum represents a promising route for early detection of AD like brain injury in soldiers suffering TBI.

Since TBI also induces axonal injury and damage to protein transport mechanisms, neurofilament proteins may also play a role in TBI and AD. Neurofilament proteins accumulate in axons following TBI, and several studies have implicated the neurofilament protein tau in this process. The second major pathological feature of AD brains is the presence of neurofibrillary tangles that contain aggregates of the microtubule associated protein, tau. Tau is also a natively unfolded protein similar to Aβ, and can aberrantly fold into various aggregate morphologies including β-sheet containing fibrillar forms and different oligomeric species. Tau plays an important role in assembly and stabilization of microtubules and can undergo numerous post-translational modifications including phosphorylation, glycosylation, glycation, prolyl-isomerization, cleavage or truncation, nitration, polyamination, ubiquitination, sumoylation, oxidation and aggregation. Tau has 85 putative phosphorylation sites, and excess phosphorylation can interfere with microtubule assembly. Elevated total tau concentration in CSF has been correlated with AD, as has the presence of various phosphorylated tau forms and the ratio of tau to Aβ42. In addition to phosphorylation, tau can be modified by reactive nitrogen and oxygen species, leading to modified tau forms that are prone to assemble into aggregate species including different oligomeric forms. Levels of oligomeric tau have also been implicated as a potential early diagnostic for AD. Therefore, determination of total tau, phosphorylated tau and oligomeric tau concentrations all have potential value as diagnostics for neurodegenerative disorders including tauopathies, AD and TBI.

Tau is a very complex protein in vivo as alternative splicing of the second, third and tenth exons of tau result in generation of six tau isoforms of varying length in the CNS. The assembly domain in the carboxyl-terminal portion of the protein contains either three or four repeats (3R or 4R) of a conserved tubulin-binding motif depending on alternative splicing of exon 10. Tau 4R isoforms have greater microtubule binding and stabilizing ability than the 3R isoforms. Human adult brains have similar levels of 3R and 4R isoforms, whereas only 3R tau is expressed at the fetal stage. In tauopathies, mutations altering the splicing of tau transcript and the ratio of 3R to 4R tau isoforms are sufficient to cause neurodegenerative disease. Therefore tau in human brain tissue can exist in a variety of different lengths and morphologies and with multiple post-translational modifications.

Tau plays a critical role in the pathogenesis of AD and studies show that reduction of tau levels in AD animal models reverses disease phenotypes and that tau is necessary for the development of cognitive deficits in AD models caused by over-expression of Aβ. While NFTs have been implicated in mediating neurodegeneration in AD and tauopathies, animal models of tauopathy have shown that memory impairment and neuron loss do not associate well with accumulation of NFT. In animal models expressing human tau, neurodegeneration-related phenotypes including behavioral impairments, neuronal loss, and synapse lesions correlate better with the presence of soluble tau oligomers and pre-filament species than with fibrillar NFT levels. Neuronal loss also precedes NFT formation suggesting involvement of other species such as oligomeric tau variants. In addition, animal studies showed that hippocampal synapse loss and dysfunction and microglial activation occurred months before the accumulation of filamentous tau inclusions. Both brain derived and recombinant oligomeric tau aggregate species disrupt intracellular calcium levels and are toxic to cultured human neuronal cells when added extracellularly. The pathological structures of tau most closely associated with AD progression were shown to be tau oligomers. In postmortem human brains, high oligomeric tau levels were detected in the frontal lobe cortex at early stages of AD before the presence of NFTs. Oligomeric tau may also be responsible for transmission of pathology with a prion-like mechanism as NFT tau pathology spreads from brain regions seeded with oligomeric tau into other regions resulting in aggregation of endogenous tau. It has been previously shown using recombinant human tau (rhTau) that extracellular trimeric, but not monomeric or dimeric species are toxic to human neuronal cells.

All these studies suggest that tau tangles are not acutely neurotoxic, but rather that pretangle oligomeric tau species are responsible for the neurodegenerative phenotype, similar to toxic role of oligomeric Aβ species. Therefore both toxic oligomeric Aβ and tau species in CSF and serum have promise as early biomarkers for AD and for AD like damage in TBI patients.

Similar to the role of Aβ and tau in AD, aggregation of alpha-synuclein (a-syn) plays a critical role in PD and synucleinopathies. A-syn is a major component of Lewy bodies and neurites. Wild-type a-syn along with the three mutant forms, A30P, E46K and A53T can assemble into Lewy body like fibrils in vitro. Since all of the mutations increase the total rate of oligomerization compared to the wild-type form of a-syn, it has been postulated that the intermediate oligomeric morphologies of a-syn are the toxic structures in PD rather than fibrils. A partially folded intermediate of a-syn helps to promote fibril formation in vitro and a protofibrillar form of a-syn is stabilized by formation of a dopamine adduct complex, suggesting a possible connection between this morphology of a-syn and dopaminergic cell death. The different morphologies of a-syn also have different affinities for various membranes, and both the oligomeric forms and fibrillar forms have been shown to disrupt membrane permeability and integrity. Aggregated forms of a-syn were shown to induce toxicity in dopaminergic neurons in vivo and several different oligomeric morphologies were shown to each have different toxic mechanisms and effects on cells. We have shown that oligomeric but not fibrillar forms of a-syn are toxic to neuronal cells. Toxic oligomeric a-syn forms were identified in living cells, in human plasma from PD patients, and in human PD brain tissue indicating that oligomeric a-syn is also a good biomarker for neuronal damage.

Clearly protein misfolding and aggregation is critically important in many devastating neurodegenerative diseases. Therefore, determining how concentration profiles of selected key forms and morphologies of Aβ, tau and a-syn vary in AD, TBI and cognitively normal patients will facilitate development of an effective diagnostic assay for these diseases. In order to assess the value of these protein aggregates as biomarkers in neuronal disease, highly specific reagents are needed that can selectively identify the different toxic protein species. Our lab has developed unique technology that enables us to isolate reagents that bind specific morphologies of a target protein. We have combined the imaging capabilities of AFM with the binding diversity of phage display antibody technology to allow us to identify the presence of specific protein morphologies and then isolate reagents that bind a target morphology. These morphology specific reagents have promise for assessing whether the specific toxic aggregate species in human samples such as serum, plasma or CSF are useful biomarkers for neuronal damage. CSF levels of Aβ and tau have been useful to predict AD, however biomarker studies of TBI patients have been less successful, where S100B has been the only marker to consistently predict TBI and outcome. S100B is a calcium binding protein that has been implicated in various diseases including AD, diabetes, melanoma and epilepsy, so its use in predicting TBI may be limited. We have developed a series of morphology specific nanobodies that have great promise for distinguishing between different neurodegenerative diseases. These nanobodies selectively recognize toxic protein aggregate biomarkers that are associated with specific diseases, therefore these nanobodies are recognizing biomarkers that are associated with the onset and progression of specific diseases, rather than recognizing a more generic secondary effect such as inflammatory signals, microglial activation or apoptotic markers. We have shown that three different nanobodies against different oligomeric Aβ species all selectively distinguish between AD and PD or healthy samples in post-mortem human tissue and CSF samples. We have similarly shown that two different nanobodies against different toxic oligomeric a-syn species both selectively distinguish between PD and AD or healthy post-mortem human tissue and CSF samples. When we assayed post-mortem tissue, CSF and serum samples from AD, PD and cognitively normal patients with our anti-oligomeric Aβ, a-syn and tau nanobodies, we can not only readily distinguish AD, PD and normal samples but we can also stage progression of these different diseases. Also in the preliminary data section and of direct relevance to this proposal, we show that we can not only detect the presence of toxic oligomeric morphologies of Aβ, tau and a-syn in ante-mortem human serum samples, but that there is a very distinct spike in oligomeric Aβ species in serum many years prior to diagnosis of AD, and even several years prior to diagnosis of mild-cognitive impairment (MCI) suggesting that we can presymptomatically diagnose AD by analysis of serum samples many years before symptoms of AD occur. Since early, even presymptomatic diagnosis of AD is critical so that preventative and treatment therapies can begin before extensive neuronal damage has occurred, the studies proposed here have very high potential impact. The morphology specific nanobodies we have developed and other nanobodies that have been developed are powerful tools to characterize human tissue, CSF and serum samples and to distinguish between different neurodegenerative diseases. Since the nanobodies recognize toxic species that should be present at early stages of disease progression, these nanobodies should be useful as early presymptomatic biomarkers for different neurodegenerative diseases, and to identify soldiers who are susceptible to AD following TBI.

The following human AD-associated Tau clone sequences were identified:

```
Clone 32B:
                                                    (SEQ ID NO: 1)
GATTACNGCCAAGCTTGCATGCAAATTNTATTTCAAGGAGNCAGTCATAATG

AAATACNTATTGCCTNCGNCAGCCGCTGGATTGTTATTACTCGCGGCCCAGCCGGCC

ATGGCCGAGGTGCAGCTGTTGGAGTCTGGGGGAGGCTTGGTACAGCCTGGGGGGTC

CCTGAGACTCTCCTGTGCAGCCTCTGGATTCACCTTTAGCAGCTATGCCATGAGCTG

GGTCCGCCAGGCTCCAGGGAAGGGGCTGGAGTGGGTCTCATCTATTTCTTCTAATGG

TGATGATACAGCTTACGCAGACTCCGTGAAGGGCCGGTTCACCATCTCCAGAGACA

ATTCCAAGGACACGCTGTATCTGCAAATGAACAGCCTGAGAGCCGAGGACACGGCC

GTATATTACTGTGCGAAAGCTAATAATTCTTTTGACTACTGGGGCCAGGGAACCCTG

GTCACCGTCTCGAGCGGTGGAGGCGGTTCAGGCGGAGGTGGCAGCGGCGGTGGCG

GGTCGACGGACATCCAGATGACCCAGTCTCCATCCTCCCTGTCTGCATCTGTAGGAG

ACAGAGTCACCATCACTTGCCGGGCAAGTCAGAGCATTAGCAGCTATTTAAATTGG

TATCAGCAGAAACCAGGGAAAGCCCCTAAGCTCCTGATCTATAATGCATCCACTTT

GCAAAGTGGGGTCCCATCAAGGTTCAGTGGCAGTGGATCTGGGACAGATTTCACTC

TCACCATCAGCAGTCTGCAACCTGAAGATTTTGCAACTTACTACTGTCAACAGGATA

GTGCTACTCCTTATACGTTCGGCCAAGGGACCAAGGTGGAAATCAAACGGGCGGCC

GCACATCATCATCACCATCACGGGGCCGCAGAACAAAAACTCATCTCAGAAGAGGA

TCTGAATGGGCCGC

32B AA sequence:
                                                    (SEQ ID NO: 2)
MKYXLPXXAAGLLLLAAQPAMAEVQLLESGGGLVQPGGSLRLSCAASGFTFSS

YAMSWVRQAPGKGLEWVSSISSNGDDTAYADSVKGRFTISRDNSKDTLYLQMNSLRA

EDTAVYYCAKANNSFDYWGQGTLVTVSSGGGGSGGGGSGGGGSTDIQMTQSPSSLSAS

VGDRVTITCRASQSISSYLNWYQQKPGKAPKLLIYNASTLQSGVPSRFSGSGSGTDFTLTI

SSLQPEDFATYYCQQDSATPYTFGQGTKVEIKRAAAHHHHHHGAAEQKLISEEDLNGA
```

-continued

Clone 51A:
(SEQ ID NO: 3)
TATGANCCATGATTACGCCAAGCTNNCATGCAANNTNTATTTTCAAGGAGAC

AGTCATAATGAAATACCTATTGCNTACGNCAGCCGCTNNGATTGTTATTACTCGCGG

CCNCAGCCGGCCATGGCCGAGGTGCAGCTGTNGGAGTCTGGGGGAGGCTTGGTACA

GCCTGGGGGTCCCTGAGACTCTCCTGTGCAGCCTCTGGATTCACCTTTAGCAGNTA

TGCCATGAGCTGGGTCCGCCAGGCTCCAGGGAAGGGGCTGGAGTGGGTCTCATAGA

TTTAGCAGTCGGGTCCGGTTACATCTTACGCAGACTCCGTGAAGGGCCGGTTCACCA

TCTCCAGAGACAATTCCAAGAACACGCTGTATCTGCAAATGAACAGCCTGAGAGCC

GAGGACACGGCCGTATATTACTGTGCGAAACGTCAGTTGATGTTTGACTACTGGGG

CCAGGGAACCCTGGTCACCGTCTCGAGCGGTGGAGGCGGTTCAGGCGGAGGTGGCA

GCGGCGGTGGCGGGTCGACGGACATCCAGATGACCCAGTCTCCATCCTCCCTGTCT

GCATCTGTAGGAGACAGAGTCACCATCACTTGCCGGGCAAGTCAGAGCATTAGCAG

CTATTTAAATTGGTATCAGCAGAAACCAGGGAAAGCCCCTAAGCTCCTGATCTATG

CTGCATCCAGTTTGCAAAGTGGGGTCCCATCAAGGTTCAGTGGCAGTGGATCTGGG

ACAGATTTCACTCTCACCATCAGCAGTCTGCAACCTGAAGATTTTGCAACTTACTAC

TGTCAACAGAGTTACAGTACCCCTAATACGTTCGGCCAAGGGACCAAGGTGGAAAT

CAAACGGGCGGCCGCACATCATCATCACCATCACGGGGCCGCAGAACAAAAACTCA

TCTCAGAAGAGGATCTGAATGGGCCGCATAG

51A AA sequence:
(SEQ ID NO: 4)
MAEVQLXESGGGLVQPGGSLRLSCAASGFTFSXYAMSWVRQAPGKGLEWVSIQ

SGPVTSYADSVKGRFTISRDNSKNTLYLQMNSLRAEDTAVYYCAKRQLMFDYWGQGT

LVTVSSGGGGSGGGGSGGGGSTDIQMTQSPSSLSASVGDRVTITCRASQSISSYLNWYQ

QKPGKAPKLLIYAASSLQSGVPSRFSGSGSGTDFTLTISSLQPEDFATYYCQQSYSTPNTF

GQGTKVEIKRAAAHHHHHHGAAEQKLISEEDLNGPH

Clone 51F:
(SEQ ID NO: 5)
ATTNCGCCAAGCTNNCATGCAAAATTTNTATTTNAANGGAGACAGTCATAAT

GAAATACCTATTGCNTACNNNNNNNCGCTGGATTGTTATTACTCGCGGNNCAGCCG

GCCATGGCCGAGGTGCAGCTGTTGGAGTCTGGGGGAGGCTTGGTACAGCCTGGGGG

GTCCCTGAGACTNTCCTGTGCAGCNTCTGGATTCACCTTTAGCAGCTATGCCATGAN

NTGGGTCCGCCAGGCTCCAGGGAAGGGGCTGNNNNNNGTNTCATCTATTACGTAGA

CGGGTTCGTAGACACAGTACGCAGACTCCGTGAAGGGCAGGTTCACCATCTCCAGA

GACAATTCCAAGAACACGCTGTATCTGCAAATGAACAGCCTGAGAGCCGAGGACAC

GGCCGTATATTACTGTGCGAAACAGCATGATGATTTTGACTACTGGGGCCAGGGAA

CCCTGGTCACCGTCTCGAGCGGTGGAGGCGGTTCAGGCGGAGGTGGCAGCGGCGGT

GGCGGGTCGACGGACATCCAGATGACCCAGTCTCCATCCTCCCTGTCTGCATCTGTA

GGAGACAGAGTCACCATCACTTGCCGGGCAAGTCAGAGCATTAGCAGCTATTTAAA

TTGGTATCAGCAGAAACCAGGGAAAGCCCCTAAGCTCCTGATCTATACTGCATCCA

ATTTGCAAAGTGGGGTCCCATCAAGGTTCAGTGGCAGTGGATCTGGGACAGATTTC

ACTCTCACCATCAGCAGTNTGCAACCTGAAGATTTTGCAACTTANTACTGTCAACAG

CTGGATGTGTNTCCTTNGACGTTCGGNCAANNNACCAAGGTGGAAATCAA

-continued

51F AA sequence:
(SEQ ID NO: 6)
MAEVQLLESGGGLVQPGGSLRXSCAXSGFTFSSYAMXWVRQAPGKGLXXXSSI

TTGSTQYADSVKGRFTISRDNSKNTLYLQMNSLRAEDTAVYYCAKQHDDFDYWGQGT

LVTVSSGGGGSGGGGSGGGGSTDIQMTQSPSSLSASVGDRVTITCRASQSISSYLNWYQ

QKPGKAPKLLIYTASNLQSGVPSRFSGSGSGTDFTLTISSXQPEDFATXYCQQLDVXPXT

FXQXTKVEI

Clone 52H:
(SEQ ID NO: 7)
GAGACAGTCATAGCTAGCATGAAAAAGANTTGGCTGGCGCTGGCTGGTTTAG

TTTTagCGTTTAGCGCATCGGCGGACTACAAAGAGGCCCAGCCGGCCATGGACCTGG

GTAAGAAACTGCTGGAAGCTGCTCGTGCTGGTCAGGACGACGAAGTTCGTATCCTG

ATGGCTAACGGTGCTGACGTTAACGCTGACGACTACGAAGGTTGGACTCCGCTGCA

CCTGGCTGCTATGGTTGGTCACCTGGAAATCGTTGAAGTTCTGCTGAAGTACGGTGC

TGACGTTAACGCTCAGGACAAATTCGGTAAGACCGCTTTCGACATCTCCATCGACA

ACGGTAACGAGGACCTGGCTGAAATCCTGCAAGCGGCCGCACATCATCATCACCAT

CACGGGGCCGCAGAACAAAAACTCATCTCAGAAGAGGATCTGAATGGGGCCGCAT

AGACTGTTGAAAGTTGTTTAGCAAAACCTCATACAGAAAATTCATTTACTAACGTCT

GGAAAGACGACAAAACTTTAGATCGTTACGCTAACTATGAGGGCTGTCTGTGGAAT

GCTACAGGCGTTGTGGTTTGTACTGGTGACGAAACTCAGTGTTACGGTACATGGGTT

CCTATTGGGCTTGCTATCCCTGAAAATGAGGGTGGTGGCTCTGANGGTGGCGGTTCT

GAGGGTGGCGGTTCTGANGGTGGCGGTACTAAACCTCCTGAGTACGGTGATACACC

TATTCCGGGCTATACTTATATCAACCCTCTCGACNGCACTTATCCGCCTGGTACTGA

GCAAAACCCCGCTAATCCTAATCCCTTCTCTTGAGGAGTCTCAGCCTCTTAATACTT

TCATGTTTCANAATAATANNTTCCGAAATNNNCNNGGTGCATTAACTGTTTATACNG

GCACTGTTACTCNANNNACTGACCCCCGTTTAAAACTTATTACCAGTACACTCCNTG

NNATCAT

52H AA sequence:
(SEQ ID NO: 8)
MKKXWLALAGLVLAFSASADYKEAQPAMDLGKKLLEAARAGQDDEVRILMA

NGADVNADDYEGWTPLHLAAMVGHLEIVEVLLKYGADVNAQDKFGKTAFDISIDNGN

EDLAEILQAAAHHHHHGAAEQKLISEEDLNGAA

Clone M32B:
(SEQ ID NO: 9)
TTCAGGAGANAGTCNTAATGAAATACCTATTGCCTACGGCAGCCGCTGGAtT

GTTATTACTCGCGGNCCAGCCGGCCATGGCCGAGGTGCAGCTGTTGGAGTCTGGGG

GAGGCTTGGTACAGCCTGGGGGGTCCCTGAGACTCTCCTGTGCAGCCTCTGGATTCA

CCTTTAGCAGCTATGCCATGAGCTGGGTCCGCCAGGCTCCAGGGAAGGGGCTGGAG

TGGGTCTCAGGTATTTCTAATAATGGTAGTAATACAACTTACGCAGACTCCGTGAAG

GGCCGGTTCACCATCTCCAGAGACAATTCCAAGAACACGCTGTATCTGCAAATGAA

CAGCCTGAGAGCCGAGGACACGGCCGTATATTACTGTGCGAAAGCTTCTTATACTTT

TGACTACTGGGGCCAGGGAACCCTGGTCACCGTCTCGAGCGGTGGAGGCGGTTCAG

GCGGAGGTGGCAGCGGCGGTGGCGGGTCGACGGACATCCAGATGACCCAGTCTCCA

TCCTCCCTGTCTGCATCTGTAGGAGACAGAGTCACCATCACTTGCCGGGCAAGTCAG

AGCATTAGCAGCTATTTAAATTGGTATCAGCAGAAACCAGGGAAAGCCCCTAAGCT

-continued

```
CCTGATCTATAGTGCATCCTCTTTGCAAAGTGGGGTCCCATCAAGGTTCAGTGGCAG

TGGATCTGGGACAGATTTCACTCTCACCATCAGCAGTCTGCAACCTGAAGATTTTGC

AACTTACTACTGTCAACAGTATTCTGGTTCTCCTGCTACGTTCGGCCNAGGGACCAA

GGTGGAAATCANACGGGCGGCCGCACNTCATCATNNCCATCACGGGGCCGCAGAA

NNAAAACTCATCTCAGAAGAGGANNTGAATGGGGCCGCATAGACTGTT
```

M32B AA sequence:
(SEQ ID NO: 10)
```
MKYLLPTAAAGLLLLAXQPAMAEVQLLESGGGLVQPGGSLRLSCAASGFTFSSY

AMSWVRQAPGKGLEWVSGISNNGSNTTYADSVKGRFTISRDNSKNTLYLQMNSLRAE

DTAVYYCAKASYTFDYWGQGTLVTVSSGGGGSGGGGSGGGGSTDIQMTQSPSSLSASV

GDRVTITCRASQSISSYLNWYQQKPGKAPKLLIYSASSLQSGVPSRFSGSGSGTDFTLTIS

SLQPEDFATYYCQQYSGSPATFGXGTKVEIXRAAAXHHXHHGAAEXKLISEEX
```

Clone M32E:
(SEQ ID NO: 11)
```
TTCAGGANANAGTCATAATGAANTACCTATTGCCTACGGCAGCCGCTGGANT NNTATTACTCGCGGCCCAgCCGGCCATGGCCCANGTGCAGCTGGTGGAGTCTGGGG

GAGGCGTGGTCCAGCCTGGGAGGTCCCTGAGACTCTCCTGTGCAGNCTCCGGATTC

ACCTTTANCAGCTATGACATGGGCTGGGTCCGCCAGGCTCCAGGGAAGGGGCTGGA

GTGGGTCTCAAGTATTAGTGGTAGTGGTCCTACCATGAACTACGCANACTCTGTGAA

GGGCCGATTCACCGTCTCCAGAGACAATTCCAAGAACACGCTGTATCTGCAAATGG

ACAGCCTGAGAGCCGAGGACACGGCCGTATATTACTGTGCGAAAGGGGGTACGGA

CTTTGACTACTGGGGCCAGGGCACCCTGGTCACCGTCTCCTCAGGNGGAGGCGGTT

CANGCGGAGGTGGCTCTGGCGGTGGCGGATCGTCTGAGCTGACTCAGGACCCTGCT

GTGTCTGTGGCCTTGGGACAGACAGTCANCATCACATGCCAAGGANACAGCCTCNN

AACCTATTATGCAAGCTGGTACCANCANAAGCCAGGACAGGCCCCTGTACTTGTCA

TCTATGGNAAAAACAACCGGCCCTCANGGATCNCAGACCGATTCTCTGGCTCCAGC

TCANGAAACACAGCTTCCTTGACCATCACTGNGGCTCAGGCGGAAGATGAGGCTGA

CTATTACTGNAACTCCCGGGACAGCAGTGNNAACCATCTNANGAGTGTTCGGCGGA

GGGANCNNGCTGACCGNCTANGTGCGGCCGCAGNACNNNNNCTNCNNNTCAGA

ANANGATCTGAATGGGGCNNCATANACTGTTGNAAANNNGNTTANCAA
```

M32E AA sequence:
(SEQ ID NO: 12)
```
MXYLLPTAAAGXXLLAAQPAMAXVQLVESGGGVVQPGRSLRLSCAXSGFTFXS

YDMGWVRQAPGKGLEWVSSISGSGPTMNYAXSVKGRFTVSRDNSKNTLYLQMDSLRA

EDTAVYYCAKGGTDFDWGQGTLVTVSSXGGGSXGGGSGGGGSSELTQDPAVSVALG

QTVXITCQGXSLXTYYASWYXXKPGQAPVLVIYXKNNRPSXIXDRFSGSSSXNTASLTI

TXAQAEDEADYYXNSRDSSXNHXXSVRRR
```

Clone M33F:
(SEQ ID NO: 13)
```
TTCAGGAGANAGTCNTAATGAAATACCTATTGCCTACGGCAGCCGCTGGATT

GTTATTACTCGCGGCCCAGCCGGCCATGGCCGAGGTGCAGCTGTTGGAGTCTGGGG

GAGGCTTGGTACAGCCTGGGGGGTCCCTGAGACTCTCCTGTGCAGCCTCTGGATTCA

CCTTTAGCAGCTATGCCATGAGCTGGGTCCGCCAGGCTCCAGGGAAGGGGCTGGAG

TGGGTCTCAGCTATTACTAATGATGGTGCTGGTACAACTTACGCAGACTCCGTGAAG
```

-continued

```
GGCCGGTTCACCATCTCCAGAGACAATTCCAAGAACACGCTGTATCTGCAAATGAA

CAGCCTGAGAGCCGAGGACACGGCCGTATATTACTGTGCGAAATCTTATACTGGTTT

TGACTACTGGGGCCAGGGAACCCTGGTCACCGTCTCGAGCGGTGGAGGCGGTTCAG

GCGGAGGTGGCAGCGGCGGTGGCGGGTCGACGGACATCCAGATGACCCAATCTCCA

TCCTCCCTGTCTGCATCTGTAGGAGACAGAGTCACCATCACTTGCCGGGCAAGTCAG

AGCATTAGCAGCTATTTAAATTGGTATCAGCAGAAACCAGGGAAAGCCCCTAAGCT

CCTGATCTATACTGCATCCACTTTGCAAAGTGGGNTCCCATTAAGGTTCAGTGGCAG

TGGATCTGGGACAGATTTCACTCTCACCATCAGCAGTCTGCAACCTGAAGATTTTGC

AACTTACTACTGTCAACAGANNTATGCTANTCCTANNACGTTCGGNCNANGGGACC

NNNGNNNNAAATCANNCGGGCGGCCGCACNNCATNATNNNNNATNCNCGNNNNCG

CAGAACAAAACTC
```

M33F AA sequence:
(SEQ ID NO: 14)
```
MKYLLPTAAAGLLLLAAQPAMAEVQLLESGGGLVQPGGSLRLSCAASGFTFSSY

AMSWVRQAPGKGLEWVSAITNDGAGTTYADSVKGRFTISRDNSKNTLYLQMNSLRAE

DTAVYYCAKSYTGFDYWGQGTLVTVSSGGGGSGGGGSGGGGSTDIQMTQSPSSLSASV

GDRVTITCRASQSISSYLNWYQQKPGKAPKLLIYTASTLQSGXPLRFSGSGSGTDFTLTIS

SLQPEDFATYYCQQXYAXPXTF
```

Clone M34C:
(SEQ ID NO: 15)
```
CTANGCGNCCNNTTNAGATCCTCTTCTGAGANGAGTTTTTGTTCTGCGGCCCC

GTGATGGTGATGATGATGTGCGGCCGCCCGTTTGATTTCCACCTTGGTCCCTTGGCC

GAACGTCGCAGGAGTCTGATGAGTCTGTTGACAGTAGTAAGTTGCAAAATCTTCAG

GTTGCAGACTGCTGATGGTGAGAGTGAAATCTGTCCCAGATCCACTGCCACTGAAC

CTTGATGGGACCCCACTTTGCAACTGGGATGCCGGATAGATCAGGAGCTTAGGGGC

TTTCCCTGGTTTCTGCTGATACCAATTTAAATAGCTGCTAATGCTCTGACTTGCCCGG

CAAGTGATGGTGACTCTGTCTCCTACAGATGCAGACAGGGAGGATGGAGACTGGGT

CATCTGGATGTCCGTCGACCCGCCACCGCCGCTGCCACCTCCGCCTGAACCGCCTCC

ACCGCTCGAGACGGTGACCAGGGTTCCCTGGCCCCAGTAGTCAAAAGACCAAAACT

GTTTCGCACAGTAATATACGGCCGTGTCCTCGGCTCTCAGGCTGTTCATTTGCAGAT

ACAGCGTGTTCTTGGAATTGTCTCTGGAGATGGTGAACCGGCCCTTCACGGAGTCTG

CGTACGTTGTCGGCGGACCCTGCTTCGCAATATCTGAGACCCACTCCAGCCCCTTCC

CTGGAGCCTGGCGGACCCAGCTCATGGCATAGCTGCTAAAGGTGAATCCAGAGGCT

GCACAGGAGAGTCTCANGGACCCCCAGGCTGTACCAAGCCTCCCCCAGACTCCAA

CAGCTGCACCTCGGCCATGGCCGGCTGGGCCGCGAGTAATAACAATCCAGCGGCTG

CCGTANGCAATANGTATTTCATTATGACTGTCTCCTTGAAATAGAATTTGCATGCAA

GCTTGGNNTANNATGGNCATAGCTGTTTNCTGTGTGAAATNGNTATNCNNTCNCAA

TTCCNCACAANATAC
```

M34C AA sequence:
(SEQ ID NO: 16)
```
MKYXLXTAAAGLLLLAAQPAMAEVQLLESGGGLVQPGGSXRLSCAASGFTFSS

YAMSWVRQAPGKGLEWVSDIAKQGPPTTYADSVKGRFTISRDNSKNTLYLQMNSLRA

EDTAVYYCAKQFWSFDWGQGTLVTVSSGGGGSGGGGSGGGGSTDIQMTQSPSSLSA
```

-continued

SVGDRVTITCRASQSISSYLNWYQQKPGKAPKLLIYPASQLQSGVPSRFSGSGSGTDFTL
TISSLQPEDFATYYCQQTHQTPATFGQGTKVEIKRAAAHHHHHGAAEQKLXSEED

Clone M34F:
(SEQ ID NO: 17)
CATTCNGATCCTCTTCTGAGANGAGTTTTTGTTCTGCGGCCCCGTGATGGTGA
TGATGATGTGCGGCCGCCCGTTTGATTTCCACCTTGGTCCCTTGGCCGAACGTAATA
GGAGACGGATGCGACTGTTGACAGTAGTAAGTTGCAAAATCTTCAGGTTGCAGACT
GCTGATGGTGAGAGTGAAATCTGTCCCAGATCCACTGCCACTGAACCTTGATGGGA
CCCCACTTTGCAAATTGGATGCCCTATAGATCAGGAGCTTAGGGGCTTTCCCTGGTT
TCTGCTGATACCAATTTAAATAGCTGCTAATGCTCTGACTTGCCCGGCAAGTGATGG
TGACTCTGTCTCCTACAGATGCAGACAGGGAGGATGGAGACTGGGTCATCTGGATG
TCCGTCGACCCGCCACCGCCGCTGCCACCTCCGCCTGAACCGCCTCCACCGCTCGAG
ACGGTGACCAGGGTTCCCTGGCCCCAGTAGTCAAACGCCGTCCAACGTTTCGCACA
GTAATATACGGCCGTGTCCTCGGCTCTCAGGCTGTTCATTTGCAGATACAGCGTGTT
CTTGGAATTGTCTCTGGAGATGGTGAACCGGCCCTTCACGGAGTCTGCGTAAATTGT
CGGACTACCACCCCCAGCAATCGATGAGACCCACTCCAGCCCCTTCCCTGGAGCCT
GGCGGACCCAGCTCATGGCATAGCTGCTAAAGGTGAATCCAGAGGCTGCACAGGAG
AGTCTCANGGACCCCCAGGCTGTACCAAGCCTCCCCCAGACTCCAACAGCTGCAC
CTCGGCCATGGCCGGCTGGGCCGCGAGTAATAACAATCCAGCGGCTGCCGTANGCA
ATAGGTATTTCATTATGACTGTCTCCTTGAAATAGANTTTGCATGCAAGCTTGGCGT
AANTCATGGNCATAGCTGTTTCCTGTGTGAAATTGTTATCCNCTCACAANTTCCNCN
CAANCATACGAANCCCGGAANGC M34F AA sequence:
(SEQ ID NO: 18)
MXMXYAKLACKXYFKETVIMKYLLXTAAAGLLLLAAQPAMAEVQLLESGGGL
VQPGGSXRLSCAASGFTFSSYAMSWVRQAPGKGLEWVSSIAGGGSPTIYADSVKGRFTI
SRDNSKNTLYLQMNSLRAEDTAVYYCAKRWTAFDYWGQGTLVTVSSGGGGSGGGGS
GGGGSTDIQMTQSPSSLSASVGDRVTITCRASQSISSYLNWYQQKPGKAPKLLIYRASNL
QSGVPSRFSGSGSGTDFTLTISSLQPEDFATYYCQQSHPSPITFGQGTKVEIKRAAAHHHH
HHGAAEQKLXSEED Clone M34G:
(SEQ ID NO: 19)
CTATGCGNNNNATTCAGATCCTCTTCTGAGATGAGTTTTTGTTCTGCGGCCCC
GTGATGGTGATGATGATGTGCGGCCGCCCGTTTGATTTCCACCTTGGTCCCTTGGCC
GAACGTAGGAGGCGAAGTCTGAACCTGTTGACAGTAGTAAGTTGCAAAATCTTCAG
GTTGCAGACTGCTGATGGTGAGAGTGAAATCTGTCCCAGATCCACTGCCACTGAAC
CTTGATGGGACCCCACTTTGCAACAGGGATGCACGATAGATCAGGAGCTTAGGGGC
TTTCCCTGGTTTCTGCTGATACCAATTTAAATAGCTGCTAATGCTCTGGCTTGCCCGG
CAAGTGATGGTGACTCTGTCTCCTACAGATGCAGACAGGGAGGATGGAGACTGGGT
CATCTGGATGTCCGTCGACCCGCCACCGCCGCTGCCACCTCCGCCTGAACCGCCTCC
ACCGCTCGAGACGGTGACCAGGGTTCCCTGGCCCCAGTAGTCAAACTGCTTACCAC
GTTTCGCACAGTAATATACGGCCGTGTCCTCGGCTCTCAGGCTGTTCATTTGCAGAT
ACAGCGTGTTCTTGGAATTGTCTCTGGAGATGGTGAACCGGCCCTTCACGGAGTCTG

```
CGTAATGTGTCACAGTACCATCCGGCCAAATACCTGAGACCCACTCCAGCCCCTTCC

CTGGAGCCTGGCGGACCCAGCTCATGGCATAGCTGCTAAAGGTGAATCCAGAGGCT

GCACAGGAGAGTCTCAGGGACCCCCCAGGCTGTACCAAGCCTCCCCCAGACTCCAA

CAGCTGCACCTCGGCCATGGCCGGCTGGGCCGCGAGTAATAACAATCCAGCGGCTG

CCGTANGCAATAGGTATTTCATTATGACTGTCTCCTTGAAATAGAATTTGCATGCAA

GCTTGGCGTANTCATGGTCATAGCTGTTTCCTGTGNAAATTGTTATCCGCTCACNN

TTCCACNCAACATACGANCCGG
```

M34G AA sequence: (SEQ ID NO: 20)
```
MKYLLXTAAAGLLLLAAQPAMAEVQLLESGGGLVQPGGSLRLSCAASGFTFSS

YAMSWVRQAPGKGLEWVSGIWPDGTVTHYADSVKGRFTISRDNSKNTLYLQMNSLRA

EDTAVYYCAKRGKQFDWGQGTLVTVSSGGGGSGGGGSGGGGSTDIQMTQSPSSLSA

SVGDRVTITCRASQSISSYLNWYQQKPGKAPKWYRASLLQSGVPSRFSGSGSGTDFTL

TISSLQPEDFATYYCQQVQTSPPTFGQGTKVEIKRAAAHHHHHHGAAEQKLISEEDLNX

XHR
```

Clone M35A: (SEQ ID NO: 21)
```
CTANGCGNNNNNNNTCAGATCCTCTTCTGAGATGAGTTTTTGTTCTGCGGCCCC

GTGATGGTGATGATGATGTGCGGCCGCCCGTTTGATTTCCACCTTGGTCCCTTGGCC

GAACGTAGAAGGATTATCATCATTCTGTTGACAGTAGTAAGTTGCAAAATCTTCAG

GTTGCAGACTGCTGATGGTGAGAGTGAAATCTGTCCCAGATCCACTGCCACTGAAC

CTTGATGGGACCCCACTTTGCAAAGTGGATGCATCATAAATCAGGAGCTTAGGGGC

TTTCCCTGGTTTCTGCTGATACCAATTTAAATAGCTGCTAATGCTCTGACTTGCCCGG

CAAGTGATGGTGACTCTGTCTCCTACAGATGCAGACAGGGAGGATGGAGACTGGGT

CATCTGGATGTCCGTCGACCCGCCACCGCCGCTGCCACCTCCGCCTGAACCGCCTCC

ACCGCTCGAGACGGTGACCAGGGTTCCCTGGCCCCAGTAGTCAAAACCATTAGAAG

TTTTCGCACAGTAATATACGGCCGTGTCCTCGGCTCTCAGGCTGTTCATTTGCAGAT

ACAGCGTGTTCTTGGAATTGTCTCTGGAGATGGTGAACCGGCCCTTCACGGAGTCTG

CGTAATATGTAGTACTACCAGTAGCATCAATAGTTGAGACCCACTCCAGCCCCTTCC

CTGGAGCCTGGCGGACCCAGCTCATGGCATAGCTGCTAAAGGTGAATCCAGAGGCT

GCACAGGAGAGTCTCAGGGACCCCCCAGGCTGTACCAAGCCTCCCCCAGACTCCAA

CAGCTGCACCTCGGCCATGGCCGGCTGGGCCGCGAGTAATAACAATCCAGCGGCTG

CCGTNNNAATANGTATTTCATTATGACTGTCTCCTTGAAATAGAATTTGCATGCAAG

CTNGGNNTAATCATGGTCATAGCTGTTTCCTGTGTGAAATTGTTATCCGCTCACAAT

TCCACACAACATACG
```

M35A AA sequence: (SEQ ID NO: 22)
```
MQILFQGDSHNEIXIXTAAAGLLLLAAQPAMAEVQLLESGGGLVQPGGSLRLSC

AASGFTFSSYAMSWVRQAPGKGLEWVSTIDATGSTTYYADSVKGRFTISRDNSKNTLY

LQMNSLRAEDTAVYYCAKTSNGFDYWGQGTLVTVSSGGGGSGGGGSGGGGSTDIQMT

QSPSSLSASVGDRVTITCRASQSISSYLNWYQQKPGKAPKLLIYDASTLQSGVPSRFSGS

GSGTDFTLTISSLQPEDFATYYCQQNDDNPSTFGQGTKVEIKRAAAHRHHHHGAAEQK

LISEEDL
```

-continued

Clone M35F:
(SEQ ID NO: 23)
TTCAGATCCTCTTCTGAGANGAGTTTTTGTTCTGCGGCCCCGTGATGGTGATG

ANGATGTGCGGCCGCCCGTTTGATTTCCACCTTGGTCCCTTGGCCGAACGTAGTAGG

ACTAGCATAACTCTGTTGACAGTAGTAAGTTGCAAAATCTTCAGGTTGCAGACCGCT

GATGGTGAGAGTGAAATCTGTCCCAGATCCACTGCCACTGAACCTTGATGGGACCC

CACTTTGCAAAGAGGATGCACCATAGATCAGGAGCTTAGGGGCTTTCCCTGGTTTCT

GCTGATACCAATTTAAATAGCTGCTAATGCTCTGACTTGCCCGGCAAGTGATGGTGA

CTCTGTCTCCTACAGATGCAGACAGGGAGGATGGAGACTGGGTCATCTGGATGTCC

GTCGACCCGCCACCGCCGCTGCCACCTCCGCCTGAACCGCCTCCACCGCTCGAGAC

GGTGACCAGGGTTCCCTGGCCCCAGTAGTCAAAAGCAGTAGCAGTTTTCGCACAGT

AATATACGGCCGTGTCCTCGGCTCTCAGGCTGTTCATTTGCAGATACAGCGTGTTCT

TGGAATTGTCTCTGGAGATGGTGAACCGGCCCTTCACGGAGTCTGCGTAACTTGTAG

CATCACCATTAGAATAAATAGATGAGACCCACTCCAGCCCCTTCCCTGGAGCCTGG

CGGACCCAGCTCATGGCATAGCTGCTAAAGGTGAATCCAGAGGCTGCACAGGAGAG

TCTCAGGGACCCCCCAGGCTGTACCAAGCCTCCCCCAGACTCCAACAGCTGCACCTC

GGCCATGGCCGGCTGGGCCGCGAGTAATAACAATCCAGCGGCTGCCGTNNCAATAG

GTATTTCATTATGACTGTCTCCTTGAAATANAATTTGCATGCAAGCTTGGNGTAATC

ATGGNCATAGCTGTTTCCTGNGTGAAATTGTTATCCGCTCACNATTCCNCACNACAT

A

M35F AA sequence:
(SEQ ID NO: 24)
MQIXFQGDSHNEIPIXTAAAGLLLLAAQPAMAEVQLLESGGGLVQPGGSLRLSC

AASGFTFSSYAMSWVRQAPGKGLEWVSSIYSNGDATSYADSVKGRFTISRDNSKNTLY

LQMNSLRAEDTAVYYCAKTATAFDYWGQGTLVTVSSGGGGSGGGGSGGGGSTDIQM

TQSPSSLSASVGDRVTITCRASQSISSYLNWYQQKPGKAPKLLIYGASSLQSGVPSRFSGS

GSGTDFTLTISGLQPEDFATYYCQQSYASPTTFGQGTKVEIKRAAAHXHHHHGAAEQKL

XSEEDLK

Clone M35G:
(SEQ ID NO: 25)
CTATGCGNCCCCATTCAGATCCTCTTCTGAGANGAGTTTTTGTTCTGCGGCCC

CGTGATGGTGATGATGATGTGCGGCCGCCCGTTTGATTTCCACCTTGGTCCCTTGGC

CGAACGTAGGAGGCGAAGTCTGAACCTGTTGACAGTAGTAAGTTGCAAAATCTTCA

GGTTGCAGACTGCTGATGGTGAGAGTGAAATCTGTCCCAGATCCACTGCCACTGAA

CCTTGATGGGACCCCACTTTGCAACAGGGATGCACGATAGATCAGGAGCTTAGGGG

CTTTCCCTGGTTTCTGCTGATACCAATTTAAATAGCTGCTAATGCTCTGGCTTGCCCG

GCAAGTGATGGTGACTCTGTCTCCTACAGATGCAGACAGGGAGGATGGAGACTGGG

TCATCTGGATGTCCGTCGACCCGCCACCGCCGCTGCCACCTCCGCCTGAACCGCCTC

CACCGCTCGAGACGGTGACCAGGGTTCCCTGGCCCCAGTAGTCAAACTGCTTACCA

CGTTTCGCACAGTAATATACGGCCGTGTCCTCGGCTCTCAGGCTGTTCATTTGCAGA

TACAGCGTGTTCTTGGAATTGTCTCTGGAGATGGTGAACCGGCCCTTCACGGAGTCT

GCGTAATGTGTCACAGTACCATCCGGCCAAATACCTGAGACCCACTCCAGCCCCTTC

CCTGGAGCCTGGCGGACCCAGCTCATGGCATAGCTGCTAAAGGTGAATCCAGAGGC

```
TGCACAGGAGAGTCTCAGGGACCCCCCAGGCTGTACCAAGCCTCCCCCAGACTCCA

ACAGCTGCACCTCGGCCATGGCCGGCTGGGCCGCGAGTAATAACAATCCAGCGGCT

GCCGTANGCAATAGGTATTTCATTATGACTGTCTCCTTGAAATAGAATTTGCATGCA

AGCTTGGCGTAANCATGGTCATAGCTGTTTCCTGTGNGAAATTGTTATCCNGCTCAC

AATTCCNNCACAA
```

M35G AA sequence:
(SEQ ID NO: 26)
```
MKYLLXTAAAGLLLLAAQPAMAEVQLLESGGGLVQPGGSLRLSCAASGFTFSS

YAMSWVRQAPGKGLEWVSGIWPDGTVTHYADSVKGRFTISRDNSKNTLYLQMNSLRA

EDTAVYYCAKRGKQFDWGQGTLVTVSSGGGGSGGGGSGGGGSTDIQMTQSPSSLSA

SVGDRVTITCRASQSISSYLNWYQQKPGKAPKLLIYRASLLQSGVPSRFSGSGSGTDFTL

TISSLQPEDFATYYCQQVQTSPPTFGQGTKVEIKRAAAHHHHHHGAAEQKLXSEEDLNG

XA
```

Clone M58A:
(SEQ ID NO: 27)
```
TATGCGNNNATTCNGATCCTCTTCTGAGANGAGTTTTTGTTCTGCGGCCCCGT

GATGGTGATGATGNNNTGCGGCCGCCCGTTTGATTTCCACCTTGGTCCCTTGGCCGA

ACGTATTAGGACAATCAGTAGTCTGTTGACAGTAGTAAGTTGCAAAATCTTCAGGTT

GCAGACTGCTGATGGTGAGAGTGAAATCTGTCCCAGATCCACTGCCACTGAACCTT

GATGGGACCCCACTTTGCAAAGTGGATGCATTATAGATCAGGAGCTTAGGGGCTTT

CCCTGGTTTCTGCTGATACCAATTTAAATAGCTGCTAATGCTCTGACTTGCCCGGCA

AGTGATGGTGACTCTGTCTCCTACAGATGCAGACAGGGAGGATGGAGACTGGGTCA

TCTGGATGTCCGTCGACCCGCCACCGCCGCTGCCACCTCCGCCTGAACCGCCTCCAC

CGCTCGAGACGGTGACCAGGGTTCCCTGGCCCCAGTAGTCAAAATTAGCACCAGAT

TTCGCACAGTAATATACGGCCGTGTCCTCGGCTCTCAGGCTGTTCATTTGCAGATAC

AGCGTGTTCTTGGAATTGTCTCTGGAGATGGTGAACCTGCCCTTCACGGAGTCTGCG

TAAGATGTAGCATAACCACTAGCAGTAATACCTGAGACCCACTCCAGCCCCTTCCCT

GGAGCCTGGCGGACCCAGCTCATGGCATAGCTGCTAAAGGTGAATCCAGAGGCTGC

ACAGGAGAGTCTCANGGACCCCCAGGCTGTACCAAGCCTCCCCCAGACTCCAACA

GCTGCACCTCGGCCATGGCCGGCTGGGCCGCGAGTAATAACAATCCAGCGGCTGCC

GTANGCAATANGTATTTCATTATGACTGTCTCCTTGAAATAGAATTTGCATGCAAG

CTTGGNNTAATCATGGNNATAGCTGTTTCCTGTGTGAAATTGTTATCCGCTCACAAT

TNCNCAC
```

M58A AA sequence:
(SEQ ID NO: 28)
```
MIXPSLHAXFYFKETVIMKYXLXTAAAGLLLLAAQPAMAEVQLLESGGGLVQP

GGSXRLSCAASGFTFSSYAMSWVRQAPGKGLEWVSGITASGYATSYADSVKGRFTISR

DNSKNTLYLQMNSLRAEDTAVYYCAKSGANFDYWGQGTLVTVSSGGGGSGGGGSGG

GGSTDIQMTQSPSSLSASVGDRVTITCRASQSISSYLNWYQQKPGKAPKLLIYNASTLQS

GVPSRFSGSGSGTDFTLTISSLQPEDFATYYCQQTTDCPNTFGQGTKVEIKRAAAXHHH

HHGAAEQKLXSEEDXNXRI
```

Clone M58C:
(SEQ ID NO: 29)
```
GCGGCNNNTTCNGANCCTCTTCTGAGANGAGTTTTTGTTCTGCGGCCCCGTG

NNGGTGATGNNNNNGTGCGGCCGCCCGTTTGATTTCCACCTTGGTCCCTTGGCCGAA
```

-continued

```
CGTATTAGGGGTACTGTAACTCTGTTGACAGTAGTAAGTTGCAAAATCTTCAGGTTG

CAGACTGCTGATGGTGAGAGTGAAATCTGTCCCAGATCCACTGCCACTGAACCTTG

ATGGGACCCCACTTTGCAAACTGGATGCAGCATAGATCAGGAGCTTAGGGGCTTTC

CCTGGTTTCTGCTGATACCAATTTAAATAGCTGCTAATGCTCTGACTTGCCCGGCAA

GTGATGGTGACTCTGTCTCCTACAGATGCAGACAGGGAGGATGGAGACTGGGTCAT

CTGGATGTCCGTCGACCCGCCACCGCCGCTGCCACCTCCGCCTGAACCGCCTCCACC

GCTCGAGACGGTGACCAGGGTTCCCTGGCCCCAGTAGTCAAACGCCGGATGATATT

TCGCACAGTAATATACGGCCGTGTCCTCGGCTCTCAGGCTGTTCATTTGCAGATACA

GCGTGTTCTTGGAATTGTCTCTGGAGATGGTGAACCGGCCCTTCACGGNGTCTGCGT

ACTCTGTCGGCAGACCCTGCGGCGCAATCGATGAGACCCACTCCAGCCCCTTCCCTG

GAGCCTGGCGGACCCAGCTCATGGCATAGCTGCTAAAGGTGAATCCAGAGGCTGCA

CAGGAGAGTCTCAGGGACCCCCCAGGCTGTACCAAGCCTCCCCCAGACTCCAACAG

CTGCACCTCGGCCATGGCCGGCTGGGCCGCGAGTAATAACAATCCAGCGGCNGNCG

TANNCAATAGGTATTTCATTATGACTGTCTCCTTGAAATANNATTTGCATGCAAGCT

TGGNGTANTCATGGNCATAGCTGTTTNCTGNGTGNAAATTGTTATCCGCTCNNNAAT

TTCCAC
```

M58C AA sequence:

(SEQ ID NO: 30)
```
MKYLLXTXAAGLLLLAAQPAMAEVQLLESGGGLVQPGGSLRLSCAASGFTFSS

YAMSWVRQAPGKGLEWVSSIAPQGLPTEYADXVKGRFTISRDNSKNTLYLQMNSLRAE

DTAVYYCAKYHPAFDYWGQGTLVTVSSGGGGSGGGGSGGGGSTDIQMTQSPSSLSAS

VGDRVTITCRASQSISSYLNWYQQKPGKAPKLLIYAASSLQSGVPSRFSGSGSGTDFTLTI

SSLQPEDFATYYCQQSYSTPNTFGQGTKVEIKRAAAXXHHXHGAAEQKLXSEED
```

Clone M59F:

(SEQ ID NO: 31)
```
GCGNCCNNTTCAGATCCTCTTCTGAGATGAGTTTTTGTTCTGCGGCCCCGTGA

TGGTGATGANNNNNTGCGGCCGCCCGTTTGATTTCCACCTTGGTCCCTTGGCCGAAC

GTAGAAGGAGAATTACCAGTCTGTTGACAGTAGTAAGTTGCAAAATCTTCAGGTTG

CAGACTGCTGATGGTGAGAGTGAAATCTGTCCCAGATCCACTGCCACTGAACCTTG

ATGGGACCCCACTTTGCAAAGCGGATGCAGTATAGATCAGGAGCTTAGGGGCTTTC

CCTGGTTTCTGCTGATACCAATTTAAATAGCTGCTAATGCTCTGACTTGCCCGGCAA

GTGATGGTGACTCTGTCTCCTACAGATGCAGACAGGGAGGATGGAGACTGGGTCAT

CTGGATGTCCGTCGACCCGCCACCGCCGCTGCCACCTCCGCCTGAACCGCCTCCACC

GCTCGAGACGGTGACCAGGGTTCCCTGGCCCCAGTAGTCAAAAGTACTATAAGATT

TCGCACAGTAATATACGGCCGTGTCCTCGGCTCTCAGGCTGTTCATTTGCAGATACA

GCGTGTTCTTGGAATTGTCTCTGGAGATGGTGAACCGGCCCTTCACGGAGTCTGCGT

AAGCTGTACTAGCACTACTAGCAGCAATACCTGAGACCCACTCCAGCCCCTTCCCTG

GAGCCTGGCGGANCCAGCTCATGGCATAGCTGCTAAAGGTGAATCCAGAGGCTGCA

CAGGAGAGTCTCAGGGACCCCCCAGGCTGTACCAAGCCTCCCCCGGACTCCAACAG

CTGCACCTCGGCCATGGCCGGCTGGGCCGCGAGTAATAACAATCCAGCGGCTGCCG

TANGCAATANGTATTTCATTATGACTGTCTCCTTGAAATAGAATTTGCATGCAAGCT

TGGCGTANTCATGGNCATAGCTGNTTCCTGTGTGAAATTGNTNATCCGCTCAC
```

-continued

M59F AA sequence:
(SEQ ID NO: 32)
MKYXLXTAAAGLLLLAAQPAMAEVQLLESGGGLVQPGGSLRLSCAASGFTFSS

YAMSWXRQAPGKGLEWVSGIAASSASTAYADSVKGRFTISRDNSKNTLYLQMNSLRA

EDTAVYYCAKSYSTFDWGQGTLVTVSSGGGGSGGGGSGGGGSTDIQMTQSPSSLSAS

VGDRVTITCRASQSISSYLNWYQQKPGKAPKLLIYTASALQSGVPSRFSGSGSGTDFTLTI

SSLQPEDFATYYCQQTGNSPSTFGQGTKVEIKRAAAXXEMEHGAAEQKLISEEDL

Clone 4E1:
(SEQ ID NO: 33)
ATGGCCGAGGTGCAGCTGTCGGAGTCTGGGGGAGGCTTGGTACAGCCTGGG

GGGTCCCTGAGACTCTCCTGTGCAGCCTCTGGATTCACCTTTAGCAGCTATGCCATG

AGCTGGGTCCGCCAGGCTCCAGGGAAGGGGCTGGAGTGGGTCTCAGGTATTAATAG

TAATGGTACTTCTACATCTTACGCAGACTCCGTGAAGGGCCGGTTCACCATCTCCAG

AGACAATTCCAAGAACACGCTGTATCTGCAAATGAACAGCCTGAGAGCCGAGGACA

CGGCCGTATATTACTGTGCGAAATCTGCTTCTGATTTTGACTACTGGGGCCAGGGAA

CCCTGGTCACCGTCTCGAGCGGTGGAGGCGGTTCAGGCGGAGGTGGCAGCGGCGGT

GGCGGGTCGACGGACATCCAGATGACCCAGTCTCCATCCTCCCTGTCTGCATCTGTA

GGAGACAGAGTCACCATCACTTGCCGGGCAAGTCAGAGCATTAGCAGCTATTTAAA

TTGGTATCAGCAGAAACCAGGGAAAGCCCCTAAGCTCCTGATCTATAATGCATCCA

CTTTGCAAAGTGGGGTCCCATCAAGGTTCAGTGGCAGTGGATCTGGGACAGATTTC

ACTCTCACCATCAGCAGTCTGCAACCTGAAGATTTTGCAACTTACTACTGTCAACAG

AATACTTATAGTCCTACTACGTTC

4E1 AA sequence:
(SEQ ID NO: 34)
MKYLLPTNAAGLLLLAANPAMAEVQLSESGGGLVQPGGSLRLSCAASGFTFSSY

AMSWVRQAPGKGLEWVSGINSNGTSTSYADSVKGRFTISRDNSKNTLYLQMNSLRAED

TAVYYCAKSASDFDYWGQGTLVTVSSGGGGSGGGGSGGGGSTDIQMTQSPSSLSASVG

DRVTITCRASQSISSYLNWYQQKPGKAPKWLLIYNASTLQSGVPSRFSGSGSGTDFTLTISS

LQPEDFATYYCQQNTYSPTTFGNNNKVEIKRAA

Clone 4H3:
(SEQ ID NO: 35)
ATGGCCGAGATGCAGCTGTTGGAGTCTGGGGGAGGCTTGGTACAGCCTGGG

GGGTCCCTGAGACTCTCCTGTGCAGCCTCTGGATTCACCTTTAGCAGCTATGCCATG

AGCTGGGTCCGCCAGGCTCCAGGGAAGGGGCTGGAGTGGGTCTCATATATTACTGC

TAATGGTGATAGTACAACTTACGCAGACTCCGTGAAGGGCCGGTTCACCATCTCCA

GAGACAATTCCAAGAACACGCTGTATCTGCAAATGAACAGCCTGAGAGCCGAGGAC

ACGGCCGTATATTACTGTGCGAAAAGTACTACTGATTTTGACTACTGGGGCCAGGG

AACCCTGGTCACCGTCTCGAGCGGTGGAGGCGGTTCAGGCGGAGGTGGCAGCGGCG

GTGGCGGGTCGACGGACATCCAGATGACCCAGTCTCCATCCTCCCTGTCTGCATCTG

TAGGAGACAGAGTCACCATCACTTGCCGGGCAAGTCAGAGCATTAGCAGCTATTTA

AATTGGTATCAGCAGAAACCAGGGAAAGCCCCTAAGCTCCTGATCTATAGTGCATC

CAATTTGCAAAGTGGGGTCCCATCAAGGTTCAGTGGCAGTGGATCTGGGACAGATT

TCACTCTCACCATCAGCAGTCTGCAACCTGAAGATTTTGCAACTTACTACTGTCAAC

AGACTTCTTATAGTCCTTCTACGTTCGGCCAAGGGNCCAAGGTGGAAATCAAACGG

GCGGCC

-continued

4H3 AA Sequence:
(SEQ ID NO: 36)
MAEMQLLESGGGLVQPGGSLRLSCAASGFTFSSYAMSWVRQAPGKGLEWVSYI

TANGDSTTYADSVKGRFTISRDNSKNTLYLQMNSLRAEDTAVYYCAKSTTDFDYWGQ

GTLVTVSSGGGGSGGGGSGGGGSTDIQMTQSPSSLSASVGDRVTITCRASQSISSYLNW

YQQKPGKAPKLLIYSASNLQSGVPSRFSGSGSGTDFTLTISSLQPEDFATYYCQQTSYSPS

TFGQGXKVEIKRAAA

Clone 1A5:
(SEQ ID NO: 37)
ATGGCCGAGGTGCAGCTGTTGGAGTCTGGGGGAGGCTTGGTACAGCCTGGG

GGNTCCCTGAGACTCTCCTGTGCAGCCTCTGGATTCACCTTTAGCAGCTATGCCATG

AGCTGGGTCCGCCAGGCTCCAGGGAAGGGGCTGGAGTGGGTCTCAACTATTAATGC

TAGTGGTGGTAGTACAGGTTACGCAGACTCCGTGAAGGGCCGGTTCACCATCTCCA

GAGACAATTCCAAGAACACGCTGTATCTGCAAATGAACAGCCTGAGAGCCGAGGAC

ACGGCCGTATATTACTGTGCGAAAGCTGATGCTTATTTTGACTACTGGGGCCAGGGA

ACCCTGGTCACCGTCTCGAGCGGTGGAGGCGGTTCAGGCGGAGGTGGCAGCGGCGG

TGGCGGGTCGACGGACATCCAGATGACCCAGTCTCCATCCTCCCTGTCTGCATCTGT

AGGAGACAGAGTCACCATCACTTGCCGGGCAAGTCAGAGCATTAGCAGCTATTTAA

ATTGGTATCAGCAGAAACCAGGGAAAGCCCCTAAGCTCCTGATCTATTCTGCATCCT

CGTTGCAAAGTGGGGTCCCATCAAGGTTCAGTGGCAGTGGATCTGGGACAGATTTC

ACTCTCACCATCAGCAGTCTGCAACCTGAAGATTTTGCAACTTACTACTGTCAACAG

GATGCTAGTGGTCCTTCTACGTTCGGCCAAGGGACCAAGGTGGAAATCAAACGGGC

GGCCGCA

1A5 AA Sequence:
(SEQ ID NO: 38)
MAEVQLLESGGGLVQPGGSLRLSCAASGFTFSSYAMSWVRQAPGKGLEWVSTI

NASGGSTGYADSVKGRFTISRDNSKNTLYLQMNSLRAEDTAVYYCAKADAYFDYWGQ

GTLVTVSSGGGGSGGGGSGGGGSTDIQMTQSPSSLSASVGDRVTITCRASQSISSYLNW

YQQKPGKAPKLLIYSASSLQSGVPSRFSGSGSGTDFTLTISSLQPEDFATYYCQQDASGPS

TFGQGTKVEIKRAA

Clone 3D3:
(SEQ ID NO: 39)
ATGGCCGAGGTGCAGCTGTTGGAGTCTGGGGGAGGCTTGGTACAGCCTGGG

GGGTCCCTGAGACTCTCCTGTGCAGCCTCTGGATTCACCTTTAGCAGCTATGCCATG

AGCTGGGTCCGCCAGGCTCCAGGGAAGGGGCTGGAGTGGGTCTCATATATTGCTGA

TGATGGTGCTAATACAGCTTACGCAGACTCCGTGAAGGGCCGGTTCACCATCTCCA

GAGACAATTCCAAGAACACGCTGTATCTGCAAATGAACAGCCTGAGAGCCGAGGAC

ACGGCCGTATATTACTGTGCGAAAAATAATGATGGTTTTGACTACTGGGGCCAGGG

AACCCTGGTCACCGTCTCGAGCGGTGGAGGCGGTTCAGGCGGAGGTGGCAGCGGCG

GTGGCGGGTCGACGAACATCCAGATGACCCAGTCTCCATCCTCCCTGTCTGCATCTG

TAGGAGACAGAGTCACCATCACTTGCCGGGCAAGTCAGAGCATTAGCAGCTATTTA

AATTGGTATCAGCAGAAACCAGGGAAAGCCCCTAAGCTCCTGATCTATTCTGCATC

CACTTTGCAAAGTGGGGTCCCATCAAGGTTCAGTGGCAGTGGATCTGGGACAGATT

TCACTCTCACCATCAGCAGTCTGCAACCTGAAGATTTTGCAACTTACTACTGTCAAC

-continued

```
AGGCTGCTACTAGTCCTTCTACGTTCGGCCAAGGGNCCAAGGTGGAAATCAAACGG

GCGGNCGCAC
```

3D3 AA Sequence:

(SEQ ID NO: 40)
```
MAEVQLLESGGGLVQPGGSLRLSCAASGFTFSSYAMSWVRQAPGKGLEWVSYI

ADDGANTAYADSVKGRFTISRDNSKNTLYLQMNSLRAEDTAVYYCAKNNDGFDYWG

QGTLVTVSSGGGGSGGGGSGGGGSTNIQMTQSPSSLSASVGDRVTITCRASQSISSYLN

WYQQKPGKAPKLLIYSASTLQSGVPSRFSGSGSGTDFTLTISSLQPEDFATYYCQQAATS

PSTFGQGXKVEIKRAXA
```

The following TBI Clone Sequences were identified:
Clone T2B:

(SEQ ID NO: 41)
```
TTCAAGGAGACAGTCATAATGAAATANCCTATTGCNTACGGCANNCGCTGGA

TTGTTATTACTCGCGGCCCAGCCNGNCCATGGCCGAGGTGCAGCTGTTGGAGTCTGG

GGGAGGCTTGGTACAGCCTGGGGGGTCCCTGAGACTCTCCTGTGCAGCCTCTGGATT

CACCTTTAGCAGCTATGCCATGAGCTGGGTCCGCCAGGCTCCAGGGAAGGGGCTGG

AGTGGGTCTCAAATATTAGTTCTGATGGTGATTCTACAGCTTACGCAGACTCCGTGA

AGGGCCGGTTCACCATCTCCAGAGACAATTCCAAGAACACGCTGTATCTGCAAATG

AACAGCCTGAGAGCCGAGGACACGGCCGTATATTACTGTGCGAAAGCTTCTAGTAA

TTTTGACTACTGGGGCCAGGGAACCCTGGTCACCGTCTCGAGCGGTGGAGGCGGTT

CAGGCGGAGGTGGCAGCGGCGGTGGCGGGTCGACGGACATCCAGATGACCCAGTC

TCCATCCTCCCTGTCTGCATCTGTAGGAGACAGAGTCACCATCACTTGCCGGGCAAG

TCAGAGCATTAGCAGCTATTTAAATTGGTATCAGCAGAAACCAGGGAAAGCCCCTA

AGCTCCTGATCTATGCTGCATCCAATTTGCAAAGTGGGGTCCCATCAAGGTTCAGTG

GCAGTGGATCTGGGACAGATTTCACTCTCACCATCAGCAGTCTGCAACCTGAAGATT

TTGCAACTTACTACTGTCAACAGTCTAATTCTGATCCTACTACGTTCGGCCAAGGGA

CCAAGGTAATCAAACGGGCGGCCGCACATCATCATCACCATCACGGGGCCGCAGAA

CAAAAACTCNTCTCAGAAGAGGATCTGAATGGNNCCGCATAGNC
```

T2B AA sequence:

(SEQ ID NO: 42)
```
MAEVQLLESGGGLVQPGGSLRLSCAASGFTFSSYAMSWVRQAPGKGLEWVSNI

SSDGDSTAYADSVKGRFTISRDNSKNTLYLQMNSLRAEDTAVYYCAKASSNFDYWGQ

GTLVTVSSGGGGSGGGGSGGGGSTDIQMTQSPSSLSASVGDRVTITCRASQSISSYLNW

YQQKPGKAPKLLIYAASNLQSGVPSRFSGSGSGTDFTLTISSLQPEDFATYYCQQSNSDP

TTFGQGTKVIKRAAAHHHHHHGAAEQKLXSEEDLNXXA
```

Clone T1H:

(SEQ ID NO: 43)
```
CAGGGGGGGCGGNGCCTATGNAAAAAACGCCAGCAACGCGGCCTTTTACGG

TTCCTGGCCCTTTGCTGGCCTTTTGCTCACATGTTCTTTCCTGCGTTATCCCCTGATTC

TGTGGATAACCGTATTACCGCCTTTGAGTGAGCTGATACCGCTCGCCGCAGCCGAAC

GACCGAGCGCAGCGAGTCAGTGAGCGAGGAAGCGGAAGAGCGCCCAATACGCAAA

CCGCCTCTCCCCGCGCGTTGGCCGATTCATTAATGCAGCTGGCACGACAGGTTTCCC

GACTGGAAAGCGGGCAGTGAGCGCAACGCAATTAATGTGAGTTAGCTCACTCATTA

GGCACCCCAGGCTTTACACTTTATGCTCCCGGCTCGTATGTTGTGTGGAATTGTGAG

CGGATAACAATTTCACACAGGAAACAGCTATGACCATGATTACGCCAAGCTTGCAT
```

-continued

```
GCAAATTCTATTTCAAGGAGACAGTCATAGCTAGCATGAAAAAGATTTGGCTGGCG

CTGGCTGGTTTAGTTTTAGCGTTTAGCGCATCGGCGGACTACAAAGAGGCCCAGCC

GGCCATGGACCTGGGTAAGAAACTGCTGGAAGCTGCTCGTGCTGGTCAGGACGACG

AAGTTCGTATCCTGATGGCTAACGGTGCTGACGTTAACGCTCATGACGAACAGGGT

ACTACTCCGCTGCACCTGGCTGCTAAAGAAGGTCACCTGGAAATCGTTGAAGTTCTG

CTGAAGTACGGTGCTGACGTTAACGCTCAGGACAAATTCGGTAAGACCGCTTTCGA

CATCTCCATCGACAACGGTAACGAGGACCTGGCTGAAATCCTGCAAGCGGCCGCAC

ATCATCATCACCATCACGGGGCCGCAGAACAAAAACTCATCTCAGAAGAGGATCTG

AATGGCCGCNTA
```

T1H AA sequence:
(SEQ ID NO: 44)
```
MLPARMLCGIVSGQFHTGNSYDHDYAKLACKFYFKETVIASMKKIWLALAGLV

LAFSASADYKEAQPAMDLGKKLLEAARAGQDDEVRILMANGADVNAHDEQGTTPLHL

AAKEGHLEIVEVLLKYGADVNAQDKFGKTAFDISIDNGNEDLAEILQAAAHHHHHHGA

AEQKLISEEDLNGRX
```

Clone T3F:
(SEQ ID NO: 45)
```
GAGCTATGAGANNNNNNCCACGCTTCCCCNAAGGGAGAAAGGCGGACAGGT

ATCCCGGTAAGCNGGCAGGGTCGGAACAGGAGAGCGCACGAGGGAGNNTNCAGGG

GGAAACGCCTGGTATCTTTATAGTCCTGTCGGNNTTTCGCCACCTCTGACTTGAGCG

TCGATTTTTTGTGATGCTCGTCAGGGGGGCGGAGCCTATGGAAAAACGCCAGCAAC

GCGGCCTTTTTACGGTTCCTGGCCTTTTGCTGGCCTTTTGCTCACATGTTCTTTCCTG

CGTTATCCCCTGATTCTGTGGATAACCGTATTACCGCCTTTGAGTGAGCTGATACCG

CTCGCCGCAGCCGAACGACCGAGCGCAGCGAGTCAGTGAGCGAGGAAGCGGAAGA

GCGCCCAATACGCAAACCGCCTCTCCCCGCGCGTTGGCCGATTCATTAATGCAGCTG

GCACGACAGGTTTCCCGACTGGAAAGCGGGCAGTGAGCGCAACGCAATTAATGTGA

GTTAGCTCACTCATTAGGCACCCCAGGCTTTACACTTTATGCTCCCGGCTCGTATGTT

GTGTGGAATTGTGAGCGGATAACAATTTCACACAGGAAACAGCTATGACCATGATT

ACGCCAAGCTTGCATGCAAATTCTATTTCAAGGAGACAGTCATAGCTAGCATGAAA

AAGATTTGGCTGGCGCTGGCTGGTTTAGTTTTAGCGTTTAGCGCATCGGCGGACTAC

AAAGAGGCCCAGCCGGCCATGGTAGGAAGACCTGACGTTAACGCTCAGGACAAATT

CGGTAAGACCGCTTTCGACATCTCCATCGACAACGGTAACGAGGACCTGGCTGAAA

TCCTGCAAGCGGCCGCACatCaTCATCACCATCACGGGGCCGCAGAACAAAAACTCN

TCTCAGAAGAGGATCNGAANNNNNCGCNTAGA
```

T3F AA sequence:
(SEQ ID NO: 46)
```
MFFPALSPDSVDNRITAFEADTARRSRTTERSESVSEEAEEERPIRKPPLPARWPIHC

SWHDRFPDWKAGSERNAINVSLTHAPQALHFMLPARMLCGIVSGQFHTGNSYDHDYA

KLACKFYFKETVIASMKKIWLALAGLVLAFSASADYKEAQPAMVGRPDVNAQDKFGK

TAFDISIDNGNEDLAEILQAAAHHHHHHGAAEQKLXSEED
```

Clone T3G:
(SEQ ID NO: 47)
```
TCGTCAGGGGGGNCGGNAGCCTATGGAAAAAACGNNAGCAACGNGNCNTTT

TTACGGNNNNTGGCCTTTTGCTGGCNTTTGCTCACATGTTCTTTCCTGCGTTNNCCCC

TGATTCTGTGGATANCCGTATTACCGCCTTTNGAGTGAGCTGATACCGNTCGCCGCA
```

-continued

```
GCCGAACGACCGAGCGCAGCGAGTCAGTGAGCGAGGAAGCGGAAGAGCGCCCAAT

ACGCAAACCGCCTCTCCCCGCGCGTTGGCCGATTCATTAATGCAGCTGGCACGACA

GGTTTCCCGACTGGAAAGCGGGCAGTGAGCGCAACGCAATTAATGTGAGTTAGCTC

ACTCATTAGGCACCCCAGGCTTTACACTTTATGCTCCCGGCTCGTATGTTGTGTGGA

ATTGTGAGCGGATAACAATTTCACACAGGAAACAGCTATGACCATGATTACGCCAA

GCTTGCATGCAAATTCTATTTCAAGGAGACAGTCATAGCTAGCATGAAAAAGATTT

GGCTGGCGCTGGCTGGTTTAGTTTTAGCGTTTAGCGCATCGGCGGACTACAAAGAG

GCCCAGCCGGCCATGGACCTGGGTAAGAAACTGCTGGAAGCTGCTCGTGCTGGTCA

GGACGACGAAGTTCGTATCCTGATGGCTAACGGTGCTGACGTTAACGCTTGGGACA

TGACTGGTCATACTCCGCTGCACCTGGCTGCTCAGTTCGGTCACCTGGAAATCGTTG

AAGTTCTGCTGAAGCACGGTGCTGACGTTAACGCTCAGGACAAATTCGGTAAGACC

GCTTTCGACATCTCCATCGACAACGGTAACGAGGACCTGGCTGAAATCCTGCAAGC

GGCCGCACatcatCATCACCATCACGGGGcCGCAGAACAAAAAcTCaTcTCAGAAGAGG

ATNNGAANGNNNCCGCA
```

T3G AA sequence:

(SEQ ID NO: 48)
```
MLPARMLCGIVSGQFHTGNSYDHDYAKLACKFYFKETVIASMKKIWLALAGLV

LAFSASADYKEAQPAMDLGKKLLEAARAGQDDEVRILMANGADVNAWDMTGHTPLH

LAAQFGHLEIVEVLLKHGADVNAQDKFGKTAFDISIDNGNEDLAEILQAAAHHHHHG

AAEQKLISEED
```

Clone T1A:

(SEQ ID NO: 49)
```
TTTATAGTNCNTGTCGGGTTTCNCCACNTNTGACNTGAGCNTCGATNTTTNNN

NTGCTCNNCAGGGGGGCGGAGCCTATGGAAAAACGNCAGCAACGCGNCNTTTNTN

CGGTTNNTGNCNTTTTGCTGGCCTTTTGCTCACATGTTCTTTCNTGCGTTATCCCNTG

ATTNTGTGGATANCCGTATTACCGCCTTTGAGTGAGCTGATACCGCTCGCCGCANNC

GAACGACCGAGCGCAGNGAGTCAGTGAGCGAGGAAGCGGAAGAGCGCCCAATACG

CAAACCGCCTCTCNCCGCGCGTTGGCCGATTCATTAATGCAGCTGGCACGACAGGTT

TNNNGACTGGAAAGCGGGCAGTGAGCGCAACGCAATTAATGTGAGTTAGCTCACTC

ATTAGGCACCCCAGGCTTTACACTTTATGCTCCCGGCTCGTATGTTGTGTGGAATTG

TGAGCGGATAACAATTTCACACAGGAAACAGNTATGACCATGATTACGCCAAGCTT

GCATGCAAATTCTATTTCAAGGAGACAGTCATAGCTAGCATGAAAAAGATTTGGCT

GGCGCTGGCTGGTTTAGTTTTAGCGTTTAGCGCATCGGCGGANTACAAAGAGGCCC

AGCCGGCCATGGGCGGAACCAGCAGTTTNTTACCCAGGTCCATGGACCTGGGTCAC

CTGGAAATCGTTGAAGTTCTGCTGAAGTACGGTGNTGACGTTAACGNTCAGGACAA

ATTCGGTAAGACCGCTTTCGACATNTCCATCGACAACGGTAACGAGGACCTGGCTG

AAATCCTGCAAGCGGCCGCACATCATCATCACCATCATCGGGCTCGCAGAACAAAA

ATCATCTC
```

T1A AA sequence:

(SEQ ID NO: 50)
```
MFFXALSXDXVDXRITAFEADTARRXRTTERXESVSEEAEERPIRKPPLXARWPI

HCSWHDRFXDWKAGSERNAINVSLTHAPQALHFMLPARMLCGIVSGQFHTGNXYDHD

YAKLACKFYFKETVIASMKKIWLALAGLVLAFSASAXYKEAQPAMGGTSSXLPRSMDL
```

-continued
GHLEIVEVLLKYGXDVNXQDKFGKTAFDXSIDNGNEDLAEILQAAAHHHHHRARRT

KII

Clone T1D:
(SEQ ID NO: 51)
GAGCCTATGGAAAAAACGCCCAGCAACGCGGCNTTTTTACGGTTCCTGGCCT

TTTGCTNGNCNTTTTGNTCACATGTTCTTTCCTGCGTTATCCCCTGATTCTGTGGATA

ACCGTATTACCGCCTTTGAGTGNNNNGATACCGCTCGCCGCAGCCGAACGACCGAG

CGCAGCGAGTCAGTGAGCGAGGAAGCGGAAGAGCGCCCAATACGCAAACCGCCTC

TCCCCGCGCGTTGGCCGATTCATTAATGCAGCTGGCACGACAGGTTTCCCGACTGGA

AAGCGGGCAGTGAGCGCAACGCAATTAATGTGAGTTAGCTCACTCATTAGGCACCC

CAGGCTTTACACTTTATGCTCCCGGCTCGTATGTTGTGTGGAATTGTGAGCGGATAA

CAATTTCACACAGGAAACAGCTATGACCATGATTACGCCAAGCTTGCATGCAAATT

CTATTTCAAGGAGACAGTCATAGCTAGCATGAAAAAGATTTGGCTGGCGCTGGCTG

GTTTAGTTTTAGCGTTTAGCGCATCGGCGGACTACAAAGAGGCCCAGCCGGCCATG

GACCTGGGTAAGAAACTGCTGGAAGCTGCTCGTGCTGGTCAGGACGACGAAGTTCG

TATCCTGATGGCTAACGGTGCTGACGTTAACGCTGACGACTTCTCTGGTACTACTCC

GCTGCACCTGGCTGCTCATCATGGTCACCTGGAAATCGTTGAAGTTCTGCTGAAGTA

CGGTGCTGACGTTAACGCTCAGGACAAATTCGGTAAGACCGCTTTCGACATCTCCAT

CGACAACGGTAACGAGGACCTGGCTGAAATCCTGCAAGCGGCCGCANNNNNNCAT

CACCATCACGGGGCCGCAGAACAAAAACTCNNNCAGAAGAGGATNNGAANNNNCG

CATA

T1D AA sequence:
(SEQ ID NO: 52)
MFFPALSPDSVDNRITAFEXXDTARRSRTTERSESVSEEAEERPIRKPPLPARWPI

HCSWHDRFPDWKAGSERNAINVSLTHAPQALHFMLPARMLCGIVSGQFHTGNSYDHD

YAKLACKFYFKETVIASMKKIWLALAGLVLAFSASADYKEAQPAMDLGKKLLEAARA

GQDDEVRILMANGADVNADDFSGTTPLHLAAHHGHLEIVEVLLKYGADVNAQDKFGK

TAFDISIDNGNEDLAEILQAAAXXHHHHGAAEQKLX

Clone T2C:
(SEQ ID NO: 53)
GANGNTCNNCAGGGGGGCGGAGCCTATNGAAAAAACGCCAGCAACGCGG

CNTTTTTTACGGTTCCTGGCCTTTTGCTGGCCTTTTGCTCACATGTTCTTTCCTGCGTT

ATCCCCTGATTCTGTGGATANCCGTATTACCGCCTTTGAGTGAGCTGATACCGCTCG

CCGCAGCCGAACGACCGAGCGCAGCGAGTCAGTGAGCGAGGAAGCGGAAGAGCGC

CCAATACGCAAACCGCCTCTCCCCGCGCGTTGGCCGATTCATTAATGCAGCTGGCAC

GACAGGTTTCCCGACTGGAAAGCGGGCAGTGAGCGCAACGCAATTAATGTGAGTTA

GCTCACTCATTAGGCACCCCAGGCTTTACACTTTATGCTCCCGGCTCGTATGTTGTGT

GGAATTGTGAGCGGATAACAATTTCACACAGGAAACAGCTATGACCATGATTACGC

CAAGCTTGCATGCAAATTCTATTTCAAGGAGACAGTCATAGCTAGCATGAAAAAGA

TTTGGCTGGCGCTGGCTGGTTTAGTTTTAGCGTTTAGCGCATCGGCGGACTACAAAG

AGGCCCAGCCGGCCATGGACCTGGGTAAGAAACTGCTGGAAGCTGCTCGTGCTGGT

CAGGACGACGAAGTTCGTATCCTGATGGCTAACGGTGCTGACGTTAACGCTCTGGA

CGAAGTTGGTTCTACTCCGCTGCACCTGGCTGCTATGGCTGGTCACCTGGAAATCGT

TGAAGTGCTGAAGCACGGTGCTGACGTTAACGCTCAGGACAAATTCGGTAAGACCG

-continued

```
CTTTCGACATCTCCATCGACAACGGTAACGAGGACCTGGCTGAAATCCTGCAAGCG

GCCGCACATCATCATCACCATCACGGGGCCGCAGAACAAAAACTCATCTCAGAAGA

GGATCTGAATGNNNCGCNTAG
```

T2C AA sequence:
(SEQ ID NO: 54)
```
MLPARMLCGIVSGQFHTGNSYDHDYAKLACKFYFKETVIASMKKIWLALAGLV

LAFSASADYKEAQPAMDLGKKLLEAARAGQDDEVRILMANGADVNALDEVGSTPLHL

AAMAGHLEIVEVLKHGADVNAQDKFGKTAFDISIDNGNEDLAEILQAAAHHHHHHGA

AEQKLISEED
```

Clone T2F:
(SEQ ID NO: 55)
```
GGACAGGNTATCCGGTAAAGCGGCAGGGTCGGANCANNAGAGCGCACGAG

GGAGCTTNNCAGGGGGAAACGCCTGGTATCTTTATAGTCCTGTCGGNTTTCGCCCAC

CTCTGACTTGAGCGTCGATTTTTGTGATGCTCGTCAGGGGGGCGGAGCCTATGGAA

AAACGCCAGCAACGCGGCCTTTTTACGGTTCCTGGCCTTTTGCTGGCCTTTTGCTCA

CATGTTCTTTCCTGCGTTATCCCCTGATTCTGTGGATAACCGTATTACCGCCTTTGAG

TGAGCTGATACCGCTCGCCGCAGCCGAACGACCGAGCGCAGCGAGTCAGTGAGCGA

GGAAGCGGAAGAGCGCCCAATACGCAAACCGCCTCTCCCCGCGCGTTGGCCGATTC

ATTAATGCAGCTGGCACGACAGGTTTCCCGACTGGAAAGCGGGCAGTGAGCGCAAC

GCAATTAATGTGAGTTAGCTCACTCATTAGGCACCCCAGGCTTTACACTTTATGCTC

CCGGCTCGTATGTTGTGTGGAATTGTGAGCGGATAACAATTTCACACAGGAAACAG

CTATGACCATGATTACGCCAAGCTTGCATGCAAATTCTATTTCAAGGAGACAGTCAT

AGCTAGCATGAAAAAGATTTGGCTGGCGCTGGCTGGTTTAGTTTTAGCGTTTAGCGC

ATCGGCGGACTACAAAGAGGCCCAGCCGGCCATGGACCTGGCTGCTCATGTTGGTC

ACCTGGAAATCGTTGAAGTTCTGCTGAAGTACGGTGCTGACGTTAACGCTCAGGAC

AAATTCGGTAAGACCGCTTTCGACATCTCCATCGACAACGGTAACGAGGACCTGGC

TGAAATCCTGCAAGCGGCcgCACatCaTCATCACCATCACGGGGCCGCAGAACAAAA

CTCaTCTCAGAAGAGGATCTGANNNNNCGCNTAG
```

T2F AA sequence:
(SEQ ID NO: 56)
```
MFFPALSPDSVDNRITAFEADTARRSRTTERSESVSEEAEERPIRKPPLPARWPIHC

SWHDRFPDWKAGSERNAINVSLTHAPQALHFMLPARMLCGIVSGQFHTGNSYDHDYA

KLACKFYFKETVIASMKKIWLALAGLVLAFSASADYKEAQPAMDLAAHVGHLEIVEVL

LKYGADVNAQDKFGKTAFDISIDNGNEDLAEILQAAAHHHHHHGAAEQKLISEEDL
```

A "variant" of an amino acid sequence described herein, or a nucleic acid sequence encoding such an amino acid sequence, is a sequence that is substantially similar to SEQ ID NO:1-56. Variant amino acid and nucleic acid sequences include synthetically derived amino acid and nucleic acid sequences, or recombinantly derived amino acid or nucleic acid sequences. Generally, amino acid or nucleic acid sequence variants of the invention will have at least 40, 50, 60, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to SEQ ID NO: 1-56. The present invention includes variants of the amino acid sequences of the antibodies and antibody fragments described herein, as well as variants of the nucleic acid sequences encoding such amino acid sequences (i.e., SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55 or SEQ ID NO:56).

"Variants" are intended to include sequences derived by deletion (so-called truncation) or addition of one or more amino acids to the N-terminal and/or C-terminal end, and/or addition of one or more bases to the 5' or 3' end of the nucleic acid sequence; deletion or addition of one or more amino acids/nucleic acids at one or more sites in the sequence; or substitution of one or more amino acids/nucleic acids at one or more sites in the sequence. The amino acids described herein may be altered in various ways including amino acid substitutions, deletions, truncations, and insertions. Methods for such manipulations are generally known in the art. For example, amino acid sequence variants can be prepared by mutations in the DNA. Methods for mutagenesis and nucleotide sequence alterations are well known in the art. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall protein retains its spatial conformation but does not alter its biological activity. For example, common conserved changes might be Asp to Glu, Asn or Gln; His to Lys, Arg or Phe; Asn to Gln, Asp or Glu and Ser to Cys, Thr or Gly. Alanine is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art.

Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

Nucleic Acids and Vectors

In certain embodiments, the present invention provides a nucleic acid encoding the amino acids described herein.

In certain embodiments, the present invention provides a vector comprising the nucleic acid described herein.

In certain embodiments, the present invention provides a phage comprising the vector described herein.

As used herein, the term "nucleic acid" and "polynucleotide" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" may also be used interchangeably with gene, cDNA, DNA and RNA encoded by a gene, e.g., genomic DNA, and even synthetic DNA sequences. The term also includes sequences that include any of the known base analogs of DNA and RNA.

By "fragment" or "portion" is meant a full length or less than full length of the nucleotide sequence.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have in at least one embodiment 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

As used herein, "sequence identity" or "identity" in the context of two nucleic acid sequences makes reference to a specified percentage of residues in the two sequences that are the same when aligned by sequence comparison algorithms or by visual inspection.

As used herein, "percentage of sequence identity" means the value determined by comparing two optimally aligned sequences, wherein the portion of the polynucleotide sequence may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70%, 71%, 72%, 73%, 74%, 75%, 76%, 77%, 78%, or 79%; at least 80%, 81%, 82%, 83%, 84%, 85%, 86%, 87%, 88%, or 89%; at least 90%, 91%, 92%, 93%, or 94%; or even at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code.

As noted above, another indication that two nucleic acid sequences are substantially identical is that the two molecules hybridize to each other under stringent conditions. The phrase "hybridizing preferentially to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched nucleic acid. Specificity is typically the function of post-hybridization washes, the critical factors being the ionic strength and temperature of the final wash solution. For DNA-DNA hybrids, the $T_m$ can be approximated from the equation of Meinkoth and Wahl: $T_m$ 81.5° C. +16.6 (log M)+0.41 (%GC)−0.61 (% form)−500/L. M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2× SSC wash at 65° C. for 15 minutes. Often, a high stringency wash is preceded by a low stringency wash to remove background probe signal. An example medium stringency wash for a duplex of, e.g., more than 100 nucleotides, is 1× SSC at 45° C. for 15 minutes. An example low stringency wash for a duplex of, e.g., more than 100 nucleotides, is 4-6× SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1× SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2× SSC (20× SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1× SSC at 55 to 60° C. "Operably-linked" nucleic acids refers to the association of nucleic acid sequences on single nucleic acid fragment so that the function of one is affected by the other, e.g., an arrangement of elements wherein the components so described are configured so as to perform their usual function. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or anti sense orientation. Control elements operably linked to a coding sequence are capable of effecting the expression of the coding sequence. The control elements need not be contiguous with the coding sequence, so long as they function to direct the expression thereof.

Thus, for example, intervening untranslated yet transcribed sequences can be present between a promoter and the coding sequence and the promoter can still be considered "operably linked" to the coding sequence.

The terms "isolated and/or purified" refer to in vitro isolation of a nucleic acid, e.g., a DNA or RNA molecule from its natural cellular environment, and from association with other components of the cell or test solution (e.g. RNA pool), such as nucleic acid or polypeptide, so that it can be sequenced, replicated, and/or expressed. For example, "isolated nucleic acid" may be a DNA molecule containing less than 31 sequential nucleotides that is transcribed into an RNAi molecule. Such an isolated RNAi molecule may, for example, form a hairpin structure with a duplex 21 base pairs in length that is complementary or hybridizes to a sequence in a gene of interest, and remains stably bound under stringent conditions (as defined by methods well known in the art, e.g., in Sambrook and Russell, 2001). Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

Nucleic acid molecules having base substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

As used herein, the term "derived" or "directed to" with respect to a nucleotide molecule means that the molecule has complementary sequence identity to a particular molecule of interest.

In certain embodiments, the expression cassette further contains a promoter. In certain embodiments, the promoter is a regulatable promoter. In certain embodiments, the promoter is a constitutive promoter. In certain embodiments, the promoter is a PGK, CMV or RSV promoter.

The present invention provides a vector containing the expression cassette described above. Expression vectors include, but are not limited to, viruses, plasmids, and other vehicles for delivering heterologous genetic material to cells. Accordingly, the term "expression vector" as used herein refers to a vehicle for delivering heterologous genetic material to a cell. In particular, the expression vector is a recombinant adenoviral, adeno-associated virus, or lentivirus or retrovirus vector. In certain embodiments, the viral vector is an adenoviral, lentiviral, adeno-associated viral (AAV), poliovirus, HSV, or murine Maloney-based viral vector.

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. It also may include sequences required for proper translation of the nucleotide sequence. The coding region usually codes for a protein of interest. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Binding Molecules

As used herein, the term "binding molecule" includes antibodies, which includes scFvs (also called a "nanobodies"), humanized, fully human or chimeric antibodies, single-chain antibodies, diabodies, and antigen-binding fragments of antibodies (e.g., Fab fragments).

In certain embodiments, the binding molecule does not contain the constant domain region of an antibody.

In certain embodiments, the binding molecule is less than 500 amino acids in length, such as between 200-450 amino acids in length, or less than 400 amino acids in length.

In certain embodiments, the binding molecule preferentially recognizes a particular stage of human AD Tau (e.g., AD Braak Stage I, compared to other AD stages).

In certain embodiments, the binding molecule preferentially recognizes tau associated with TBI.

In certain embodiments, the binding molecule binds to AD Tau. In certain embodiments, the binding molecule comprises an amino acid sequence of SEQ ID NO: 2, 4, 6, 8, 10, 12, 14, 16, 18, 20, 22, 24, 26, 28, 30, 32, 34, 36, 38, or 40. In certain embodiments, the binding molecule comprises an amino acid sequence encoded by a nucleic acid, wherein the nucleic acid has at least 80% identity to SEQ ID NO: 1, 3, 5, 7, 9, 11, 13, 15, 17, 19, 21, 23, 25, 27, 29, 31, 33, 35, 37, or 39.

In certain embodiments, the binding molecule binds to TBI Tau. In certain embodiments, the binding molecule comprises an amino acid sequence of SEQ ID NO: 42, 44, 46, or 48, 50, 52, 54, 56. In certain embodiments, the binding molecule comprises an amino acid sequence encoded by a nucleic acid, wherein the nucleic acid has at least 80% identity to SEQ ID NO: 41, 43, 45, 47, 49, 51, 53, or 55.

Detection Reagents and Assays

For purposes of the diagnostic methods of the invention, the compositions or ligand of the invention (e.g., binding molecule such as an antibody or antibody fragment) may be conjugated to a detecting reagent that facilitates detection of the ligand. For example, example, the detecting reagent may be a direct label or an indirect label. The labels can be directly attached to or incorporated into the detection reagent by chemical or recombinant methods.

In one embodiment, a label is coupled to the ligand through a chemical linker. Linker domains are typically polypeptide sequences, such as poly gly sequences of between about 5 and 200 amino acids. In some embodiments, proline residues are incorporated into the linker to prevent the formation of significant secondary structural elements by the linker. In certain embodiments, linkers are flexible amino acid subsequences that are synthesized as part of a recombinant fusion protein comprising the RNA recognition domain. In one embodiment, the flexible linker is an amino acid subsequence that includes a proline, such as Gly(x)-Pro-Gly(x) where x is a number between about 3 and about 100 (SEQ ID NO: 57). In other embodiments, a chemical linker is used to connect synthetically or recombinantly produced recognition and labeling domain subsequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

The detectable labels can be used in the assays of the present invention to diagnose TBI, these labels are attached to the ligand of the invention, can be primary labels (where the label comprises an element that is detected directly or that produces a directly detectable element) or secondary labels (where the detected label binds to a primary label, e.g., as is common in immunological labeling). An introduction to labels, labeling procedures and detection of labels is found in Polak and Van Noorden (1997) Introduction to Immunocytochemistry, 2nd ed., Springer Verlag, N.Y. and in Haugland (1996) Handbook of Fluorescent Probes and Research Chemicals, a combined handbook and catalogue Published by Molecular Probes, Inc., Eugene, Oreg. Patents that described the use of such labels include U.S. Pat. Nos. 3,817,837; 3,850,752; 3,939,350; 3,996,345; 4,277,437; 4,275,149; and 4,366,241.

Primary and secondary labels can include undetected elements as well as detected elements. Useful primary and secondary labels in the present invention can include spectral labels such as green fluorescent protein, fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectral calorimetric labels such as colloidal gold or colored glass or plastic (e.g. polystyrene, polypropylene, latex, etc.) beads. The label can be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Exemplary labels that can be used include those that use: 1) chemiluminescence (using horseradish peroxidase and/or alkaline phosphatase with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate (kits available from Life Technologies/Gibco BRL, and Boehringer-Mannheim)); 3) fluorescence using, e.g., an enzyme such as alkaline phosphatase, together with the substrate AttoPhos (Amersham) or other substrates that produce fluorescent products, 4) fluorescence (e.g., using Cy-5 (Amersham), fluorescein, and other fluorescent tags); 5) radioactivity. Other methods for labeling and detection will be readily apparent to one skilled in the art.

Where the ligand-based compositions of the invention are contemplated to be used in a clinical setting, the labels are preferably non-radioactive and readily detected without the necessity of sophisticated instrumentation. In certain embodiments, detection of the labels will yield a visible signal that is immediately discernable upon visual inspection. One example of detectable secondary labeling strategies uses an antibody that recognizes oligomers in which the antibody is linked to an enzyme (typically by recombinant or covalent chemical bonding). The antibody is detected when the enzyme reacts with its substrate, producing a detectable product. In certain embodiments, enzymes that can be conjugated to detection reagents of the invention include, e.g., β-galactosidase, luciferase, horse radish peroxidase, and alkaline phosphatase. The chemiluminescent substrate for luciferase is luciferin. One embodiment of a fluorescent substrate for β-galactosidase is 4-methylumbelliferyl-β-D-galactoside. Embodiments of alkaline phosphatase substrates include p-nitrophenyl phosphate (pNPP), which is detected with a spectrophotometer; 5-bromo-4-chloro-3-indolyl phosphate/nitro blue tetrazolium (BCIP/NBT) and fast red/napthol AS-TR phosphate, which are detected visually; and 4-methoxy-4-(3-phosphonophenyl) spiro[1,2-dioxetane-3,2'-adamantane], which is detected with a luminometer. Embodiments of horse radish peroxidase substrates include 2,2'azino-bis(3-ethylbenzthiazoline-6 sulfonic acid) (ABTS), 5-aminosalicylic acid (5AS), o-dianisidine, and o-phenylenediamine (OPD), which are detected with a spectrophotometer, and 3,3,5,5'-tetramethylbenzidine (TMB), 3,3' diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

The presence of a label can be detected by inspection, or a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

The ligand compositions of the invention can be used in any diagnostic assay format to determine the presence of human C SF/brain-associated tau variants. A variety of immunodetection methods are contemplated for this embodiment. Such immunodetection methods include enzyme linked immunosorbent assay (ELISA), radioimmunoassay (RIA), immunoradiometric assay, fluoroimmunoassay, chemiluminescent assay, bioluminescent assay, and Western blot, though several others are well known to those of ordinary skill. The steps of various useful immunodetection methods have been described in the scientific literature.

In general, the binding methods include obtaining a sample suspected of containing a protein, polypeptide and/or peptide (e.g., human CSF/brain-associated Tau variants), and contacting the sample with a first antibody, monoclonal or polyclonal, in accordance with the present invention, as the case may be, under conditions effective to allow the formation of complexes.

The binding methods include methods for detecting and quantifying the amount of the target oligomer component in a sample and the detection and quantification of any complexes formed during the binding process. Here, one would obtain a sample suspected of containing target oligomers, and contact the sample with an antibody fragment of the invention, and then detect and quantify the amount of complexes formed under the specific conditions.

Contacting the chosen biological sample with the antibody under effective conditions and for a period of time sufficient to allow the formation of complexes (primary complexes) is generally a matter of simply adding the antibody composition to the sample and incubating the mixture for a period of time long enough for the antibodies to form complexes with, i.e., to bind to, any antigens present. After this time, the sample-antibody composition, such as a tissue section, ELISA plate, dot blot or western blot, will generally be washed to remove any non-preferentially bound antibody species, allowing only those scFv molecules preferentially bound within the primary complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

As noted above, a ligand of the invention may itself be linked to a detectable label, wherein one would then simply detect this label, thereby allowing the amount of the primary complexes in the composition to be determined. Alternatively, a first antibody that becomes bound within the primary complexes may be detected by means of a second binding ligand that has binding affinity for the complex. In these cases, the second binding ligand may be linked to a detectable label. The second binding ligand is itself often an antibody, which may thus be termed a "secondary" ligand. The primary complexes are contacted with the labeled, secondary binding ligand or antibody under effective conditions and for a period of time sufficient to allow the formation of secondary complexes. The secondary complexes are then generally washed to remove any non-specifically bound labeled secondary antibodies or ligands, and the remaining label in the secondary complexes is then detected.

Further methods include the detection of primary complexes by a two-step approach. A second binding ligand, such as an antibody, that has binding affinity for the scFv is used to form secondary complexes, as described above. After washing, the secondary complexes are contacted with a third binding ligand or antibody that has binding affinity for the second antibody, again under effective conditions and for a period of time sufficient to allow the formation of complexes (tertiary complexes). The third ligand or antibody is linked to a detectable label, allowing detection of the tertiary complexes thus formed. This system may provide for signal amplification if this is desired.

One method of immunodetection designed by Charles Cantor uses two different antibodies. A first step biotinylated, monoclonal or polyclonal antibody or antibody fragment (in the present example a scFv) is used to detect the target antigen(s), and a second step antibody is then used to detect the biotin attached to the complex. In this method the sample to be tested is first incubated in a solution containing the first step ligand. If the target antigen is present, some of the ligand binds to the antigen to form a biotinylated ligand/antigen complex. The ligand/antigen complex is then amplified by incubation in successive solutions of streptavidin (or avidin), biotinylated DNA, and/or complementary biotinylated DNA, with each step adding additional biotin sites to the ligand/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of detection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

As detailed above, the assays in their most simple and/or direct sense are binding assays. Certain preferred assays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

The diagnostic assay format that may be used in the present invention could take any conventional format such as ELISA or other platforms such as luminex or biosensors. The present invention provides various ligands (e.g., scFv). These ligands can readily be modified to facilitate diagnostic assays, for example a tag (such as GFP) can be added to these ligands to increase sensitivity. In one exemplary ELISA, ligands (e.g., scFvs) are immobilized onto a selected surface exhibiting protein affinity, such as a well in a polystyrene microtiter plate.

Then, a test composition suspected of containing a target oligomer, such as a clinical sample (e.g., a biological sample obtained from the subject), is added to the wells. After binding and/or washing to remove non-specifically bound complexes, the bound antigen may be detected. Detection is generally achieved by the addition of an antibody that is linked to a detectable label. This type of ELISA is a simple "sandwich ELISA." Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with binding agents. After binding and/or washing to remove non-specifically bound complexes, the bound anti-binding agents are detected. Where the initial binding agents are linked to a detectable label, the complexes may be detected directly. Again, the complexes may be detected using a second antibody that has binding affinity for the first binding agents, with the second antibody being linked to a detectable label.

Another ELISA in which the antigens are immobilized, involves the use of antibody competition in the detection. In this ELISA, labeled antibodies (or nanobodies) against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes.

In coating a plate with either target oligomers or a ligand (e.g., antibody) of the invention, one will generally incubate the wells of the plate with a solution of the antigen or ligand, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the tau oligomers and/or scFv composition with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. An example of a washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. This may be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

Diagnostic Methods

In certain embodiments, the present invention provides a method for determining risk of traumatic brain injury (TBI) and/or susceptibility to neurodegenerative disease in a subject by measuring levels of particular tau oligomeric proteins preferentially associated with different stages of AD or with TBI.

In certain embodiments, the present invention provides a method for determining risk of traumatic brain injury (TBI), assessment of the amount of neuronal damage, and/or susceptibility to neurodegenerative disease in a subject, comprising the steps of:

(A) providing a sample obtained from a subject post-injury;

(B) assessing levels of TBI-associated tau in the sample;

(C) comparing the TBI-associated tau protein level in the sample with TBI-associated tau protein level in a normal control; and (D) determining whether the subject has a risk of TBI in accordance with the result of step (C);

wherein a subject having elevated TBI-associated tau protein has a high risk of TBI.

In certain embodiments, the sample and the normal control are blood product samples or cerebrospinal fluid (CSF) samples. In certain embodiments, the blood product is serum.

In certain embodiments, the detecting in step (B) is by means of a ligand specific for the protein.

In certain embodiments, the ligand is an antibody.

In certain embodiments, the ligand is a scFv specific for TBI-associated tau.

In certain embodiments, the protein levels are detected by means of ELISA.

The invention will now be illustrated by the following non-limiting Example.

EXAMPLE 1

Isolation of Nanobodies Selective for Tau Species in TBI but Not ND CSF Samples Morphology-specific nanobodies are used to identify the set of serum biomarkers that are diagnostic for AD, and determine if these also show up in a subset of TBI patients. Soldiers suffering TBI who show reactivity similar to the AD biomarker set, have suffered damage similar to that shown in AD brain, and should be much more susceptible to AD. The goal is to rapidly and accurately detect and quantify a selected set of toxic protein variants of Aβ, tau and a-syn that are characteristic of AD.

Nanobodies specific to selected tau species unique to TBI were isolated. Tau is present in human tissue in a variety of different forms since it is generated through multiple splicing events and can have a variety of different post-translational modifications. Because of the diversity of tau species, there are selected species that are indicative of particular neuronal conditions such as AD or other tauopathies. Nanobodies were generated that selectively recognize tau species present in TBI patients.

Immunoprecipitate Total Tau from Two Different Regions of Age Matched Post-Mortem Human AD and Cognitively Normal Brain Tissue Brain Tissue and CSF: AD and normal brain tissue samples were obtained from Banner/Sun Health Brain Bank (BSHBB). Samples were obtained from two different brain regions of AD cases confirmed to have abundant tangles, the superior frontal gyms and middle temporal gyms. Ten different AD and 10 different control patient samples were received for a total of 20 AD and 20 control samples. All subjects had a PMI less than 5 hours. Detailed clinical and neuropathological data were available on these subjects, including MMSE, CERAD neuritic plaque density scores, Braak tangle stage and regional Lewy-typealpha-syncleinopathy density scores. Post-mortem samples were de-identified for all personal patient information. CSF from four different patients who had sustained head injury and control CSF from 15 normal/healthy individuals were obtained from Banner Sun Health. These samples were used to identify potential markers in traumatic brain injury compared to control.

Brain tissue lysis: Briefly, frozen samples were homogenized by supersonication in cold lysis buffer: 25 mM HEPESNaOH (pH 7.9), 150 mM NaCl, 1.5 mM $MgCl_2$, 0.2 mM EDTA, 0.5% Triton-X-100, 1 mM dithiothreitol, proteaseinhibitor cocktail. The homogenized sample was centrifuged and the supernatant was frozen in −80 ° C. The presence of fibrillar tau was verified by immunohistochemistry using slices from one AD and one ND sample and staining with an antibody against phosphorylated tau. The AD sample showed significantly more tau tangle pathology than the control sample (FIG. 1).

Figure 2:
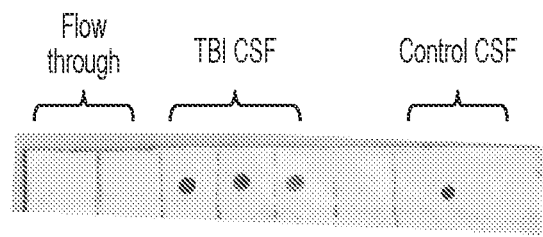
FIG. 2: Dotblot assay confirming the presence of immunoprecipitated tau from TBI and control CSF samples in the IP elutes following immunoprecipitation protocol.
Figure 3A:
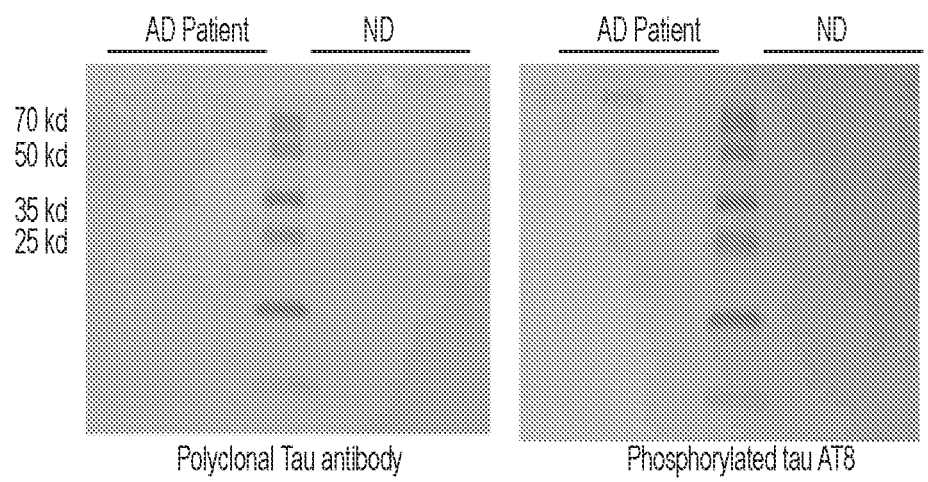
FIGS. 3a and 3b.
Figure 3B:
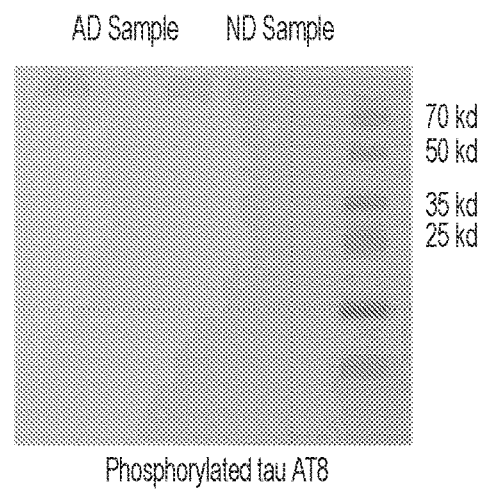

Immunoprecipitation of tau protein: Two polyclonal tau antibody preparations were used to immunoprecipitate tau from the AD brain homogenates, TBI CSF and corresponding controls: PA1 against amino-acids 240-450 of tau and PAS against amino-acid 1-286 to cover all isoforms. Antibody conjugates were captured using the Pierce Crosslink IP Kit A following the manufacturers' protocols. With the crosslink kit, the antibody first binds the protein A/G agarose and then is chemically crosslinked to the resin preventing the antibody from eluting off the column. Tau was eluted from the column using a low pH elution buffer. To preserve integrity of the tau aggregates, the elution buffer was neutralized with 1M Tris, pH 9.5 as recommended by the manufacturer. The brain slices (FIG. 1) were analyzed and tau eluted from TBI CSF using dot blots (FIG. 2), and tau eluted from the brain tissue by western blot (FIGS. 3a and 3b).

Figure 4:
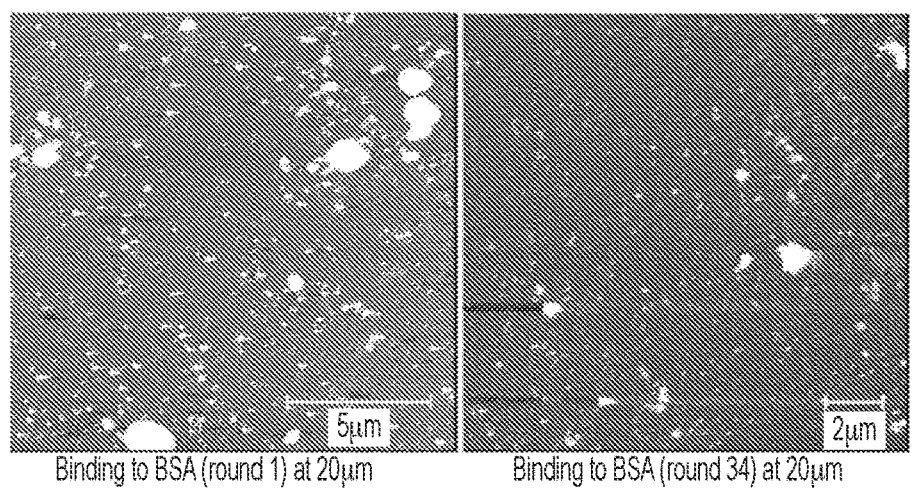
FIG. 4: Negative panning against bovine serum albumin.

Biopanning—AD tau specific morphologies: Aliquots of the Sheets, Tomlinson I and J and DARPin scFv libraries were grown and combined to generate scFv library stock with titers of around 10e13. Negative panning steps were performed to remove phage clones that bind to non-target sticky protein samples including bovine serum album (FIG. 4). Several rounds of negative panning was performed against α-synuclein aggregates to remove all antibody fragments that bind generic forms of aggregated protein morphologies. Additional negative panning steps against monomeric tau, healthy tissue samples and healthy tau samples were performed to remove all antibody fragments that bind to generic forms of tau found in healthy individuals. Atomic force microscopy (AFM) imaging was performed after every negative panning step to ensure removal of non-specific antibody fragments. Final positive selection was performed using for AD braak stage III and V specific tau variant morphologies.

Figure 5:
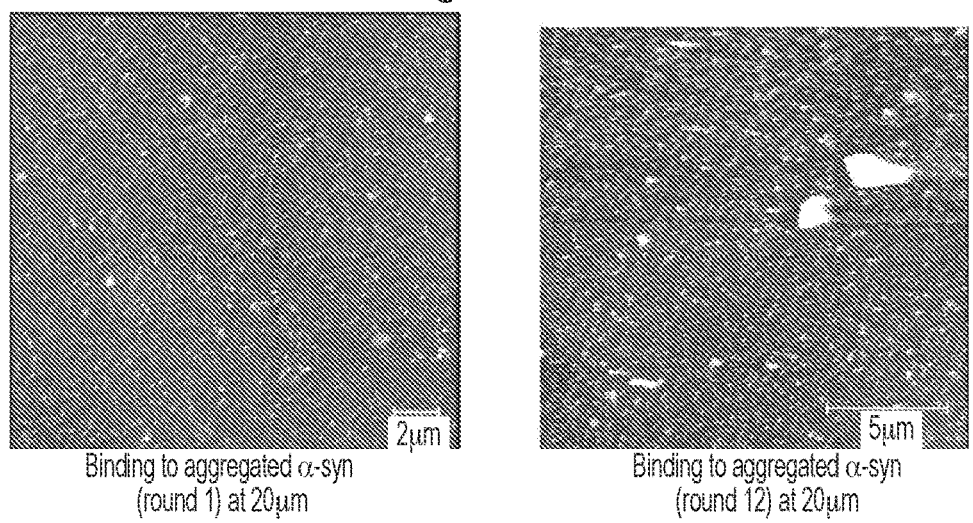
FIG. 5: Negative panning against aggregated α-synuclein.
Figure 6:
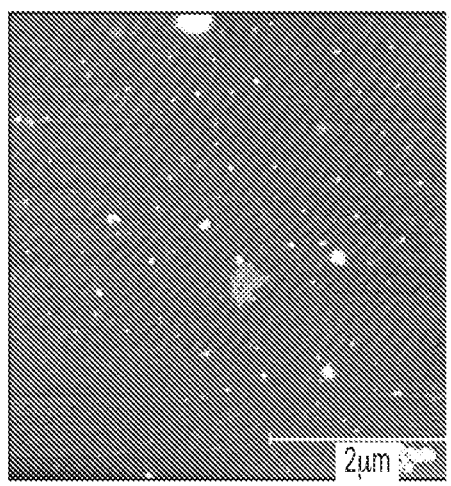
FIG. 6: Negative panning against AD Braak stage I tissue.
Figure 6:
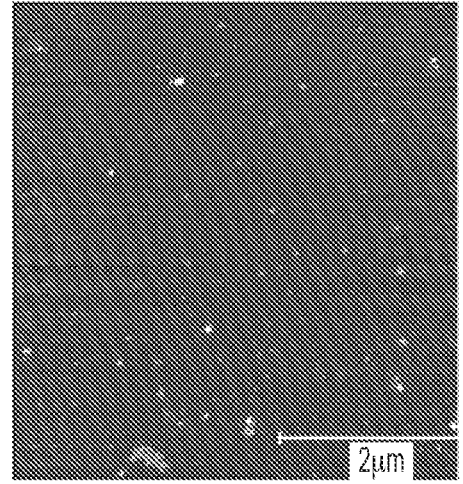
Figure 7:
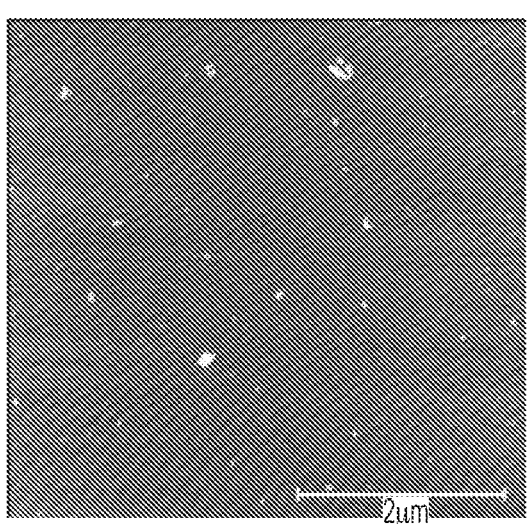
FIG. 7: Negative panning against AD Braak stage I tau IP (Black arrow indicates phage).
Figure 7:
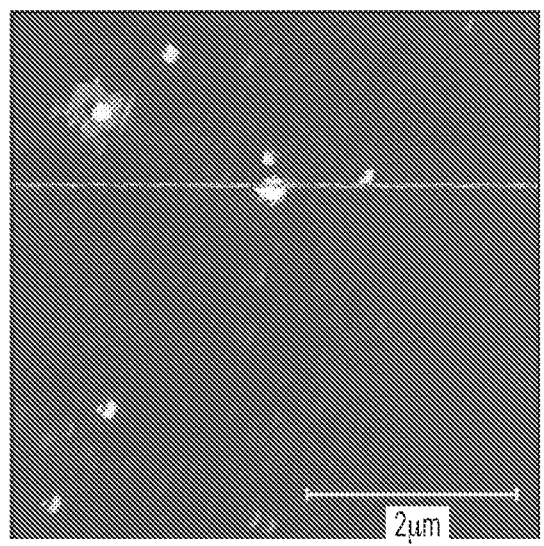

TBI tau specific morphologies: A clone that could bind to all forms of tau is essential and is used as a secondary detection reagent in sandwich ELISA. Hence, phage obtained after negative panning with α-synuclein (FIG. 5) was used for positive panning against monomeric tau. For panning against tau isolated from TBI, eight rounds of negative panning against control CSF samples (10 μg/mL) were first performed. Cleaved mica surface was used to conserve sample. This step was used to remove all phage binding to proteins and other components present in normal CSF including any tau variants present in healthy individuals. Phage remaining after negative panning against BSA, α-synuclein and control CSF was used to carry out positive panning with tau immunoprecipitated from TBI CSF samples (FIGS. 6, 7). Positive binding clones were eluted using either Trypsin or TEA and recovered by infecting TG1 cells.

Figure 8:
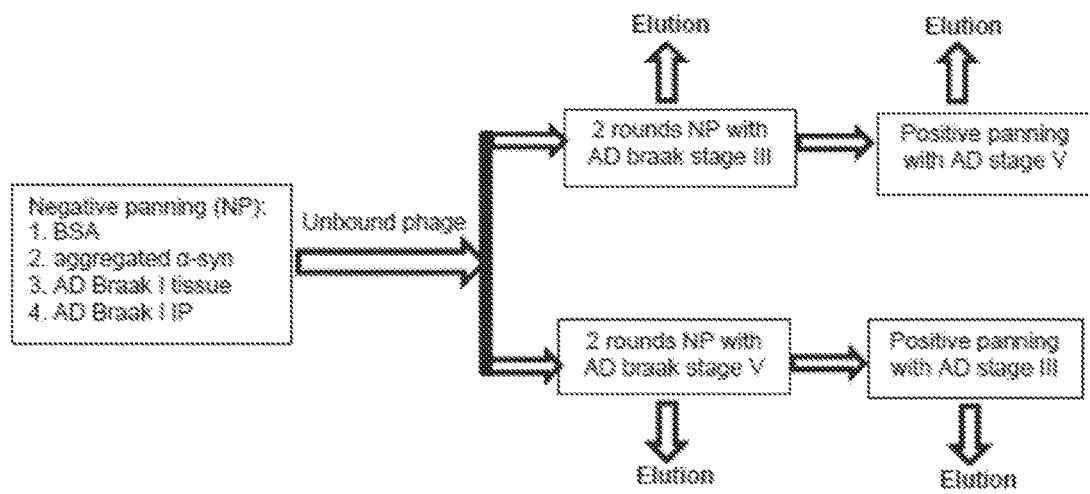
FIG. 8: Flow diagram indicating steps in the panning protocol. Negative selection to remove non-specific clones was followed by positive selection with tau immunoprecipitated from AD Braak stage III and Braak stage V.

AD tau clones: After two rounds of positive panning with AD Braak stage III, unbound phage clones were used for a positive round of selection against AD Braak stage V and vice versa (FIG. 8). Each of the micas was eluted using trypin and TEA and grown on LB—Amp plates overnight at 37° C. About 60 clones were obtained before negative panning with AD Braak stage III and V. Typically 50-100 clones are obtained in this step and the results obtained are encouraging. After further rounds of negative panning with AD Braak stage V and III, 15 and 20 clones were obtained against AD Braak stage III and Braak stage V respectively. The number of clones after the final rounds of positive panning was as anticipated. To ensure these clones are capable of making full length antibody fragment, their sequences were checked for any mutations and stop codons. Phage was produced for clone sequences free of any errors. Dotblots spotted with human AD homogenized brain tissue and corresponding controls were used to verify each of the phage clones.

TBI tau clone: Approximately 24 clones were recovered from the panning against tau variants present in the TBI CSF samples. Typically it is expected to recover around 20-50 clones in the positive panning step so this was an encouraging result. These clones were further sequenced to check for any stop codons or mutations. This step ensures that these clones are capable of making full length antibody fragments. Several clones isolated against TBI had complete sequences free of any stop codons, mutations or errors. Phage was produced for such clones which were verified using dotblots using TBI CSF and corresponding CSF controls. The blot was visualized using a chemiluminescent substrate and the blot was developed using film. The dotblots showed high binding to TBI and relatively lower binding to controls. Further characterization using ELISA assays were performed.

Indirect AD ELISA: Indirect ELISA was performed to check the specificity of each of the phage clones to tau variants in AD brain tissue. The assay parameters and wash steps were optimized to yield a high signal to noise ratio. Human brain homogenates (mix of individual samples classified by their Braak stage) was used to coat the plates and 2% milk was used subsequently to block the wells. Each of the phage clones were tested with pooled ND controls, AD Braak stage III and AD Braak stage V homogenates. Secondary anti-M13 and chemiluminescent substrate was used for detection. The luminescence was measured using a spectrophotometer and represented as a ratio with respect to ND control.

Figure 9:
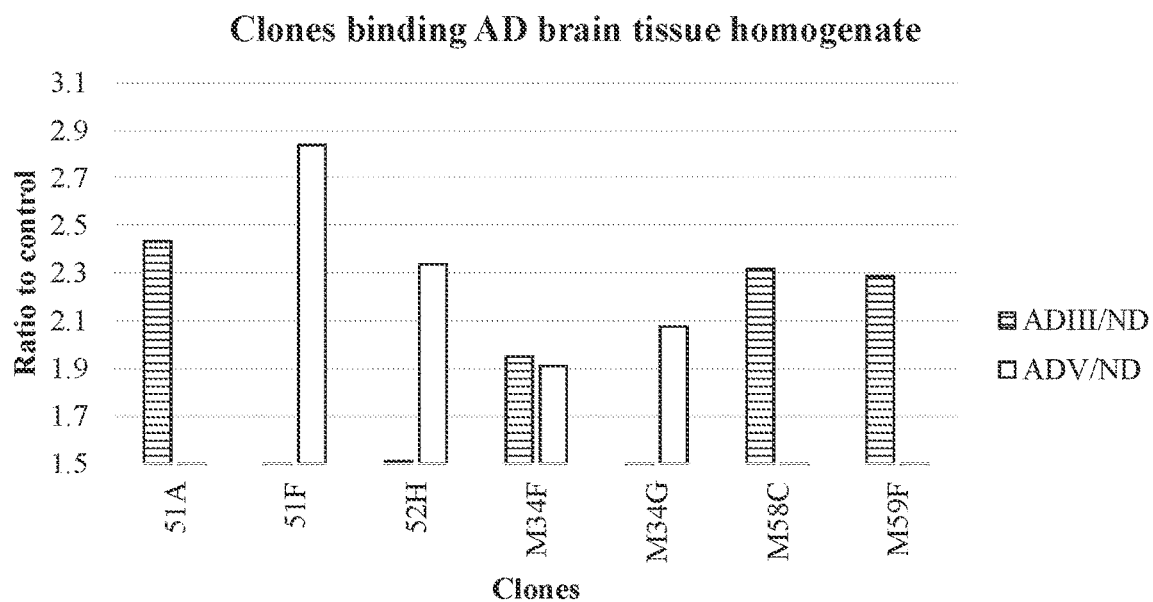
FIG. 9: Indirect ELISA assay testing different AD tau phage clones with pooled AD brain tissue homogenates. X axis represents the various clones and Y axis represents luminescence signal ratio to ND controls. All the clones have high levels of binding to AD tissue (Braak stage III and V) compared to the controls.

The clones were initially screened with pooled samples to check if they selected AD over control samples. From this initial assay it can be noted that several clones preferentially bound to tau morphologies in AD Braak stage III (51A, M58C and M59F) and there were a few clones (51F, 52H and M34G) that preferentially bound to tau forms present in AD Braak stage V (FIG. 9). This indicates that unique tau species exist during different AD Braak stages. These clones serve as a tool in tracking the progression of AD. Other clones that preferentially bound to both AD Braak stage III and V (M34F) indicate overlap of tau species common to Braak stages III and V. These clones serve as a potential secondary reagent for detection in a sandwich ELISA.

Figure 10:
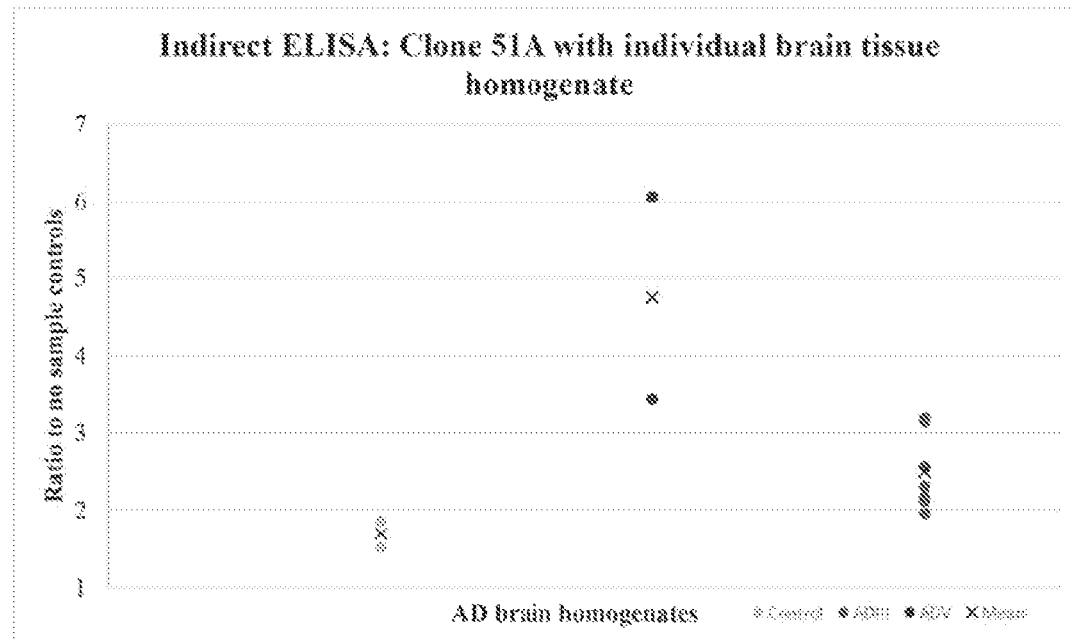
FIG. 10: Indirect ELISA of clone 51A with individual AD brain tissue homogenates. 7 samples (Braak V), 2 samples (Braak III) and 2 samples (Braak I) were tested. This clone binds tau morphologies present in AD Braak stage III.
Figure 11:
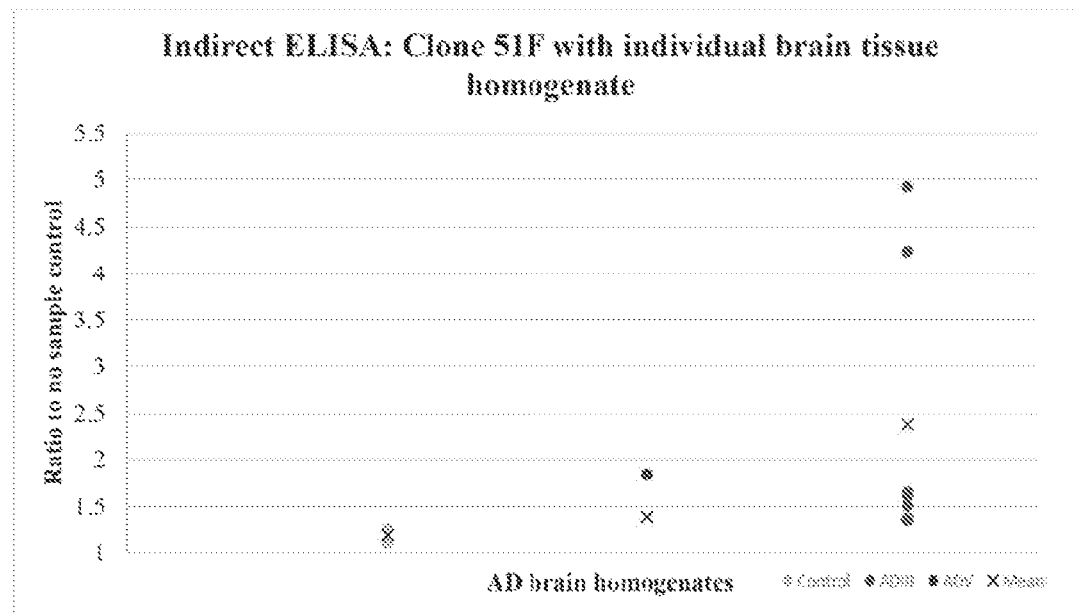
FIG. 11: Indirect ELISA of clone 51F with individual AD brain tissue homogenates. 7 samples (Braak V), 2 (Braak III) and 2 (Braak I) were tested. This clone binds tau morphologies in AD Braak stage V.
Figure 12:
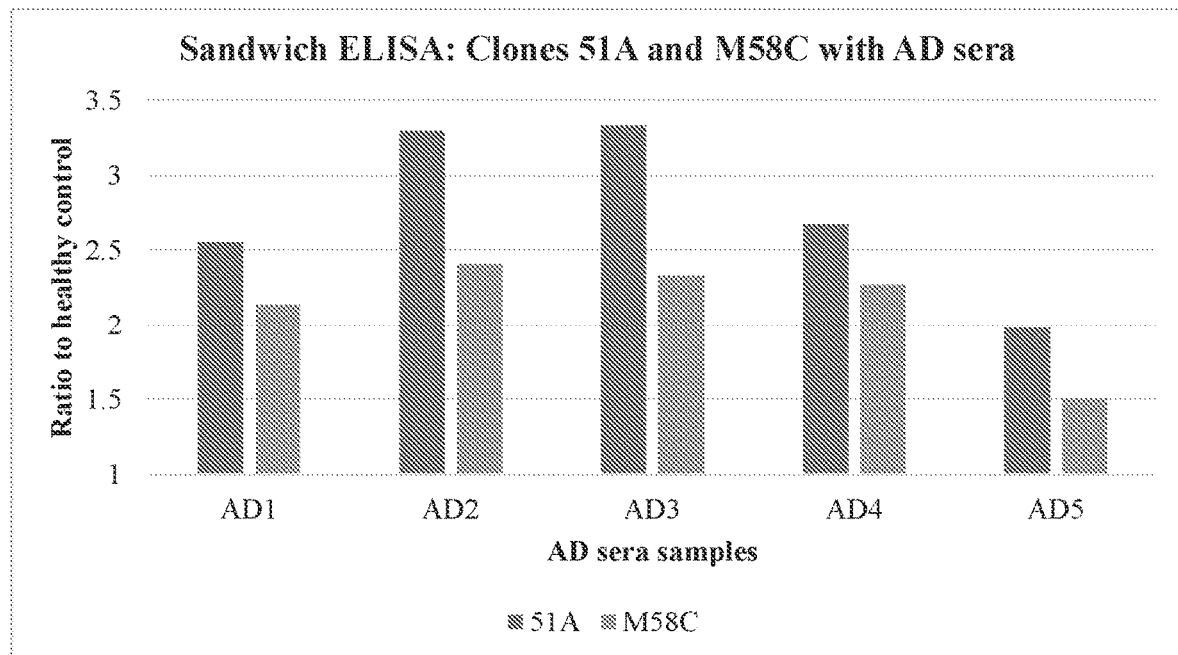
FIG. 12: Sandwich ELISA with AD clones 51A and M58C with 5 AD sera samples. X-Axis represents individual sera samples and Y-Axis represents ratio to healthy control. Both the clones selectively bind to tau morphologies present in AD sera over healthy control.

51A and 51F clones had high binding ratios to AD Braak stage III and V respectively in the initial ELISA assay. These clones were further tested with individual AD brain tissue homogenates (FIGS. 10 through 12). They selectively bind to individual samples classified under Braak stage III and V respectively. Both these clones have relatively very low binding to ND control indicating that the negative panning steps against the ND controls was successful.

Indirect TBI ELISA: Indirect ELISA was performed to check the specificity of each of the phage clones to tau variants in TBI CSF. The assay parameters and wash steps were optimized to yield a high signal to noise ratio. Pooled TBI and control CSF samples were used to coat the plates and milk was used subsequently to block the wells. Each of the phage clones were tested with AD I, ADIII and ADV homogenates. Secondary anti-M13 and chemiluminescent substrate was used for detection. The luminescence was measured using a spectrophotometer and represented as a ratio with respect to no sample control.

Figure 13:
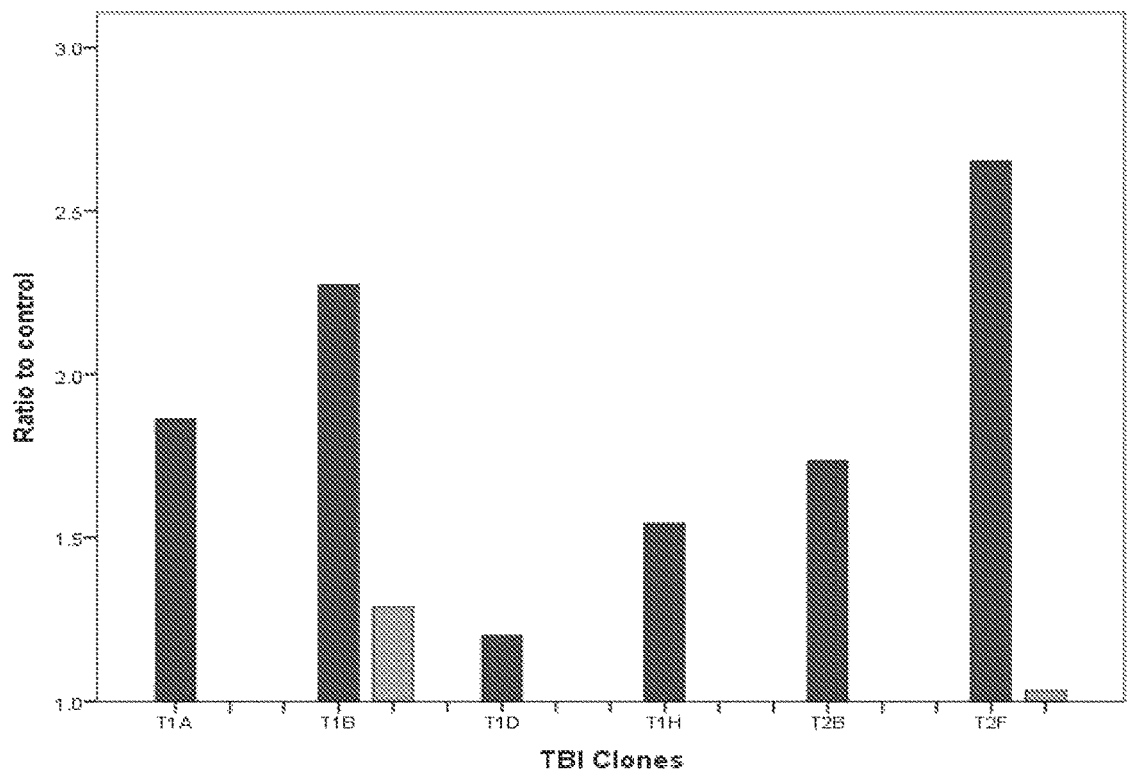
FIG. 13: Indirect ELISA of TBI clones with pooled TBI and control CSF. X axis represents the TBI clones and Y axis represents ratio to no sample control. Most of the clones had high levels of binding to TBI compared to control.

Several clones preferentially bound to tau morphologies in TBI CSF over control (FIG. 13). This indicates that unique tau species circulate in the CSF of traumatic brain injured individuals compared to controls. These clones can serve as a tool in differentiating TBI and healthy individuals.

Figure 14:
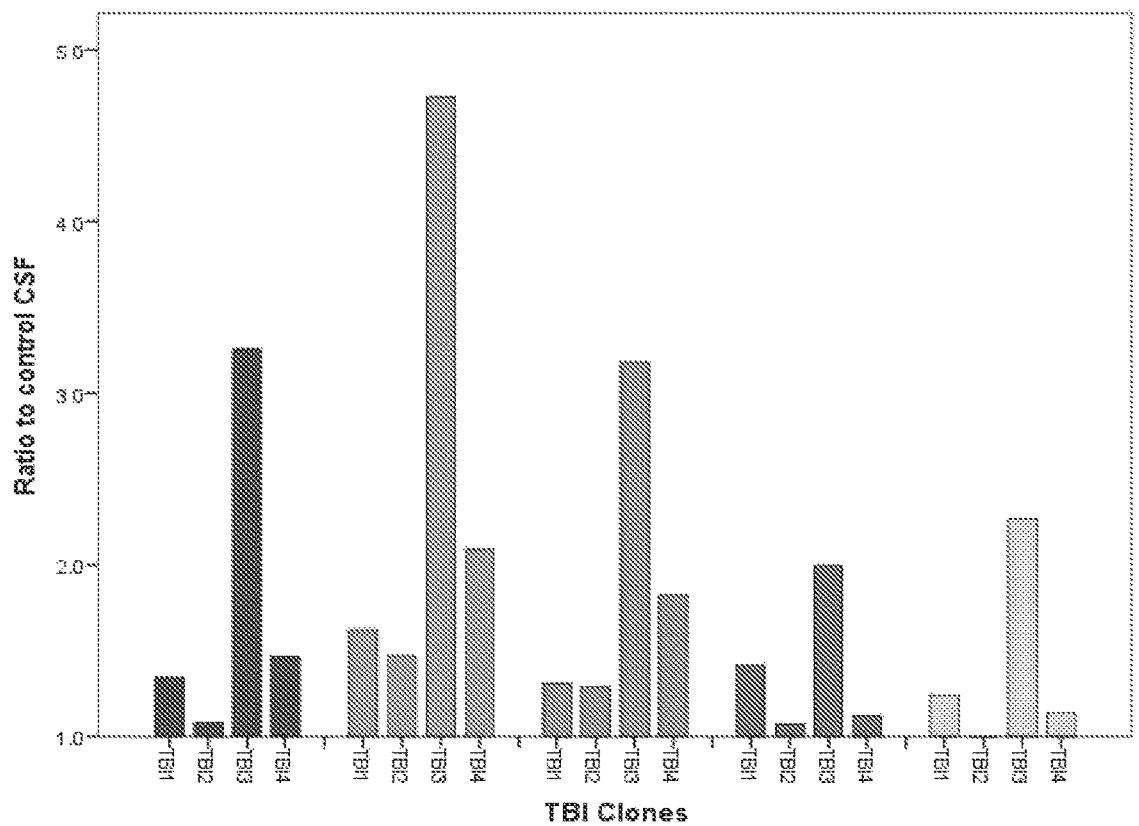
FIG. 14: Indirect ELISA of TBI clones with individual TBI (4 samples) and pooled control CSF. X axis represents the TBI clones and Y axis represents ratio to control CSF. Most of the clones have high levels of binding to TBI samples.
Figure 15:
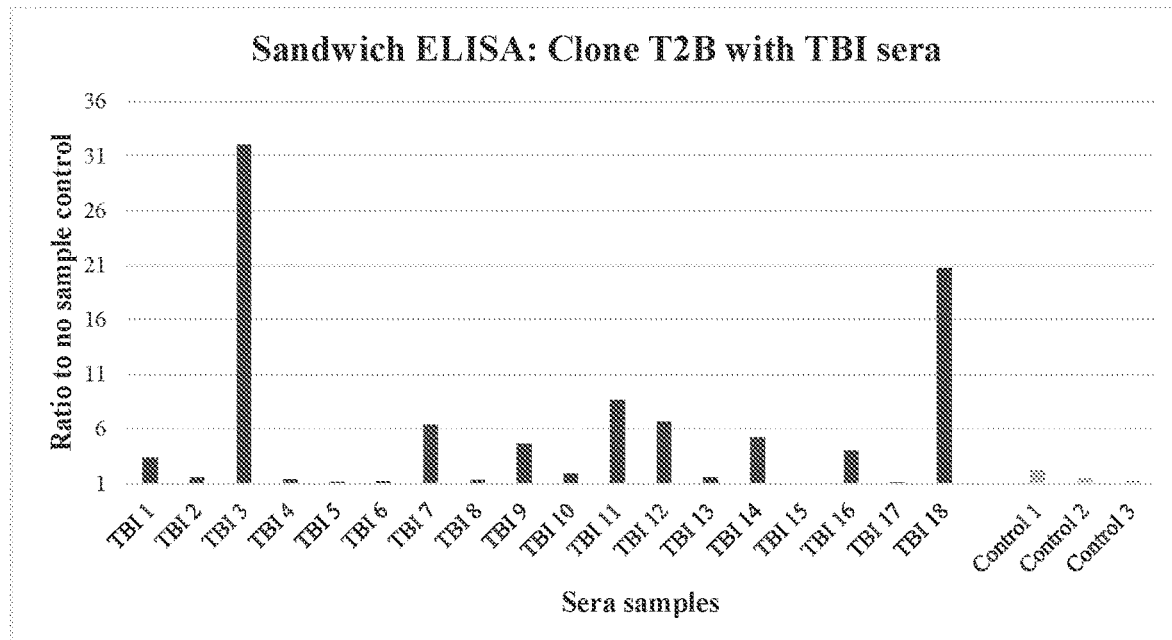
FIG. 15: Sandwich ELISA of clone T2B with 18 TBI sera samples and 3 healthy aged controls. X-Axis represents individual sera samples and Y-Axis represents ratio to no sample control. T2B selectively binds to tau species that possibly circulates in TBI individuals several years after their head trauma when compared to healthy controls.

Clones that gave a high binding ratio to pooled TBI CSF samples were further tested with individual TBI and control CSF samples. As can be seen from FIGS. 14-15, each of the TBI clones were able to selectively pick out all four of the TBI CSF samples over pooled control CSF sample. Almost all the clones had high binding ratio to one of the TBI samples. This could possibly be due to the presence of high levels of TBI specific tau morphologies in this sample which were recognized by the individual clones. Each clone's binding ratio to the individual TBI samples are different indicating that each clone might not necessarily be binding to the same type of tau species. These clones can serve as a tool in recognizing specific tau forms in TBI.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A binding molecule
wherein the binding molecule preferentially binds to human Alzheimer's Disease (AD)-associated tau and comprises an amino acid sequence at least 95% identical to:
   (a) an antibody heavy chain variable domain and light chain variable domain of SEQ ID NO:2, SEQ ID NO:4, SEQ ID NO:6, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO:40; or
   (b) a DARPin of SEQ ID NO:8;
   wherein differences from the heavy chain variable domain and light chain variable domain of (a) or the DARPin of (b) are conservative substitutions.

2. The binding molecule of claim 1, wherein the antibody comprises a chimeric antibody, a single-chain antibody, a diabody, an Fab, or an scFv.

3. A nucleic acid that encodes the binding molecule of claim 1.

4. A vector comprising the nucleic acid of claim 3.

5. A phage comprising the vector of claim 4.

6. A phage comprising the binding molecule of claim 1.

7. A method of detecting Alzheimer's Disease (AD)-associated tau in a subject, the method comprising:
   (a) incubating a sample from the subject with a binding molecule that preferentially recognizes AD-associated tau; and
   (b) comparing the amount of AD-associated tau bound to the binding molecule with the amount of AD-associated tau bound to the binding molecule in a control sample;
   wherein the binding molecule comprises an antibody or DARPin of claim 1.

8. A method for detecting traumatic brain injury (TBI), neuronal damage, and/or susceptibility to neurodegenerative disease in a subject, the method comprising:
   (a) detecting TBI-associated tau in a post-injury sample from the subject; and
   (b) comparing the level of TBI-associated tau protein in the sample with TBI-associated tau protein level in a normal control;
   wherein detecting TBI-associated tau comprises incubating the sample with a binding molecule of claim 1 that preferentially recognizes TBI-associated tau; and
   wherein elevated TBI-associated tau protein in the post-injury sample indicates TBI, neuronal damage, and/or susceptibility to neurodegenerative disease.

9. The method of claim 8, wherein the sample and the normal control comprise blood product samples or cerebrospinal fluid (CSF) samples.

10. A method for detecting Alzheimer's Disease (AD), neuronal damage, and/or susceptibility to neurodegenerative disease in a subject, the method comprising:
   (a) detecting AD-associated tau in a post-injury sample from the subject; and
   (b) comparing the level of AD-associated tau protein in the sample with AD-associated tau protein level in a normal control;
   wherein detecting AD-associated tau comprises incubating the sample with a binding molecule of claim 1 that preferentially recognizes AD-associated tau; and
   wherein elevated AD-associated tau protein in the post-injury sample indicates AD, neuronal damage, and/or susceptibility to neurodegenerative disease.

11. The method of claim 10, wherein the sample and the normal control comprise blood product samples or cerebrospinal fluid (CSF) samples.

* * * * *

SEQUENCE LISTING

<160> NUMBER OF SEQ ID NOS: 57

<210> SEQ ID NO 1
<211> LENGTH: 912
<212> TYPE: DNA
<213> ORGANISM: Artificial Sequence

```
<220> FEATURE:
<223> OTHER INFORMATION: Description of Artificial Sequence: Synthetic
      polynucleotide
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (28)..(28)
<223> OTHER INFORMATION: a, c, t, g, unknown or other
<220> FEATURE:
<221> NAME/KEY: modified_base
<222> LOCATION: (41)..(41)
<223> OTHER INFORMATION: a, c, t, g, unknown or other
<220> FEATURE:
<221> NAME/KEY: modified_base
<222> LOCATION: (59)..(59)
<223> OTHER INFORMATION: a, c, t, g, unknown or other
<220> FEATURE:
<221> NAME/KEY: modified_base
<222> LOCATION: (68)..(68)
<223> OTHER INFORMATION: a, c, t, g, unknown or other
<220> FEATURE:
<221> NAME/KEY: modified_base
<222> LOCATION: (71)..(71)
<223> OTHER INFORMATION: a, c, t, g, unknown or other

<400> SEQUENCE: 1
gattacngcc aagcttgcat gcaaattnta tttcaaggag ncagtcataa tgaaatacnt      60
attgccyncg ncagccgctg gattgttatt actcgcggcc cagccggcca tggccgaggt     120
gcagctgttg gagtctgggg gaggcttggt acagcctggg gggtccctga gactctcctg     180
tgcagcctct ggattcacct ttagcagcta tgccatgagc tgggtccgcc aggctccagg     240 gaagggctg gagtgggtct catctatttc ttctaatggt gatgatacag cttacgcaga     300
ctccgtgaag ggccggttca ccatctccag agacaattcc aaggacacgc tgtatctgca     360
aatgaacagc ctgagagccg aggacacggc cgtatattac tgtgcgaaag ctaataattc     420
ttttgactac tggggccagg gaaccctggt caccgtctcg agcggtggag cggttcagg     480 cggaggtggc agcggcggtg gcgggtcgac ggacatccag atgacccagt ctccatcctc     540
cctgtctgca tctgtaggag acagagtcac catcacttgc cggcaagtc agagcattag     600 cagctattta aattggtatc agcagaaacc agggaaagcc cctaagctcc tgatctataa     660
tgcatccact ttgcaaagtg ggtccccatc aaggttcagt ggcagtggat ctgggacaga     720
tttcactctc accatcagca gtctgcaacc tgaagatttt gcaacttact actgtcaaca     780
ggatagtgct actccttata cgttcggcca agggaccaag gtggaaatca acgggcggc     840 cgcacatcat catcaccatc acggggccgc agaacaaaaa ctcatctcag aagaggatct     900
gaatggggcc gc                                                         912

<210> SEQ ID NO 2
<211> LENGTH: 287
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (7)..(8)
<223> OTHER INFORMATION: Any amino acid
```

<400> SEQUENCE: 2

Met Lys Tyr Xaa Leu Pro Xaa Xaa Ala Ala Gly Leu Leu Leu Leu Ala
1               5                   10                  15

Ala Gln Pro Ala Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Ser Ile Ser Ser Asn Gly Asp Asp Thr
65                  70                  75                  80

Ala Tyr Ala Asp Ser Val Lys Gly Arg Phe Thr Ile Ser Arg Asp Asn
                85                  90                  95

Ser Lys Asp Thr Leu Tyr Leu Gln Met Asn Ser Leu Arg Ala Glu Asp
            100                 105                 110

Thr Ala Val Tyr Tyr Cys Ala Lys Ala Asn Asn Ser Phe Asp Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Thr Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Asn Ala Ser Thr Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Asp Ser Ala Thr Pro Tyr Thr Phe Gly Gln Gly Thr
                245                 250                 255

Lys Val Glu Ile Lys Arg Ala Ala Ala His His His His His His Gly
            260                 265                 270

Ala Ala Glu Gln Lys Leu Ile Ser Glu Glu Asp Leu Asn Gly Ala
        275                 280                 285

<210> SEQ ID NO 3
<211> LENGTH: 927
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: modified_base
<222> LOCATION: (37)..(37)

<223> OTHER INFORMATION: a, c, t, g, unknown or other
<220> FEATURE:
<221> NAME/KEY: modified_base
<222> LOCATION: (76)..(76)
<223> OTHER INFORMATION: a, c, t, g, unknown or other
<220> FEATURE:
<221> NAME/KEY: modified_base
<222> LOCATION: (81)..(81)
<223> OTHER INFORMATION: a, c, t, g, unknown or other
<220> FEATURE:
<221> NAME/KEY: modified_base
<222> LOCATION: (90)..(91)
<223> OTHER INFORMATION: a, c, t, g, unknown or other
<220> FEATURE:
<221> NAME/KEY: modified_base
<222> LOCATION: (112)..(112)
<223> OTHER INFORMATION: a, c, t, g, unknown or other
<220> FEATURE:
<221> NAME/KEY: modified_base
<222> LOCATION: (141)..(141)
<223> OTHER INFORMATION: a, c, t, g, unknown or other
<220> FEATURE:
<221> NAME/KEY: modified_base
<222> LOCATION: (220)..(220)
<223> OTHER INFORMATION: a, c, t, g, unknown or other

<400> SEQUENCE: 3

```
tatganccat gattacgcca agctnncatg caanntntat tttcaaggag acagtcataa      60
tgaaatacct attgcntacg ncagccgctn ngattgttat tactcgcggc cncagccggc     120
catggccgag gtgcagctgt nggagtctgg gggaggcttg gtacagcctg gggggtccct     180
gagactctcc tgtgcagcct ctggattcac ctttagcagn tatgccatga gctgggtccg     240
ccaggctcca gggaagggc tggagtgggt ctcatagatt tagcagtcgg gtccggttac     300
atcttacgca gactccgtga agggccggtt caccatctcc agagacaatt ccaagaacac     360
gctgtatctg caaatgaaca gcctgagagc cgaggacacg ccgtatatt actgtgcgaa     420
acgtcagttg atgtttgact actggggcca gggaaccctg gtcaccgtct cgagcggtgg     480
aggcggttca ggcggaggtg gcagcggcgg tggcgggtcg acggacatcc agatgaccca     540
gtctccatcc tccctgtctg catctgtagg agacagagtc accatcactt gccgggcaag     600
tcagagcatt agcagctatt taaattggta tcagcagaaa ccagggaaag cccctaagct     660
cctgatctat gctgcatcca gtttgcaaag tggggtccca tcaaggttca gtggcagtgg     720
atctgggaca gatttcactc tcaccatcag cagtctgcaa cctgaagatt ttgcaactta     780
ctactgtcaa cagagttaca gtacccctaa tacgttcggc caagggacca aggtggaaat     840
caaacgggcg gccgcacatc atcatcacca tcacggggcc gcagaacaaa aactcatctc     900
agaagaggat ctgaatgggc cgcatag                                          927
```

<210> SEQ ID NO 4
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (33)..(33)
<223> OTHER INFORMATION: Any amino acid

<400> SEQUENCE: 4

```
Met Ala Glu Val Gln Leu Xaa Glu Ser Gly Gly Leu Val Gln Pro
1               5                  10                 15

Gly Gly Ser Leu Arg Leu Ser Cys Ala Ala Ser Gly Phe Thr Phe Ser
        20                  25                 30

Xaa Tyr Ala Met Ser Trp Val Arg Gln Ala Pro Gly Lys Gly Leu Glu
            35                  40                 45

Trp Val Ser Ile Gln Ser Gly Pro Val Thr Ser Tyr Ala Asp Ser Val
    50                  55                 60

Lys Gly Arg Phe Thr Ile Ser Arg Asp Asn Ser Lys Asn Thr Leu Tyr
65                  70                  75                 80

Leu Gln Met Asn Ser Leu Arg Ala Glu Asp Thr Ala Val Tyr Tyr Cys
                85                  90                 95

Ala Lys Arg Gln Leu Met Phe Asp Tyr Trp Gly Gln Gly Thr Leu Val
            100                 105                110

Thr Val Ser Ser Gly Gly Gly Gly Ser Gly Gly Gly Gly Ser Gly Gly
        115                 120                125

Gly Gly Ser Thr Asp Ile Gln Met Thr Gln Ser Pro Ser Ser Leu Ser
        130                 135                140

Ala Ser Val Gly Asp Arg Val Thr Ile Thr Cys Arg Ala Ser Gln Ser
145                 150                 155                160

Ile Ser Ser Tyr Leu Asn Trp Tyr Gln Gln Lys Pro Gly Lys Ala Pro
                165                 170                175

Lys Leu Leu Ile Tyr Ala Ala Ser Ser Leu Gln Ser Gly Val Pro Ser
            180                 185                190

Arg Phe Ser Gly Ser Gly Ser Gly Thr Asp Phe Thr Leu Thr Ile Ser
        195                 200                205

Ser Leu Gln Pro Glu Asp Phe Ala Thr Tyr Tyr Cys Gln Gln Ser Tyr
    210                 215                 220

Ser Thr Pro Asn Thr Phe Gly Gln Gly Thr Lys Val Glu Ile Lys Arg
225                 230                 235                240

Ala Ala Ala His His His His His His Gly Ala Ala Glu Gln Lys Leu
                245                 250                255

Ile Ser Glu Glu Asp Leu Asn Gly Pro His
            260                 265

<210> SEQ ID NO 5
<211> LENGTH: 833
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (14)..(15)
<223> OTHER INFORMATION: a, c, t, g, unknown or other
<220> FEATURE:
<221> NAME/KEY: modified_base
<222> LOCATION: (28)..(28)
<223> OTHER INFORMATION: a, c, t, g, unknown or other
<220> FEATURE:
<221> NAME/KEY: modified_base
<222> LOCATION: (34)..(34)
<223> OTHER INFORMATION: a, c, t, g, unknown or other
<220> FEATURE:
<221> NAME/KEY: modified_base
<222> LOCATION: (37)..(37)
<223> OTHER INFORMATION: a, c, t, g, unknown or other
```

```
<220> FEATURE:
<221> NAME/KEY: modified_base
<222> LOCATION: (67)..(67)
<223> OTHER INFORMATION: a, c, t, g, unknown or other
<220> FEATURE:
<221> NAME/KEY: modified_base
<222> LOCATION: (71)..(77)
<223> OTHER INFORMATION: a, c, t, g, unknown or other
<220> FEATURE:
<221> NAME/KEY: modified_base
<222> LOCATION: (101)..(102)
<223> OTHER INFORMATION: a, c, t, g, unknown or other
<220> FEATURE:
<221> NAME/KEY: modified_base
<222> LOCATION: (177)..(177)
<223> OTHER INFORMATION: a, c, t, g, unknown or other
<220> FEATURE:
<221> NAME/KEY: modified_base
<222> LOCATION: (189)..(189)
<223> OTHER INFORMATION: a, c, t, g, unknown or other
<220> FEATURE:
<221> NAME/KEY: modified_base
<222> LOCATION: (221)..(222)
<223> OTHER INFORMATION: a, c, t, g, unknown or other
<220> FEATURE:
<221> NAME/KEY: modified_base
<222> LOCATION: (253)..(258)
<223> OTHER INFORMATION: a, c, t, g, unknown or other
<220> FEATURE:
<221> NAME/KEY: modified_base
<222> LOCATION: (261)..(261)
<223> OTHER INFORMATION: a, c, t, g, unknown or other
<220> FEATURE:
<221> NAME/KEY: modified_base
<222> LOCATION: (745)..(745)
<223> OTHER INFORMATION: a, c, t, g, unknown or other
<220> FEATURE:
<221> NAME/KEY: modified_base
<222> LOCATION: (771)..(771)
<223> OTHER INFORMATION: a, c, t, g, unknown or other
<220> FEATURE:
<221> NAME/KEY: modified_base
<222> LOCATION: (794)..(794)
<223> OTHER INFORMATION: a, c, t, g, unknown or other
<220> FEATURE:
<221> NAME/KEY: modified_base
<222> LOCATION: (800)..(800)
<223> OTHER INFORMATION: a, c, t, g, unknown or other
<220> FEATURE:
<221> NAME/KEY: modified_base
<222> LOCATION: (810)..(810)
<223> OTHER INFORMATION: a, c, t, g, unknown or other
<220> FEATURE:
<221> NAME/KEY: modified_base
<222> LOCATION: (814)..(816)
<223> OTHER INFORMATION: a, c, t, g, unknown or other

<400> SEQUENCE: 5
attncgccaa gctnncatgc aaaatttnta tttnaangga gacagtcata atgaaatacc      60
tattgcntac nnnnnnncgc tggattgtta ttactcgcgg nncagccggc catggccgag     120
gtgcagctgt tggagtctgg gggaggcttg gtacagcctg gggggtccct gagactntcc     180
tgtgcagcnt ctggattcac ctttagcagc tatgccatga nntgggtccg ccaggctcca     240
gggaaggggc tgnnnnnngt ntcatctatt acgtagacgg gttcgtagac acagtacgca     300
gactccgtga agggcaggtt caccatctcc agagacaatt ccaagaacac gctgtatctg     360
caaatgaaca gcctgagagc cgaggacacg gccgtatatt actgtgcgaa acagcatgat     420
gattttgact actggggcca gggaaccctg gtcaccgtct cgagcggtgg aggcggttca     480
ggcggaggtg gcagcggcgg tggcgggtcg acggacatcc agatgaccca gtctccatcc     540
tccctgtctg catctgtagg agacagagtc accatcactt gccgggcaag tcagagcatt     600
```

```
agcagctatt taaattggta tcagcagaaa ccagggaaag cccctaagct cctgatctat        660
actgcatcca atttgcaaag tggggtccca tcaaggttca gtggcagtgg atctgggaca        720
gatttcactc tcaccatcag cagtntgcaa cctgaagatt ttgcaactta ntactgtcaa        780
cagctggatg tgtntccttn gacgttcggn caannnacca aggtggaaat caa              833
```

```
<210> SEQ ID NO 6
<211> LENGTH: 238
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(22)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (37)..(37)
<223> OTHER INFORMATION: Any amino acid
<220> FEATURE:
<221> NAME/KEY: MOD_RES
<222> LOCATION: (48)..(50)
<223> OTHER INFORMATION: Any amino acid
<220> FEATURE:
<221> NAME/KEY: MOD_RES
<222> LOCATION: (210)..(210)
<223> OTHER INFORMATION: Any amino acid
<220> FEATURE:
<221> NAME/KEY: MOD_RES
<222> LOCATION: (218)..(218)
<223> OTHER INFORMATION: Any amino acid
<220> FEATURE:
<221> NAME/KEY: MOD_RES
<222> LOCATION: (226)..(226)
<223> OTHER INFORMATION: Any amino acid
<220> FEATURE:
<221> NAME/KEY: MOD_RES
<222> LOCATION: (228)..(228)
<223> OTHER INFORMATION: Any amino acid
<220> FEATURE:
<221> NAME/KEY: MOD_RES
<222> LOCATION: (231)..(231)
<223> OTHER INFORMATION: Any amino acid
<220> FEATURE:
<221> NAME/KEY: MOD_RES
<222> LOCATION: (233)..(233)
<223> OTHER INFORMATION: Any amino acid

<400> SEQUENCE: 6

Met Ala Glu Val Gln Leu Leu Glu Ser Gly Gly Gly Leu Val Gln Pro
1               5                   10                  15

Gly Gly Ser Leu Arg Xaa Ser Cys Ala Xaa Ser Gly Phe Thr Phe Ser
            20                  25                  30

Ser Tyr Ala Met Xaa Trp Val Arg Gln Ala Pro Gly Lys Gly Leu Xaa
        35                  40                  45

Xaa Xaa Ser Ser Ile Thr Thr Gly Ser Thr Gln Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln His Asp Asp Phe Asp Tyr Trp Gly Gln Gly Thr Leu Val
            100                 105                 110
```

```
Thr Val Ser Ser Gly Gly Gly Ser Gly Gly Gly Ser Gly Gly
        115                 120                 125

Gly Gly Ser Thr Asp Ile Gln Met Thr Gln Ser Pro Ser Ser Leu Ser
130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Thr Ala Ser Asn Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Xaa Gln Pro Glu Asp Phe Ala Thr Xaa Tyr Cys Gln Gln Leu Asp
    210                 215                 220

Val Xaa Pro Xaa Thr Phe Xaa Gln Xaa Thr Lys Val Glu Ile
225                 230                 235
```

<210> SEQ ID NO 7
<211> LENGTH: 963
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: modified_base
<222> LOCATION: (660)..(660)
<223> OTHER INFORMATION: a, c, t, g, unknown or other
<220> FEATURE:
<221> NAME/KEY: modified_base
<222> LOCATION: (690)..(690)
<223> OTHER INFORMATION: a, c, t, g, unknown or other
<220> FEATURE:
<221> NAME/KEY: modified_base
<222> LOCATION: (763)..(763)
<223> OTHER INFORMATION: a, c, t, g, unknown or other
<220> FEATURE:
<221> NAME/KEY: modified_base
<222> LOCATION: (853)..(853)
<223> OTHER INFORMATION: a, c, t, g, unknown or other
<220> FEATURE:
<221> NAME/KEY: modified_base
<222> LOCATION: (861)..(862)
<223> OTHER INFORMATION: a, c, t, g, unknown or other
<220> FEATURE:
<221> NAME/KEY: modified_base
<222> LOCATION: (872)..(874)
<223> OTHER INFORMATION: a, c, t, g, unknown or other
<220> FEATURE:
<221> NAME/KEY: modified_base
<222> LOCATION: (876)..(877)
<223> OTHER INFORMATION: a, c, t, g, unknown or other
<220> FEATURE:
<221> NAME/KEY: modified_base
<222> LOCATION: (898)..(898)
<223> OTHER INFORMATION: a, c, t, g, unknown or other
<220> FEATURE:
<221> NAME/KEY: modified_base
<222> LOCATION: (912)..(912)
<223> OTHER INFORMATION: a, c, t, g, unknown or other
<220> FEATURE:
<221> NAME/KEY: modified_base
<222> LOCATION: (914)..(916)
<223> OTHER INFORMATION: a, c, t, g, unknown or other
<220> FEATURE:
<221> NAME/KEY: modified_base

```
<222> LOCATION: (954)..(954)
<223> OTHER INFORMATION: a, c, t, g, unknown or other
<220> FEATURE:
<221> NAME/KEY: modified_base
<222> LOCATION: (957)..(958)
<223> OTHER INFORMATION: a, c, t, g, unknown or other

<400> SEQUENCE: 7
gagacagtca tagctagcat gaaaaagant tggctggcgc tggctggttt agttttagcg    60
tttagcgcat cggcggacta caaagaggcc cagccggcca tggacctggg taagaaactg   120
ctggaagctg ctcgtgctgg tcaggacgac gaagttcgta tcctgatggc taacggtgct   180
gacgttaacg ctgacgacta cgaaggttgg actccgctgc acctggctgc tatggttggt   240
cacctggaaa tcgttgaagt tctgctgaag tacggtgctg acgttaacgc tcaggacaaa   300
ttcggtaaga ccgctttcga catctccatc gacaacggta acgaggacct ggctgaaatc   360
ctgcaagcgg ccgcacatca tcatcaccat cacgggccg cagaacaaaa actcatctca   420
gaagaggatc tgaatggggc cgcatagact gttgaaagtt gtttagcaaa acctcataca   480
gaaaattcat ttactaacgt ctggaaagac gacaaaactt tagatcgtta cgctaactat   540
gagggctgtc tgtggaatgc tacaggcgtt gtggtttgta ctggtgacga aactcagtgt   600
tacggtacat gggttcctat tgggcttgct atccctgaaa atgagggtgg tggctctgan   660
ggtggcggtt ctgagggtgg cggttctgan ggtggcggta ctaaacctcc tgagtacggt   720
gatacaccta ttccgggcta tacttatatc aaccctctcg acngcactta tccgcctggt   780
actgagcaaa accccgctaa tcctaatccc ttctcttgag gagtctcagc ctcttaatac   840
tttcatgttt canaataata nnttccgaaa tnnncnnggt gcattaactg tttatacngg   900
cactgttact cnannnactg accccgtttt aaaacttatt accagtacac tccntgnnat   960
cat                                                                 963
```

<210> SEQ ID NO 8
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid

<400> SEQUENCE: 8

Met Lys Lys Xaa Trp Leu Ala Leu Ala Gly Leu Val Leu Ala Phe Ser
1               5                  10                  15

Ala Ser Ala Asp Tyr Lys Glu Ala Gln Pro Ala Met Asp Leu Gly Lys
            20                  25                  30

Lys Leu Leu Glu Ala Ala Arg Ala Gly Gln Asp Asp Glu Val Arg Ile
        35                  40                  45

Leu Met Ala Asn Gly Ala Asp Val Asn Ala Asp Tyr Glu Gly Trp
    50                  55                  60

Thr Pro Leu His Leu Ala Ala Met Val Gly His Leu Glu Ile Val Glu
65                  70                  75                  80

Val Leu Leu Lys Tyr Gly Ala Asp Val Asn Ala Gln Asp Lys Phe Gly
                85                  90                  95

Lys Thr Ala Phe Asp Ile Ser Ile Asp Asn Gly Asn Glu Asp Leu Ala
            100                 105                 110

Glu Ile Leu Gln Ala Ala Ala His His His His His His Gly Ala Ala
             115                 120                 125

Glu Gln Lys Leu Ile Ser Glu Glu Asp Leu Asn Gly Ala Ala
     130                 135                 140

<210> SEQ ID NO 9
<211> LENGTH: 890
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (67)..(67)
<223> OTHER INFORMATION: a, c, t, g, unknown or other
<220> FEATURE:
<221> NAME/KEY: modified_base
<222> LOCATION: (778)..(778)
<223> OTHER INFORMATION: a, c, t, g, unknown or other
<220> FEATURE:
<221> NAME/KEY: modified_base
<222> LOCATION: (799)..(799)
<223> OTHER INFORMATION: a, c, t, g, unknown or other
<220> FEATURE:
<221> NAME/KEY: modified_base
<222> LOCATION: (814)..(814)
<223> OTHER INFORMATION: a, c, t, g, unknown or other
<220> FEATURE:
<221> NAME/KEY: modified_base
<222> LOCATION: (822)..(823)
<223> OTHER INFORMATION: a, c, t, g, unknown or other
<220> FEATURE:
<221> NAME/KEY: modified_base
<222> LOCATION: (843)..(844)
<223> OTHER INFORMATION: a, c, t, g, unknown or other
<220> FEATURE:
<221> NAME/KEY: modified_base
<222> LOCATION: (866)..(867)
<223> OTHER INFORMATION: a, c, t, g, unknown or other

<400> SEQUENCE: 9
ttcaggagan agtcntaatg aaatacctat tgcctacggc agccgctgga ttgttattac      60
tcgcggncca gccggccatg gccgaggtgc agctgttgga gtctggggga ggcttggtac     120
agcctggggg gtccctgaga ctctcctgtg cagcctctgg attcaccttt agcagctatg     180
ccatgagctg ggtccgccag gctccaggga aggggctgga gtgggtctca ggtatttcta     240
ataatggtag taatacaact tacgcagact ccgtgaaggg ccggttcacc atctccagag     300
acaattccaa gaacacgctg tatctgcaaa tgaacagcct gagagccgag gacacggccg     360
tatattactg tgcgaaagct tcttatactt ttgactactg gggccaggga accctggtca     420
ccgtctcgag cggtggaggc ggttcaggcg gaggtggcag cggcggtggc gggtcgacgg     480
acatccagat gacccagtct ccatcctccc tgtctgcatc tgtaggagac agagtcacca     540
tcacttgccg ggcaagtcag agcattagca gctatttaaa ttggtatcag cagaaaccag     600
ggaaagcccc taagctcctg atctatagtg catcctcttt gcaaagtggg gtcccatcaa     660
ggttcagtgg cagtggatct gggacagatt tcactctcac catcagcagt ctgcaacctg     720
aagattttgc aacttactac tgtcaacagt attctggttc tcctgctacg ttcggccnag     780

```
ggaccaaggt ggaaatcana cgggcggccg cacntcatca tnnccatcac ggggccgcag    840
aannaaaact catctcagaa gagganntga atggggccgc atagactgtt               890
```

<210> SEQ ID NO 10
<211> LENGTH: 283
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (254)..(254)
<223> OTHER INFORMATION: Any amino acid
<220> FEATURE:
<221> NAME/KEY: MOD_RES
<222> LOCATION: (261)..(261)
<223> OTHER INFORMATION: Any amino acid
<220> FEATURE:
<221> NAME/KEY: MOD_RES
<222> LOCATION: (266)..(266)
<223> OTHER INFORMATION: Any amino acid
<220> FEATURE:
<221> NAME/KEY: MOD_RES
<222> LOCATION: (269)..(269)
<223> OTHER INFORMATION: Any amino acid
<220> FEATURE:
<221> NAME/KEY: MOD_RES
<222> LOCATION: (276)..(276)
<223> OTHER INFORMATION: Any amino acid
<220> FEATURE:
<221> NAME/KEY: MOD_RES
<222> LOCATION: (283)..(283)
<223> OTHER INFORMATION: Any amino acid

<400> SEQUENCE: 10

Met Lys Tyr Leu Leu Pro Thr Ala Ala Ala Gly Leu Leu Leu Leu Ala
1               5                   10                  15

Xaa Gln Pro Ala Met Ala Glu Val Gln Leu Leu Glu Ser Gly Gly Gly
                20                  25                  30

Leu Val Gln Pro Gly Gly Ser Leu Arg Leu Ser Cys Ala Ala Ser Gly
            35                  40                  45

Phe Thr Phe Ser Ser Tyr Ala Met Ser Trp Val Arg Gln Ala Pro Gly
    50                  55                  60

Lys Gly Leu Glu Trp Val Ser Gly Ile Ser Asn Asn Gly Ser Asn Thr
65                  70                  75                  80

Thr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Ala Ser Tyr Thr Phe Asp Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Ser Thr Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

```
Lys Pro Gly Lys Ala Pro Lys Leu Leu Ile Tyr Ser Ala Ser Ser Leu
            195                 200                 205

Gln Ser Gly Val Pro Ser Arg Phe Ser Gly Ser Gly Ser Gly Thr Asp
        210                 215                 220

Phe Thr Leu Thr Ile Ser Ser Leu Gln Pro Glu Asp Phe Ala Thr Tyr
225                 230                 235                 240

Tyr Cys Gln Gln Tyr Ser Gly Ser Pro Ala Thr Phe Gly Xaa Gly Thr
                245                 250                 255

Lys Val Glu Ile Xaa Arg Ala Ala Ala Xaa His His Xaa His His Gly
            260                 265                 270

Ala Ala Glu Xaa Lys Leu Ile Ser Glu Glu Xaa
            275                 280
```

<210> SEQ ID NO 11
<211> LENGTH: 883
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: modified_base
<222> LOCATION: (51)..(51)
<223> OTHER INFORMATION: a, c, t, g, unknown or other
<220> FEATURE:
<221> NAME/KEY: modified_base
<222> LOCATION: (53)..(54)
<223> OTHER INFORMATION: a, c, t, g, unknown or other
<220> FEATURE:
<221> NAME/KEY: modified_base
<222> LOCATION: (86)..(86)
<223> OTHER INFORMATION: a, c, t, g, unknown or other
<220> FEATURE:
<221> NAME/KEY: modified_base
<222> LOCATION: (154)..(154)
<223> OTHER INFORMATION: a, c, t, g, unknown or other
<220> FEATURE:
<221> NAME/KEY: modified_base
<222> LOCATION: (172)..(172)
<223> OTHER INFORMATION: a, c, t, g, unknown or other
<220> FEATURE:
<221> NAME/KEY: modified_base
<222> LOCATION: (267)..(267)
<223> OTHER INFORMATION: a, c, t, g, unknown or other
<220> FEATURE:
<221> NAME/KEY: modified_base
<222> LOCATION: (434)..(434)
<223> OTHER INFORMATION: a, c, t, g, unknown or other
<220> FEATURE:
<221> NAME/KEY: modified_base
<222> LOCATION: (447)..(447)
<223> OTHER INFORMATION: a, c, t, g, unknown or other
<220> FEATURE:
<221> NAME/KEY: modified_base
<222> LOCATION: (529)..(529)
<223> OTHER INFORMATION: a, c, t, g, unknown or other
<220> FEATURE:
<221> NAME/KEY: modified_base
<222> LOCATION: (546)..(546)
<223> OTHER INFORMATION: a, c, t, g, unknown or other
<220> FEATURE:

```
<221> NAME/KEY: modified_base
<222> LOCATION: (555)..(556)
<223> OTHER INFORMATION: a, c, t, g, unknown or other
<220> FEATURE:
<221> NAME/KEY: modified_base
<222> LOCATION: (581)..(581)
<223> OTHER INFORMATION: a, c, t, g, unknown or other
<220> FEATURE:
<221> NAME/KEY: modified_base
<222> LOCATION: (584)..(584)
<223> OTHER INFORMATION: a, c, t, g, unknown or other
<220> FEATURE:
<221> NAME/KEY: modified_base
<222> LOCATION: (620)..(620)
<223> OTHER INFORMATION: a, c, t, g, unknown or other
<220> FEATURE:
<221> NAME/KEY: modified_base
<222> LOCATION: (639)..(639)
<223> OTHER INFORMATION: a, c, t, g, unknown or other
<220> FEATURE:
<221> NAME/KEY: modified_base
<222> LOCATION: (645)..(645)
<223> OTHER INFORMATION: a, c, t, g, unknown or other
<220> FEATURE:
<221> NAME/KEY: modified_base
<222> LOCATION: (672)..(672)
<223> OTHER INFORMATION: a, c, t, g, unknown or other
<220> FEATURE:
<221> NAME/KEY: modified_base
<222> LOCATION: (700)..(700)
<223> OTHER INFORMATION: a, c, t, g, unknown or other
<220> FEATURE:
<221> NAME/KEY: modified_base
<222> LOCATION: (734)..(734)
<223> OTHER INFORMATION: a, c, t, g, unknown or other
<220> FEATURE:
<221> NAME/KEY: modified_base
<222> LOCATION: (754)..(755)
<223> OTHER INFORMATION: a, c, t, g, unknown or other
<220> FEATURE:
<221> NAME/KEY: modified_base
<222> LOCATION: (764)..(764)
<223> OTHER INFORMATION: a, c, t, g, unknown or other
<220> FEATURE:
<221> NAME/KEY: modified_base
<222> LOCATION: (766)..(766)
<223> OTHER INFORMATION: a, c, t, g, unknown or other
<220> FEATURE:
<221> NAME/KEY: modified_base
<222> LOCATION: (785)..(785)
<223> OTHER INFORMATION: a, c, t, g, unknown or other
<220> FEATURE:
<221> NAME/KEY: modified_base
<222> LOCATION: (787)..(788)
<223> OTHER INFORMATION: a, c, t, g, unknown or other
<220> FEATURE:
<221> NAME/KEY: modified_base
<222> LOCATION: (797)..(797)
<223> OTHER INFORMATION: a, c, t, g, unknown or other
<220> FEATURE:
<221> NAME/KEY: modified_base
<222> LOCATION: (799)..(799)
<223> OTHER INFORMATION: a, c, t, g, unknown or other
<220> FEATURE:
<221> NAME/KEY: modified_base
<222> LOCATION: (802)..(802)
<223> OTHER INFORMATION: a, c, t, g, unknown or other
<220> FEATURE:
<221> NAME/KEY: modified_base
<222> LOCATION: (815)..(815)
<223> OTHER INFORMATION: a, c, t, g, unknown or other
<220> FEATURE:
<221> NAME/KEY: modified_base
<222> LOCATION: (817)..(817)
<223> OTHER INFORMATION: a, c, t, g, unknown or other
<220> FEATURE:
<221> NAME/KEY: modified_base
<222> LOCATION: (819)..(823)
<223> OTHER INFORMATION: a, c, t, g, unknown or other
```

```
<220> FEATURE:
<221> NAME/KEY: modified_base
<222> LOCATION: (826)..(826)
<223> OTHER INFORMATION: a, c, t, g, unknown or other
<220> FEATURE:
<221> NAME/KEY: modified_base
<222> LOCATION: (828)..(830)
<223> OTHER INFORMATION: a, c, t, g, unknown or other
<220> FEATURE:
<221> NAME/KEY: modified_base
<222> LOCATION: (837)..(837)
<223> OTHER INFORMATION: a, c, t, g, unknown or other
<220> FEATURE:
<221> NAME/KEY: modified_base
<222> LOCATION: (839)..(839)
<223> OTHER INFORMATION: a, c, t, g, unknown or other
<220> FEATURE:
<221> NAME/KEY: modified_base
<222> LOCATION: (854)..(855)
<223> OTHER INFORMATION: a, c, t, g, unknown or other
<220> FEATURE:
<221> NAME/KEY: modified_base
<222> LOCATION: (860)..(860)
<223> OTHER INFORMATION: a, c, t, g, unknown or other
<220> FEATURE:
<221> NAME/KEY: modified_base
<222> LOCATION: (868)..(868)
<223> OTHER INFORMATION: a, c, t, g, unknown or other
<220> FEATURE:
<221> NAME/KEY: modified_base
<222> LOCATION: (872)..(874)
<223> OTHER INFORMATION: a, c, t, g, unknown or other
<220> FEATURE:
<221> NAME/KEY: modified_base
<222> LOCATION: (876)..(876)
<223> OTHER INFORMATION: a, c, t, g, unknown or other
<220> FEATURE:
<221> NAME/KEY: modified_base
<222> LOCATION: (880)..(880)
<223> OTHER INFORMATION: a, c, t, g, unknown or other

<400> SEQUENCE: 11
ttcagganan agtcataatg aantacctat tgcctacggc agccgctgga ntnntattac    60
tcgcggccca gccggccatg gcccangtgc agctggtgga gtctggggga ggcgtggtcc   120
agcctgggag gtccctgaga ctctcctgtg cagnctccgg attcaccttt ancagctatg   180
acatgggctg ggtccgccag gctccaggga aggggctgga gtgggtctca agtattagtg   240
gtagtggtcc taccatgaac tacgcanact ctgtgaaggg ccgattcacc gtctccagag   300
acaattccaa gaacacgctg tatctgcaaa tggacagcct gagagccgag gacacggccg   360
tatattactg tgcgaaaggg ggtacggact ttgactactg gggccagggc accctggtca   420
ccgtctcctc aggnggaggc ggttcangcg gaggtggctc tggcggtggc ggatcgtctg   480
agctgactca ggaccctgct gtgtctgtgg ccttgggaca dacagtcanc atcacatgcc   540
aagganacag cctcnnaacc tattatgcaa gctggtacca ncanaagcca ggacaggccc   600
ctgtacttgt catctatggn aaaaacaacc ggccctcang gatcncagac cgattctctg   660
gctccagctc angaaacaca gcttccttga ccatcactgn ggctcaggcg gaagatgagg   720
ctgactatta ctgnaactcc cgggacagca gtgnnaacca tctnangagt gttcggcgga   780
gggancnngc tgaccgncnt angtgcggcc gcagnancnn nnnctncnnn tcagaanang   840
atctgaatgg ggcnncatan actgttgnaa annngnttan caa                    883

<210> SEQ ID NO 12
<211> LENGTH: 255
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (46)..(46)
<223> OTHER INFORMATION: Any amino acid
<220> FEATURE:
<221> NAME/KEY: MOD_RES
<222> LOCATION: (52)..(52)
<223> OTHER INFORMATION: Any amino acid
<220> FEATURE:
<221> NAME/KEY: MOD_RES
<222> LOCATION: (84)..(84)
<223> OTHER INFORMATION: Any amino acid
<220> FEATURE:
<221> NAME/KEY: MOD_RES
<222> LOCATION: (139)..(139)
<223> OTHER INFORMATION: Any amino acid
<220> FEATURE:
<221> NAME/KEY: MOD_RES
<222> LOCATION: (144)..(144)
<223> OTHER INFORMATION: Any amino acid
<220> FEATURE:
<221> NAME/KEY: MOD_RES
<222> LOCATION: (171)..(171)
<223> OTHER INFORMATION: Any amino acid
<220> FEATURE:
<221> NAME/KEY: MOD_RES
<222> LOCATION: (177)..(177)
<223> OTHER INFORMATION: Any amino acid
<220> FEATURE:
<221> NAME/KEY: MOD_RES
<222> LOCATION: (180)..(180)
<223> OTHER INFORMATION: Any amino acid
<220> FEATURE:
<221> NAME/KEY: MOD_RES
<222> LOCATION: (188)..(189)
<223> OTHER INFORMATION: Any amino acid
<220> FEATURE:
<221> NAME/KEY: MOD_RES
<222> LOCATION: (201)..(201)
<223> OTHER INFORMATION: Any amino acid
<220> FEATURE:
<221> NAME/KEY: MOD_RES
<222> LOCATION: (208)..(208)
<223> OTHER INFORMATION: Any amino acid
<220> FEATURE:
<221> NAME/KEY: MOD_RES
<222> LOCATION: (210)..(210)
<223> OTHER INFORMATION: Any amino acid
<220> FEATURE:
<221> NAME/KEY: MOD_RES
<222> LOCATION: (219)..(219)
<223> OTHER INFORMATION: Any amino acid
<220> FEATURE:
<221> NAME/KEY: MOD_RES
<222> LOCATION: (228)..(228)
<223> OTHER INFORMATION: Any amino acid
<220> FEATURE:
<221> NAME/KEY: MOD_RES
<222> LOCATION: (239)..(239)
<223> OTHER INFORMATION: Any amino acid
<220> FEATURE:
<221> NAME/KEY: MOD_RES
<222> LOCATION: (246)..(246)
<223> OTHER INFORMATION: Any amino acid
<220> FEATURE:
```

```
<221> NAME/KEY: MOD_RES
<222> LOCATION: (249)..(250)
<223> OTHER INFORMATION: Any amino acid

<400> SEQUENCE: 12

Met Xaa Tyr Leu Leu Pro Thr Ala Ala Ala Gly Xaa Xaa Leu Leu Ala
1               5                   10                  15

Ala Gln Pro Ala Met Ala Xaa Val Gln Leu Val Glu Ser Gly Gly Gly
            20                  25                  30

Val Val Gln Pro Gly Arg Ser Leu Arg Leu Ser Cys Ala Xaa Ser Gly
        35                  40                  45

Phe Thr Phe Xaa Ser Tyr Asp Met Gly Trp Val Arg Gln Ala Pro Gly
    50                  55                  60

Lys Gly Leu Glu Trp Val Ser Ile Ser Gly Ser Gly Pro Thr Met
65                  70                  75                  80

Asn Tyr Ala Xaa Ser Val Lys Gly Arg Phe Thr Val Ser Arg Asp Asn
                85                  90                  95

Ser Lys Asn Thr Leu Tyr Leu Gln Met Asp Ser Leu Arg Ala Glu Asp
            100                 105                 110

Thr Ala Val Tyr Tyr Cys Ala Lys Gly Gly Thr Asp Phe Asp Tyr Trp
        115                 120                 125

Gly Gln Gly Thr Leu Val Thr Val Ser Ser Xaa Gly Gly Gly Ser Xaa
    130                 135                 140

Gly Gly Gly Ser Gly Gly Gly Ser Ser Glu Leu Thr Gln Asp Pro
145                 150                 155                 160

Ala Val Ser Val Ala Leu Gly Gln Thr Val Xaa Ile Thr Cys Gln Gly
                165                 170                 175

Xaa Ser Leu Xaa Thr Tyr Tyr Ala Ser Trp Tyr Xaa Xaa Lys Pro Gly
            180                 185                 190

Gln Ala Pro Val Leu Val Ile Tyr Xaa Lys Asn Asn Arg Pro Ser Xaa
        195                 200                 205

Ile Xaa Asp Arg Phe Ser Gly Ser Ser Xaa Asn Thr Ala Ser Leu
    210                 215                 220

Thr Ile Thr Xaa Ala Gln Ala Glu Asp Glu Ala Asp Tyr Tyr Xaa Asn
225                 230                 235                 240

Ser Arg Asp Ser Ser Xaa Asn His Xaa Xaa Ser Val Arg Arg Arg
                245                 250                 255

<210> SEQ ID NO 13
<211> LENGTH: 854
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (651)..(651)
<223> OTHER INFORMATION: a, c, t, g, unknown or other
<220> FEATURE:
<221> NAME/KEY: modified_base
<222> LOCATION: (751)..(752)
<223> OTHER INFORMATION: a, c, t, g, unknown or other
<220> FEATURE:
```

```
<221> NAME/KEY: modified_base
<222> LOCATION: (760)..(760)
<223> OTHER INFORMATION: a, c, t, g, unknown or other
<220> FEATURE:
<221> NAME/KEY: modified_base
<222> LOCATION: (766)..(767)
<223> OTHER INFORMATION: a, c, t, g, unknown or other
<220> FEATURE:
<221> NAME/KEY: modified_base
<222> LOCATION: (776)..(776)
<223> OTHER INFORMATION: a, c, t, g, unknown or other
<220> FEATURE:
<221> NAME/KEY: modified_base
<222> LOCATION: (778)..(778)
<223> OTHER INFORMATION: a, c, t, g, unknown or other
<220> FEATURE:
<221> NAME/KEY: modified_base
<222> LOCATION: (780)..(780)
<223> OTHER INFORMATION: a, c, t, g, unknown or other
<220> FEATURE:
<221> NAME/KEY: modified_base
<222> LOCATION: (787)..(789)
<223> OTHER INFORMATION: a, c, t, g, unknown or other
<220> FEATURE:
<221> NAME/KEY: modified_base
<222> LOCATION: (791)..(794)
<223> OTHER INFORMATION: a, c, t, g, unknown or other
<220> FEATURE:
<221> NAME/KEY: modified_base
<222> LOCATION: (801)..(802)
<223> OTHER INFORMATION: a, c, t, g, unknown or other
<220> FEATURE:
<221> NAME/KEY: modified_base
<222> LOCATION: (816)..(817)
<223> OTHER INFORMATION: a, c, t, g, unknown or other
<220> FEATURE:
<221> NAME/KEY: modified_base
<222> LOCATION: (821)..(821)
<223> OTHER INFORMATION: a, c, t, g, unknown or other
<220> FEATURE:
<221> NAME/KEY: modified_base
<222> LOCATION: (824)..(828)
<223> OTHER INFORMATION: a, c, t, g, unknown or other
<220> FEATURE:
<221> NAME/KEY: modified_base
<222> LOCATION: (831)..(831)
<223> OTHER INFORMATION: a, c, t, g, unknown or other
<220> FEATURE:
<221> NAME/KEY: modified_base
<222> LOCATION: (833)..(833)
<223> OTHER INFORMATION: a, c, t, g, unknown or other
<220> FEATURE:
<221> NAME/KEY: modified_base
<222> LOCATION: (836)..(839)
<223> OTHER INFORMATION: a, c, t, g, unknown or other

<400> SEQUENCE: 13
ttcaggagan agtcntaatg aaatacctat tgcctacggc agccgctgga ttgttattac      60
tcgcggccca gccggccatg gccgaggtgc agctgttgga gtctggggga ggcttggtac     120
agcctggggg gtccctgaga ctctcctgtg cagcctctgg attcaccttt agcagctatg     180
ccatgagctg ggtccgccag gctccaggga aggggctgga gtgggtctca gctattacta     240
atgatggtgc tggtacaact tacgcagact ccgtgaaggg ccggttcacc atctccagag     300
acaattccaa gaacacgctg tatctgcaaa tgaacagcct gagagccgag gacacggccg     360
tatattactg tgcgaaatct tatactggtt ttgactactg gggccaggga accctggtca     420
ccgtctcgag cggtggaggc ggttcaggcg gaggtggcag cggcggtggc gggtcgacgg     480
acatccagat gacccaatct ccatcctccc tgtctgcatc tgtaggagac agagtcacca     540
tcacttgccg ggcaagtcag agcattagca gctatttaaa ttggtatcag cagaaaccag     600
ggaaagcccc taagctcctg atctatactg catccacttt gcaaagtggg ntcccattaa     660
```

```
ggttcagtgg cagtggatct gggacagatt tcactctcac catcagcagt ctgcaacctg    720 aagatttgc aacttactac tgtcaacaga nntatgctan tcctannacg ttcggncnan     780
gggaccnnng nnnnaaatca nncgggcggc cgcacnncat natnnnnnat ncncgnnnnc    840
gcagaacaaa actc                                                      854
```

```
<210> SEQ ID NO 14
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (212)..(212)
<223> OTHER INFORMATION: Any amino acid
<220> FEATURE:
<221> NAME/KEY: MOD_RES
<222> LOCATION: (245)..(245)
<223> OTHER INFORMATION: Any amino acid
<220> FEATURE:
<221> NAME/KEY: MOD_RES
<222> LOCATION: (248)..(248)
<223> OTHER INFORMATION: Any amino acid
<220> FEATURE:
<221> NAME/KEY: MOD_RES
<222> LOCATION: (250)..(250)
<223> OTHER INFORMATION: Any amino acid

<400> SEQUENCE: 14

Met Lys Tyr Leu Leu Pro Thr Ala Ala Ala Gly Leu Leu Leu Leu Ala
1               5                   10                  15

Ala Gln Pro Ala Met Ala Glu Val Gln Leu Leu Glu Ser Gly Gly Gly
                20                  25                  30

Leu Val Gln Pro Gly Gly Ser Leu Arg Leu Ser Cys Ala Ala Ser Gly
            35                  40                  45

Phe Thr Phe Ser Ser Tyr Ala Met Ser Trp Val Arg Gln Ala Pro Gly
        50                  55                  60

Lys Gly Leu Glu Trp Val Ser Ala Ile Thr Asn Asp Gly Ala Gly Thr
65                  70                  75                  80

Thr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Ser Tyr Thr Gly Phe Asp Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Thr Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Thr Ala Ser Thr Leu
        195                 200                 205

Gln Ser Gly Xaa Pro Leu Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
```

```
                    225                 230                 235                 240

Tyr Cys Gln Gln Xaa Tyr Ala Xaa Pro Xaa Thr Phe
                245                 250

<210> SEQ ID NO 15
<211> LENGTH: 972
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (11)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (32)..(32)
<223> OTHER INFORMATION: a, c, t, g, unknown or other
<220> FEATURE:
<221> NAME/KEY: modified_base
<222> LOCATION: (749)..(749)
<223> OTHER INFORMATION: a, c, t, g, unknown or other
<220> FEATURE:
<221> NAME/KEY: modified_base
<222> LOCATION: (850)..(850)
<223> OTHER INFORMATION: a, c, t, g, unknown or other
<220> FEATURE:
<221> NAME/KEY: modified_base
<222> LOCATION: (857)..(857)
<223> OTHER INFORMATION: a, c, t, g, unknown or other
<220> FEATURE:
<221> NAME/KEY: modified_base
<222> LOCATION: (908)..(909)
<223> OTHER INFORMATION: a, c, t, g, unknown or other
<220> FEATURE:
<221> NAME/KEY: modified_base
<222> LOCATION: (912)..(913)
<223> OTHER INFORMATION: a, c, t, g, unknown or other
<220> FEATURE:
<221> NAME/KEY: modified_base
<222> LOCATION: (918)..(918)
<223> OTHER INFORMATION: a, c, t, g, unknown or other
<220> FEATURE:
<221> NAME/KEY: modified_base
<222> LOCATION: (930)..(930)
<223> OTHER INFORMATION: a, c, t, g, unknown or other
<220> FEATURE:
<221> NAME/KEY: modified_base
<222> LOCATION: (942)..(942)
<223> OTHER INFORMATION: a, c, t, g, unknown or other
<220> FEATURE:
<221> NAME/KEY: modified_base
<222> LOCATION: (944)..(944)
<223> OTHER INFORMATION: a, c, t, g, unknown or other
<220> FEATURE:
<221> NAME/KEY: modified_base
<222> LOCATION: (948)..(948)
<223> OTHER INFORMATION: a, c, t, g, unknown or other
<220> FEATURE:
<221> NAME/KEY: modified_base
<222> LOCATION: (950)..(951)
<223> OTHER INFORMATION: a, c, t, g, unknown or other
<220> FEATURE:
<221> NAME/KEY: modified_base
```

```
<222> LOCATION: (954)..(954)
<223> OTHER INFORMATION: a, c, t, g, unknown or other
<220> FEATURE:
<221> NAME/KEY: modified_base
<222> LOCATION: (962)..(962)
<223> OTHER INFORMATION: a, c, t, g, unknown or other
<220> FEATURE:
<221> NAME/KEY: modified_base
<222> LOCATION: (968)..(968)
<223> OTHER INFORMATION: a, c, t, g, unknown or other

<400> SEQUENCE: 15
ctangcgncc nnttnagatc ctcttctgag angagttttt gttctgcggc cccgtgatgg      60
tgatgatgat gtgcggccgc ccgtttgatt tccaccttgg tcccttggcc gaacgtcgca     120
ggagtctgat gagtctgttg acagtagtaa gttgcaaaat cttcaggttg cagactgctg     180
atggtgagag tgaaatctgt cccagatcca ctgccactga accttgatgg daccccactt     240
tgcaactggg atgccggata gatcaggagc ttaggggctt tccctggttt ctgctgatac     300
caatttaaat agctgctaat gctctgactt gcccggcaag tgatggtgac tctgtctcct     360
acagatgcag acagggagga tggagactgg gtcatctgga tgtccgtcga cccgccaccg     420
ccgctgccac ctccgcctga accgcctcca ccgctcgaga cggtgaccag ggttccctgg     480
ccccagtagt caaaagacca aaactgtttc gcacagtaat atacggccgt gtcctcggct     540
ctcaggctgt tcatttgcag atacagcgtg ttcttggaat tgtctctgga gatggtgaac     600
cggcccttca cggagtctgc gtacgttgtc ggcggaccct gcttcgcaat atctgagacc     660
cactccagcc ccttcctgg agcctggcgg acccagctca tggcatagct gctaaaggtg     720
aatccagagg ctgcacagga gagtctcang accccccag gctgtaccaa gcctcccca      780
gactccaaca gctgcacctc ggccatggcc ggctgggccg cgagtaataa caatccagcg     840
gctgccgtan gcaatangta tttcattatg actgtctcct tgaaatagaa tttgcatgca     900
agcttggnnt annatggnca tagctgtttn ctgtgtgaaa tngntatncn ntcncaattc     960
cncacaanat ac                                                         972

<210> SEQ ID NO 16
<211> LENGTH: 283
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (40)..(40)
<223> OTHER INFORMATION: Any amino acid
<220> FEATURE:
<221> NAME/KEY: MOD_RES
<222> LOCATION: (279)..(279)
<223> OTHER INFORMATION: Any amino acid

<400> SEQUENCE: 16

Met Lys Tyr Xaa Leu Xaa Thr Ala Ala Ala Gly Leu Leu Leu Leu Ala
1               5                   10                  15

Ala Gln Pro Ala Met Ala Glu Val Gln Leu Leu Glu Ser Gly Gly Gly
            20                  25                  30
```

Leu Val Gln Pro Gly Gly Ser Xaa Arg Leu Ser Cys Ala Ala Ser Gly
            35                  40                  45

Phe Thr Phe Ser Ser Tyr Ala Met Ser Trp Val Arg Gln Ala Pro Gly
        50                  55                  60

Lys Gly Leu Glu Trp Val Ser Asp Ile Ala Lys Gln Gly Pro Pro Thr
65                  70                  75                  80

Thr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Gln Phe Trp Ser Phe Asp Tyr Trp
        115                 120                 125

Gly Gln Gly Thr Leu Val Thr Val Ser Gly Gly Gly Gly Ser Gly
    130                 135                 140

Gly Gly Gly Ser Gly Gly Gly Ser Thr Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Pro Ala Ser Gln Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Thr His Gln Thr Pro Ala Thr Phe Gly Gln Gly Thr
                245                 250                 255

Lys Val Glu Ile Lys Arg Ala Ala Ala His His His His His His Gly
            260                 265                 270

Ala Ala Glu Gln Lys Leu Xaa Ser Glu Glu Asp
        275                 280

<210> SEQ ID NO 17
<211> LENGTH: 980
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other
<220> FEATURE:
<221> NAME/KEY: modified_base
<222> LOCATION: (739)..(739)
<223> OTHER INFORMATION: a, c, t, g, unknown or other
<220> FEATURE:
<221> NAME/KEY: modified_base
<222> LOCATION: (840)..(840)
<223> OTHER INFORMATION: a, c, t, g, unknown or other
<220> FEATURE:
<221> NAME/KEY: modified_base
<222> LOCATION: (880)..(880)
<223> OTHER INFORMATION: a, c, t, g, unknown or other
<220> FEATURE:
<221> NAME/KEY: modified_base
<222> LOCATION: (903)..(903)
<223> OTHER INFORMATION: a, c, t, g, unknown or other
<220> FEATURE:
<221> NAME/KEY: modified_base
<222> LOCATION: (910)..(910)
<223> OTHER INFORMATION: a, c, t, g, unknown or other
<220> FEATURE:
<221> NAME/KEY: modified_base
<222> LOCATION: (942)..(942)
<223> OTHER INFORMATION: a, c, t, g, unknown or other
<220> FEATURE:
<221> NAME/KEY: modified_base
<222> LOCATION: (950)..(950)
<223> OTHER INFORMATION: a, c, t, g, unknown or other
<220> FEATURE:
<221> NAME/KEY: modified_base
<222> LOCATION: (955)..(955)
<223> OTHER INFORMATION: a, c, t, g, unknown or other
<220> FEATURE:
<221> NAME/KEY: modified_base
<222> LOCATION: (957)..(957)
<223> OTHER INFORMATION: a, c, t, g, unknown or other
<220> FEATURE:
<221> NAME/KEY: modified_base
<222> LOCATION: (961)..(961)
<223> OTHER INFORMATION: a, c, t, g, unknown or other
<220> FEATURE:
<221> NAME/KEY: modified_base
<222> LOCATION: (970)..(970)
<223> OTHER INFORMATION: a, c, t, g, unknown or other
<220> FEATURE:
<221> NAME/KEY: modified_base
<222> LOCATION: (978)..(978)
<223> OTHER INFORMATION: a, c, t, g, unknown or other

<400> SEQUENCE: 17

```
cattcngatc ctcttctgag angagttttt gttctgcggc cccgtgatgg tgatgatgat      60
gtgcggccgc ccgtttgatt tccaccttgg tcccttggcc gaacgtaata ggagacggat     120
gcgactgttg acagtagtaa gttgcaaaat cttcaggttg cagactgctg atggtgagag     180
tgaaatctgt cccagatcca ctgccactga accttgatgg dcccccactt tgcaaattgg     240
atgccctata gatcaggagc ttaggggctt tccctggttt ctgctgatac caatttaaat     300
agctgctaat gctctgactt gcccggcaag tgatggtgac tctgtctcct acagatgcag     360
acagggagga tggagactgg gtcatctgga tgtccgtcga cccgccaccg ccgctgccac     420
ctccgcctga accgcctcca ccgctcgaga cggtgaccag ggttccctgg ccccagtagt     480
caaacgccgt ccaacgtttc gcacagtaat atacggccgt gtcctcggct tcaggctgt      540
tcatttgcag atacagcgtg ttcttggaat tgtctctgga gatggtgaac cggcccttca     600
cggagtctgc gtaaattgtc ggactaccac ccccagcaat cgatgagacc cactccagcc     660
ccttccctgg agcctggcgg acccagctca tggcatagct gctaaaggtg aatccagagg     720
ctgcacagga gagtctcang acccccccag gctgtaccaa gctcccccca gactccaaca     780
gctgcacctc ggccatggcc ggctgggccg cgagtaataa caatccagcg gctgccgtan     840
gcaataggta tttcattatg actgtctcct tgaaatagan tttgcatgca agcttggcgt     900
aantcatggn catagctgtt tcctgtgtga aattgttatc cnctcacaan ttccncncaa     960
ncatacgaan cccggaangc                                                 980
```

<210> SEQ ID NO 18
<211> LENGTH: 302
<212> TYPE: PRT
<213> ORGANISM: Artificial Sequence
<220> FEATURE:
<223> OTHER INFORMATION: Description of Artificial Sequence: Synthetic polypeptide

```
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (59)..(59)
<223> OTHER INFORMATION: Any amino acid
<220> FEATURE:
<221> NAME/KEY: MOD_RES
<222> LOCATION: (298)..(298)
<223> OTHER INFORMATION: Any amino acid

<400> SEQUENCE: 18

Met Xaa Met Xaa Tyr Ala Lys Leu Ala Cys Lys Xaa Tyr Phe Lys Glu
1               5                   10                  15

Thr Val Ile Met Lys Tyr Leu Leu Xaa Thr Ala Ala Gly Leu Leu
            20                  25                  30

Leu Leu Ala Ala Gln Pro Ala Met Ala Glu Val Gln Leu Leu Glu Ser
        35                  40                  45

Gly Gly Gly Leu Val Gln Pro Gly Gly Ser Xaa Arg Leu Ser Cys Ala
50                  55                  60

Ala Ser Gly Phe Thr Phe Ser Ser Tyr Ala Met Ser Trp Val Arg Gln
65                  70                  75                  80

Ala Pro Gly Lys Gly Leu Glu Trp Val Ser Ile Ala Gly Gly Gly
            85                  90                  95

Ser Pro Thr Ile Tyr Ala Asp Ser Val Lys Gly Arg Phe Thr Ile Ser
                100                 105                 110

Arg Asp Asn Ser Lys Asn Thr Leu Tyr Leu Gln Met Asn Ser Leu Arg
            115                 120                 125

Ala Glu Asp Thr Ala Val Tyr Tyr Cys Ala Lys Arg Trp Thr Ala Phe
        130                 135                 140

Asp Tyr Trp Gly Gln Gly Thr Leu Val Thr Val Ser Ser Gly Gly Gly
145                 150                 155                 160

Gly Ser Gly Gly Gly Gly Ser Gly Gly Gly Gly Ser Thr Asp Ile Gln
                165                 170                 175

Met Thr Gln Ser Pro Ser Ser Leu Ser Ala Ser Val Gly Asp Arg Val
            180                 185                 190

Thr Ile Thr Cys Arg Ala Ser Gln Ser Ile Ser Ser Tyr Leu Asn Trp
        195                 200                 205

Tyr Gln Gln Lys Pro Gly Lys Ala Pro Lys Leu Leu Ile Tyr Arg Ala
    210                 215                 220

Ser Asn Leu Gln Ser Gly Val Pro Ser Arg Phe Ser Gly Ser Gly Ser
225                 230                 235                 240

Gly Thr Asp Phe Thr Leu Thr Ile Ser Ser Leu Gln Pro Glu Asp Phe
                245                 250                 255

Ala Thr Tyr Tyr Cys Gln Gln Ser His Pro Ser Pro Ile Thr Phe Gly
            260                 265                 270

Gln Gly Thr Lys Val Glu Ile Lys Arg Ala Ala Ala His His His His
```

```
                275                 280                 285
His His Gly Ala Ala Glu Gln Lys Leu Xaa Ser Glu Glu Asp
            290                 295                 300

<210> SEQ ID NO 19
<211> LENGTH: 980
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (8)..(11)
<223> OTHER INFORMATION: a, c, t, g, unknown or other
<220> FEATURE:
<221> NAME/KEY: modified_base
<222> LOCATION: (850)..(850)
<223> OTHER INFORMATION: a, c, t, g, unknown or other
<220> FEATURE:
<221> NAME/KEY: modified_base
<222> LOCATION: (912)..(912)
<223> OTHER INFORMATION: a, c, t, g, unknown or other
<220> FEATURE:
<221> NAME/KEY: modified_base
<222> LOCATION: (937)..(937)
<223> OTHER INFORMATION: a, c, t, g, unknown or other
<220> FEATURE:
<221> NAME/KEY: modified_base
<222> LOCATION: (957)..(958)
<223> OTHER INFORMATION: a, c, t, g, unknown or other
<220> FEATURE:
<221> NAME/KEY: modified_base
<222> LOCATION: (965)..(965)
<223> OTHER INFORMATION: a, c, t, g, unknown or other
<220> FEATURE:
<221> NAME/KEY: modified_base
<222> LOCATION: (976)..(976)
<223> OTHER INFORMATION: a, c, t, g, unknown or other

<400> SEQUENCE: 19
ctatgcgnnn nattcagatc ctcttctgag atgagttttt gttctgcggc cccgtgatgg      60
tgatgatgat gtgcggccgc ccgtttgatt ccaccttgg tcccttggcc gaacgtagga     120
ggcgaagtct gaacctgttg acagtagtaa gttgcaaaat cttcaggttg cagactgctg     180
atggtgagag tgaaatctgt cccagatcca ctgccactga accttgatgg gaccccactt     240
tgcaacaggg atgcacgata gatcaggagc ttagggctt tccctggttt ctgctgatac      300
caatttaaat agctgctaat gctctggctt gcccggcaag tgatggtgac tctgtctcct     360
acagatgcag acagggagga tggagactgg gtcatctgga tgtccgtcga cccgccaccg     420
ccgctgccac ctccgcctga accgcctcca ccgctcgaga cggtgaccag ggttccctgg     480
ccccagtagt caaactgctt accacgtttc gcacagtaat atacggccgt gtcctcggct     540
ctcaggctgt tcatttgcag atacagcgtg ttcttggaat tgtctctgga gatggtgaac     600
cggcccttca cggagtctgc gtaatgtgtc acagtaccat ccggccaaat acctgagacc     660
cactccagcc ccttccctgg agcctggcgg acccagctca tggcatagct gctaaaggtg     720
aatccagagg ctgcacagga gagtctcagg acccccag gctgtaccaa gcctccccca      780
gactccaaca gctgcacctc ggccatggcc ggctgggccg cgagtaataa caatccagcg     840
gctgccgtan gcaataggta tttcattatg actgtctcct tgaaatagaa tttgcatgca     900
agcttggcgt antcatggtc atagctgttt cctgtgngaa attgttatcc gctcacnntt     960
ccacncaaca tacganccgg                                                 980
```

```
<210> SEQ ID NO 20
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (286)..(287)
<223> OTHER INFORMATION: Any amino acid

<400> SEQUENCE: 20
```

Met Lys Tyr Leu Leu Xaa Thr Ala Ala Ala Gly Leu Leu Leu Ala
1               5                   10                  15

Ala Gln Pro Ala Met Ala Glu Val Gln Leu Leu Glu Ser Gly Gly
            20                  25                  30

Leu Val Gln Pro Gly Gly Ser Leu Arg Leu Ser Cys Ala Ala Ser
        35                  40                  45

Gly Phe Thr Phe Ser Ser Tyr Ala Met Ser Trp Val Arg Gln Ala Pro Gly
    50                  55                  60

Lys Gly Leu Glu Trp Val Ser Gly Ile Trp Pro Asp Gly Thr Val Thr
65                  70                  75                  80

His Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Arg Gly Lys Gln Phe Asp Tyr Trp
        115                 120                 125

Gly Gln Gly Thr Leu Val Thr Val Ser Ser Gly Gly Gly Gly Ser Gly
130                 135                 140

Gly Gly Gly Ser Gly Gly Gly Gly Ser Thr Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Arg Ala Ser Leu Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Val Gln Thr Ser Pro Pro Thr Phe Gly Gln Gly Thr
                245                 250                 255

Lys Val Glu Ile Lys Arg Ala Ala Ala His His His His His His Gly
            260                 265                 270

Ala Ala Glu Gln Lys Leu Ile Ser Glu Glu Asp Leu Asn Xaa Xaa His
        275                 280                 285

Arg

```
<210> SEQ ID NO 21
<211> LENGTH: 973
<212> TYPE: DNA
<213> ORGANISM: Artificial Sequence
```

```
<220> FEATURE:
<223> OTHER INFORMATION: Description of Artificial Sequence: Synthetic
      polynucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (8)..(13)
<223> OTHER INFORMATION: a, c, t, g, unknown or other
<220> FEATURE:
<221> NAME/KEY: modified_base
<222> LOCATION: (849)..(851)
<223> OTHER INFORMATION: a, c, t, g, unknown or other
<220> FEATURE:
<221> NAME/KEY: modified_base
<222> LOCATION: (856)..(856)
<223> OTHER INFORMATION: a, c, t, g, unknown or other
<220> FEATURE:
<221> NAME/KEY: modified_base
<222> LOCATION: (904)..(904)
<223> OTHER INFORMATION: a, c, t, g, unknown or other
<220> FEATURE:
<221> NAME/KEY: modified_base
<222> LOCATION: (907)..(908)
<223> OTHER INFORMATION: a, c, t, g, unknown or other

<400> SEQUENCE: 21
ctangcgnnn nnntcagatc ctcttctgag atgagttttt gttctgcggc cccgtgatgg      60
tgatgatgat gtgcggccgc ccgtttgatt tccaccttgg tccttggcc gaacgtagaa      120
ggattatcat cattctgttg acagtagtaa gttgcaaaat cttcaggttg cagactgctg     180
atggtgagag tgaaatctgt cccagatcca ctgccactga accttgatgg daccccactt    240
tgcaaagtgg atgcatcata aatcaggagc ttaggggctt tccctggttt ctgctgatac     300
caatttaaat agctgctaat gctctgactt gcccggcaag tgatggtgac tctgtctcct    360
acagatgcag acagggagga tggagactgg gtcatctgga tgtccgtcga cccgccaccg    420
ccgctgccac ctccgcctga accgcctcca ccgctcgaga cggtgaccag ggttccctgg    480
ccccagtagt caaaaccatt agaagttttc gcacagtaat atacggccgt gtcctcggct    540
ctcaggctgt tcatttgcag atacagcgtg ttcttggaat tgtctctgga gatggtgaac    600
cggcccttca cggagtctgc gtaatatgta gtactaccag tagcatcaat agttgagacc    660
cactccagcc ccttccctgg agcctggcgg acccagctca tggcatagct gctaaaggtg    720
aatccagagg ctgcacagga gagtctcagg accccccag gctgtaccaa gcctccccca    780
gactccaaca gctgcacctc ggccatggcc ggctgggccg cgagtaataa caatccagcg    840
gctgccgtnn naatangtat ttcattatga ctgtctcctt gaaatagaat ttgcatgcaa    900
gctnggnnta atcatggtca tagctgtttc ctgtgtgaaa ttgttatccg ctcacaattc    960
cacacaacat acg                                                       973

<210> SEQ ID NO 22
<211> LENGTH: 294
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(16)
```

<223> OTHER INFORMATION: Any amino acid

<400> SEQUENCE: 22

```
Met Gln Ile Leu Phe Gln Gly Asp Ser His Asn Glu Ile Xaa Ile Xaa
1               5                   10                  15

Thr Ala Ala Ala Gly Leu Leu Leu Ala Ala Gln Pro Ala Met Ala
            20                  25                  30

Glu Val Gln Leu Leu Glu Ser Gly Gly Leu Val Gln Pro Gly Gly
        35                  40                  45

Ser Leu Arg Leu Ser Cys Ala Ala Ser Gly Phe Thr Phe Ser Ser Tyr
    50                  55                  60

Ala Met Ser Trp Val Arg Gln Ala Pro Gly Lys Gly Leu Glu Trp Val
65                  70                  75                  80

Ser Thr Ile Asp Ala Thr Gly Ser Thr Thr Tyr Tyr Ala Asp Ser Val
                85                  90                  95

Lys Gly Arg Phe Thr Ile Ser Arg Asp Asn Ser Lys Asn Thr Leu Tyr
                100                 105                 110

Leu Gln Met Asn Ser Leu Arg Ala Glu Asp Thr Ala Val Tyr Tyr Cys
            115                 120                 125

Ala Lys Thr Ser Asn Gly Phe Asp Tyr Trp Gly Gln Gly Thr Leu Val
    130                 135                 140

Thr Val Ser Ser Gly Gly Gly Gly Ser Gly Gly Gly Gly Ser Gly Gly
145                 150                 155                 160

Gly Gly Ser Thr Asp Ile Gln Met Thr Gln Ser Pro Ser Ser Leu Ser
                165                 170                 175

Ala Ser Val Gly Asp Arg Val Thr Ile Thr Cys Arg Ala Ser Gln Ser
            180                 185                 190

Ile Ser Ser Tyr Leu Asn Trp Tyr Gln Gln Lys Pro Gly Lys Ala Pro
    195                 200                 205

Lys Leu Leu Ile Tyr Asp Ala Ser Thr Leu Gln Ser Gly Val Pro Ser
210                 215                 220

Arg Phe Ser Gly Ser Gly Ser Gly Thr Asp Phe Thr Leu Thr Ile Ser
225                 230                 235                 240

Ser Leu Gln Pro Glu Asp Phe Ala Thr Tyr Tyr Cys Gln Gln Asn Asp
                245                 250                 255

Asp Asn Pro Ser Thr Phe Gly Gln Gly Thr Lys Val Glu Ile Lys Arg
            260                 265                 270

Ala Ala Ala His His His His His His Gly Ala Ala Glu Gln Lys Leu
    275                 280                 285

Ile Ser Glu Glu Asp Leu
    290
```

<210> SEQ ID NO 23
<211> LENGTH: 959
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
<222> LOCATION: (55)..(55)
<223> OTHER INFORMATION: a, c, t, g, unknown or other
<220> FEATURE:
<221> NAME/KEY: modified_base

```
<222> LOCATION: (837)..(838)
<223> OTHER INFORMATION: a, c, t, g, unknown or other
<220> FEATURE:
<221> NAME/KEY: modified_base
<222> LOCATION: (875)..(875)
<223> OTHER INFORMATION: a, c, t, g, unknown or other
<220> FEATURE:
<221> NAME/KEY: modified_base
<222> LOCATION: (895)..(895)
<223> OTHER INFORMATION: a, c, t, g, unknown or other
<220> FEATURE:
<221> NAME/KEY: modified_base
<222> LOCATION: (906)..(906)
<223> OTHER INFORMATION: a, c, t, g, unknown or other
<220> FEATURE:
<221> NAME/KEY: modified_base
<222> LOCATION: (922)..(922)
<223> OTHER INFORMATION: a, c, t, g, unknown or other
<220> FEATURE:
<221> NAME/KEY: modified_base
<222> LOCATION: (944)..(944)
<223> OTHER INFORMATION: a, c, t, g, unknown or other
<220> FEATURE:
<221> NAME/KEY: modified_base
<222> LOCATION: (950)..(950)
<223> OTHER INFORMATION: a, c, t, g, unknown or other
<220> FEATURE:
<221> NAME/KEY: modified_base
<222> LOCATION: (954)..(954)
<223> OTHER INFORMATION: a, c, t, g, unknown or other

<400> SEQUENCE: 23
ttcagatcct cttctgagan gagtttttgt tctgcggccc cgtgatggtg atgangatgt      60
gcggccgccc gtttgatttc caccttggtc ccttggccga acgtagtagg actagcataa    120
ctctgttgac agtagtaagt tgcaaaatct tcaggttgca gaccgctgat ggtgagagtg    180
aaatctgtcc cagatccact gccactgaac cttgatggga ccccactttg caaagaggat    240
gcaccataga tcaggagctt aggggctttc cctggtttct gctgatacca atttaaatag    300
ctgctaatgc tctgacttgc ccggcaagtg atggtgactc tgtctcctac agatgcagac    360
agggaggatg gagactgggt catctggatg tccgtcgacc cgccaccgcc gctgccacct    420
ccgcctgaac cgcctccacc gctcgagacg gtgaccaggg ttccctggcc ccagtagtca    480
aaagcagtag cagttttcgc acagtaatat acggccgtgt cctcggctct caggctgttc    540
atttgcagat acagcgtgtt cttggaattg tctctggaga tggtgaaccg gcccttcacg    600
gagtctgcgt aacttgtagc atcaccatta gaataaatag atgagaccca ctccagcccc    660
ttccctggag cctggcggac ccagctcatg gcatagctgc taaaggtgaa tccagaggct    720
gcacaggaga gtctcaggga cccccaggc tgtaccaagc ctcccccaga ctccaacagc      780
tgcacctcgg ccatggccgg ctgggccgcg agtaataaca atccagcggc tgccgtnnca    840
ataggtattt cattatgact gtctccttga aatanaattt gcatgcaagc ttggngtaat    900
catggncata gctgtttcct gngtgaaatt gttatccgct cacnattccn cacnacata    959

<210> SEQ ID NO 24
<211> LENGTH: 295
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
```

<222> LOCATION: (16)..(16)
<223> OTHER INFORMATION: Any amino acid
<220> FEATURE:
<221> NAME/KEY: MOD_RES
<222> LOCATION: (277)..(277)
<223> OTHER INFORMATION: Any amino acid
<220> FEATURE:
<221> NAME/KEY: MOD_RES
<222> LOCATION: (289)..(289)
<223> OTHER INFORMATION: Any amino acid

<400> SEQUENCE: 24

```
Met Gln Ile Xaa Phe Gln Gly Asp Ser His Asn Glu Ile Pro Ile Xaa
1               5                   10                  15

Thr Ala Ala Gly Leu Leu Leu Ala Ala Gln Pro Ala Met Ala
            20                  25                  30

Glu Val Gln Leu Leu Glu Ser Gly Gly Gly Leu Val Gln Pro Gly Gly
        35                  40                  45

Ser Leu Arg Leu Ser Cys Ala Ala Ser Gly Phe Thr Phe Ser Ser Tyr
    50                  55                  60

Ala Met Ser Trp Val Arg Gln Ala Pro Gly Lys Gly Leu Glu Trp Val
65                  70                  75                  80

Ser Ser Ile Tyr Ser Asn Gly Asp Ala Thr Ser Tyr Ala Asp Ser Val
                85                  90                  95

Lys Gly Arg Phe Thr Ile Ser Arg Asp Asn Ser Lys Asn Thr Leu Tyr
            100                 105                 110

Leu Gln Met Asn Ser Leu Arg Ala Glu Asp Thr Ala Val Tyr Tyr Cys
        115                 120                 125

Ala Lys Thr Ala Thr Ala Phe Asp Tyr Trp Gly Gln Gly Thr Leu Val
    130                 135                 140

Thr Val Ser Ser Gly Gly Gly Ser Gly Gly Gly Gly Ser Gly Gly
145                 150                 155                 160

Gly Gly Ser Thr Asp Ile Gln Met Thr Gln Ser Pro Ser Ser Leu Ser
                165                 170                 175

Ala Ser Val Gly Asp Arg Val Thr Ile Thr Cys Arg Ala Ser Gln Ser
            180                 185                 190

Ile Ser Ser Tyr Leu Asn Trp Tyr Gln Gln Lys Pro Gly Lys Ala Pro
        195                 200                 205

Lys Leu Leu Ile Tyr Gly Ala Ser Ser Leu Gln Ser Gly Val Pro Ser
    210                 215                 220

Arg Phe Ser Gly Ser Gly Ser Gly Thr Asp Phe Thr Leu Thr Ile Ser
225                 230                 235                 240

Gly Leu Gln Pro Glu Asp Phe Ala Thr Tyr Tyr Cys Gln Gln Ser Tyr
                245                 250                 255

Ala Ser Pro Thr Thr Phe Gly Gln Gly Thr Lys Val Glu Ile Lys Arg
            260                 265                 270

Ala Ala Ala His Xaa His His His His Gly Ala Ala Glu Gln Lys Leu
        275                 280                 285

Xaa Ser Glu Glu Asp Leu Lys
    290                 295
```

<210> SEQ ID NO 25
<211> LENGTH: 971
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: modified_base
<222> LOCATION: (851)..(851)
<223> OTHER INFORMATION: a, c, t, g, unknown or other
<220> FEATURE:
<221> NAME/KEY: modified_base
<222> LOCATION: (914)..(914)
<223> OTHER INFORMATION: a, c, t, g, unknown or other
<220> FEATURE:
<221> NAME/KEY: modified_base
<222> LOCATION: (938)..(938)
<223> OTHER INFORMATION: a, c, t, g, unknown or other
<220> FEATURE:
<221> NAME/KEY: modified_base
<222> LOCATION: (952)..(952)
<223> OTHER INFORMATION: a, c, t, g, unknown or other
<220> FEATURE:
<221> NAME/KEY: modified_base
<222> LOCATION: (965)..(966)
<223> OTHER INFORMATION: a, c, t, g, unknown or other

<400> SEQUENCE: 25

```
ctatgcgncc ccattcagat cctcttctga gangagttttt tgttctgcgg ccccgtgatg      60
gtgatgatga tgtgcggccg cccgtttgat ttccaccttg gtcccttggc cgaacgtagg     120
aggcgaagtc tgaacctgtt gacagtagta agttgcaaaa tcttcaggtt gcagactgct     180
gatggtgaga gtgaaatctg tcccagatcc actgccactg aaccttgatg gaccccact      240
ttgcaacagg gatgcacgat agatcaggag cttagggcct ttccctggtt tctgctgata     300
ccaatttaaa tagctgctaa tgctctggct tgcccggcaa gtgatggtga ctctgtctcc     360
tacagatgca gacagggagg atggagactg ggtcatctgg atgtccgtcg acccgccacc     420
gccgctgcca cctccgcctg aaccgcctcc accgctcgag acggtgacca gggttccctg     480
gccccagtag tcaaactgct taccacgttt cgcacagtaa tatacggccg tgtcctcggc     540
tctcaggctt tcatttgca gatacagcgt gttcttggaa ttgtctctgg agatggtgaa      600
ccggcccttc acggagtctg cgtaatgtgt cacagtacca tccggccaaa tacctgagac     660
ccactccagc cccttccctg gagcctggcg gacccagctc atggcatagc tgctaaaggt     720
gaatccagag gctgcacagg agagtctcag ggaccccca ggctgtacca agcctccccc      780
agactccaac agctgcacct cggccatggc cggctgggcc gcgagtaata acaatccagc     840
ggctgccgta ngcaataggt atttcattat gactgtctcc ttgaaataga atttgcatgc     900
aagcttggcg taancatggt catagctgtt tcctgtgnga aattgttatc cngctcacaa     960
ttccnncaca a                                                         971
```

<210> SEQ ID NO 26
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (279)..(279)

<223> OTHER INFORMATION: Any amino acid
<220> FEATURE:
<221> NAME/KEY: MOD_RES
<222> LOCATION: (287)..(287)
<223> OTHER INFORMATION: Any amino acid

<400> SEQUENCE: 26

Met Lys Tyr Leu Leu Xaa Thr Ala Ala Ala Gly Leu Leu Leu Leu Ala
1               5                   10                  15

Ala Gln Pro Ala Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Gly Ile Trp Pro Asp Gly Thr Val Thr
65                  70                  75                  80

His Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Arg Gly Lys Gln Phe Asp Tyr Trp
        115                 120                 125

Gly Gln Gly Thr Leu Val Thr Val Ser Gly Gly Gly Gly Ser Gly
    130                 135                 140

Gly Gly Ser Gly Gly Gly Gly Ser Thr Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Arg Ala Ser Leu Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Val Gln Thr Ser Pro Pro Thr Phe Gly Gln Gly Thr
                245                 250                 255

Lys Val Glu Ile Lys Arg Ala Ala Ala His His His His His His Gly
            260                 265                 270

Ala Ala Glu Gln Lys Leu Xaa Ser Glu Glu Asp Leu Asn Gly Xaa Ala
        275                 280                 285

<210> SEQ ID NO 27
<211> LENGTH: 965
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (7)..(9)
<223> OTHER INFORMATION: a, c, t, g, unknown or other
<220> FEATURE:
<221> NAME/KEY: modified_base
<222> LOCATION: (14)..(14)
<223> OTHER INFORMATION: a, c, t, g, unknown or other
<220> FEATURE:

```
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (67)..(69)
<223> OTHER INFORMATION: a, c, t, g, unknown or other
<220> FEATURE:
<221> NAME/KEY: modified_base
<222> LOCATION: (747)..(747)
<223> OTHER INFORMATION: a, c, t, g, unknown or other
<220> FEATURE:
<221> NAME/KEY: modified_base
<222> LOCATION: (848)..(848)
<223> OTHER INFORMATION: a, c, t, g, unknown or other
<220> FEATURE:
<221> NAME/KEY: modified_base
<222> LOCATION: (855)..(855)
<223> OTHER INFORMATION: a, c, t, g, unknown or other
<220> FEATURE:
<221> NAME/KEY: modified_base
<222> LOCATION: (889)..(889)
<223> OTHER INFORMATION: a, c, t, g, unknown or other
<220> FEATURE:
<221> NAME/KEY: modified_base
<222> LOCATION: (907)..(908)
<223> OTHER INFORMATION: a, c, t, g, unknown or other
<220> FEATURE:
<221> NAME/KEY: modified_base
<222> LOCATION: (918)..(919)
<223> OTHER INFORMATION: a, c, t, g, unknown or other
<220> FEATURE:
<221> NAME/KEY: modified_base
<222> LOCATION: (960)..(960)
<223> OTHER INFORMATION: a, c, t, g, unknown or other
<220> FEATURE:
<221> NAME/KEY: modified_base
<222> LOCATION: (962)..(962)
<223> OTHER INFORMATION: a, c, t, g, unknown or other

<400> SEQUENCE: 27
tatgcgnnna ttcngatcct cttctgagan gagtttttgt tctgcggccc cgtgatggtg    60
atgatgnnnt gcggccgccc gtttgatttc caccttggtc ccttggccga acgtattagg   120
acaatcagta gtctgttgac agtagtaagt tgcaaaatct tcaggttgca gactgctgat   180
ggtgagagtg aaatctgtcc cagatccact gccactgaac cttgatggga ccccactttg   240
caaagtggat gcattataga tcaggagctt aggggctttc cctggtttct gctgatacca   300
atttaaatag ctgctaatgc tctgacttgc ccggcaagtg atggtgactc tgtctcctac   360
agatgcagac agggaggatg gagactgggt catctggatg tccgtcgacc cgccaccgcc   420
gctgccacct ccgcctgaac cgcctccacc gctcgagacg gtgaccaggg ttccctggcc   480
ccagtagtca aaattagcac cagatttcgc acagtaatat acggccgtgt cctcggctct   540
caggctgttc atttgcagat acagcgtgtt cttggaattg tctctggaga tggtgaacct   600
gcccttcacg gagtctgcgt aagatgtagc ataaccacta gcagtaatac ctgagaccca   660
ctccagcccc ttccctggag cctggcggac ccagctcatg gcatagctgc taaaggtgaa   720
tccagaggct gcacaggaga gtctcangga cccccaggc tgtaccaagc ctcccccaga   780
ctccaacagc tgcacctcgg ccatggccgg ctgggccgcg agtaataaca atccagcggc   840
tgccgtangc aatangtatt tcattatgac tgtctccttg aaatagaant ttgcatgcaa   900
gcttggnnta atcatggnna tagctgtttc ctgtgtgaaa ttgttatccg ctcacaattn   960
cncac                                                              965

<210> SEQ ID NO 28
<211> LENGTH: 305
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (23)..(23)
<223> OTHER INFORMATION: Any amino acid
<220> FEATURE:
<221> NAME/KEY: MOD_RES
<222> LOCATION: (57)..(57)
<223> OTHER INFORMATION: Any amino acid
<220> FEATURE:
<221> NAME/KEY: MOD_RES
<222> LOCATION: (283)..(283)
<223> OTHER INFORMATION: Any amino acid
<220> FEATURE:
<221> NAME/KEY: MOD_RES
<222> LOCATION: (296)..(296)
<223> OTHER INFORMATION: Any amino acid
<220> FEATURE:
<221> NAME/KEY: MOD_RES
<222> LOCATION: (301)..(301)
<223> OTHER INFORMATION: Any amino acid
<220> FEATURE:
<221> NAME/KEY: MOD_RES
<222> LOCATION: (303)..(303)
<223> OTHER INFORMATION: Any amino acid

<400> SEQUENCE: 28

Met Ile Xaa Pro Ser Leu His Ala Xaa Phe Tyr Phe Lys Glu Thr Val
1               5                   10                  15

Ile Met Lys Tyr Xaa Leu Xaa Thr Ala Ala Gly Leu Leu Leu Leu
            20                  25                  30

Ala Ala Gln Pro Ala Met Ala Glu Val Gln Leu Leu Glu Ser Gly Gly
            35                  40                  45

Gly Leu Val Gln Pro Gly Gly Ser Xaa Arg Leu Ser Cys Ala Ala Ser
        50                  55                  60

Gly Phe Thr Phe Ser Ser Tyr Ala Met Ser Trp Val Arg Gln Ala Pro
65                  70                  75                  80

Gly Lys Gly Leu Glu Trp Val Ser Gly Ile Thr Ala Ser Gly Tyr Ala
                85                  90                  95

Thr Ser Tyr Ala Asp Ser Val Lys Gly Arg Phe Thr Ile Ser Arg Asp
            100                 105                 110

Asn Ser Lys Asn Thr Leu Tyr Leu Gln Met Asn Ser Leu Arg Ala Glu
        115                 120                 125

Asp Thr Ala Val Tyr Tyr Cys Ala Lys Ser Gly Ala Asn Phe Asp Tyr
    130                 135                 140

Trp Gly Gln Gly Thr Leu Val Thr Val Ser Ser Gly Gly Gly Gly Ser
145                 150                 155                 160

Gly Gly Gly Gly Ser Gly Gly Gly Ser Thr Asp Ile Gln Met Thr
                165                 170                 175

Gln Ser Pro Ser Ser Leu Ser Ala Ser Val Gly Asp Arg Val Thr Ile
            180                 185                 190
```

```
Thr Cys Arg Ala Ser Gln Ser Ile Ser Ser Tyr Leu Asn Trp Tyr Gln
        195                 200                 205

Gln Lys Pro Gly Lys Ala Pro Lys Leu Leu Ile Tyr Asn Ala Ser Thr
    210                 215                 220

Leu Gln Ser Gly Val Pro Ser Arg Phe Ser Gly Ser Gly Ser Gly Thr
225                 230                 235                 240

Asp Phe Thr Leu Thr Ile Ser Ser Leu Gln Pro Glu Asp Phe Ala Thr
                245                 250                 255

Tyr Tyr Cys Gln Gln Thr Thr Asp Cys Pro Asn Thr Phe Gly Gln Gly
            260                 265                 270

Thr Lys Val Glu Ile Lys Arg Ala Ala Ala Xaa His His His His His
        275                 280                 285

Gly Ala Ala Glu Gln Lys Leu Xaa Ser Glu Glu Asp Xaa Asn Xaa Arg
        290                 295                 300

Ile
305

<210> SEQ ID NO 29
<211> LENGTH: 963
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (6)..(8)
<223> OTHER INFORMATION: a, c, t, g, unknown or other
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (28)..(28)
<223> OTHER INFORMATION: a, c, t, g, unknown or other
<220> FEATURE:
<221> NAME/KEY: modified_base
<222> LOCATION: (53)..(54)
<223> OTHER INFORMATION: a, c, t, g, unknown or other
<220> FEATURE:
<221> NAME/KEY: modified_base
<222> LOCATION: (62)..(66)
<223> OTHER INFORMATION: a, c, t, g, unknown or other
<220> FEATURE:
<221> NAME/KEY: modified_base
<222> LOCATION: (610)..(610)
<223> OTHER INFORMATION: a, c, t, g, unknown or other
<220> FEATURE:
<221> NAME/KEY: modified_base
<222> LOCATION: (839)..(839)
<223> OTHER INFORMATION: a, c, t, g, unknown or other
<220> FEATURE:
<221> NAME/KEY: modified_base
<222> LOCATION: (841)..(841)
<223> OTHER INFORMATION: a, c, t, g, unknown or other
<220> FEATURE:
<221> NAME/KEY: modified_base
<222> LOCATION: (846)..(847)
<223> OTHER INFORMATION: a, c, t, g, unknown or other
<220> FEATURE:
<221> NAME/KEY: modified_base
<222> LOCATION: (884)..(885)
<223> OTHER INFORMATION: a, c, t, g, unknown or other
<220> FEATURE:
<221> NAME/KEY: modified_base
```

```
<222> LOCATION: (904)..(904)
<223> OTHER INFORMATION: a, c, t, g, unknown or other
<220> FEATURE:
<221> NAME/KEY: modified_base
<222> LOCATION: (908)..(908)
<223> OTHER INFORMATION: a, c, t, g, unknown or other
<220> FEATURE:
<221> NAME/KEY: modified_base
<222> LOCATION: (915)..(915)
<223> OTHER INFORMATION: a, c, t, g, unknown or other
<220> FEATURE:
<221> NAME/KEY: modified_base
<222> LOCATION: (927)..(927)
<223> OTHER INFORMATION: a, c, t, g, unknown or other
<220> FEATURE:
<221> NAME/KEY: modified_base
<222> LOCATION: (931)..(931)
<223> OTHER INFORMATION: a, c, t, g, unknown or other
<220> FEATURE:
<221> NAME/KEY: modified_base
<222> LOCATION: (935)..(935)
<223> OTHER INFORMATION: a, c, t, g, unknown or other
<220> FEATURE:
<221> NAME/KEY: modified_base
<222> LOCATION: (952)..(954)
<223> OTHER INFORMATION: a, c, t, g, unknown or other

<400> SEQUENCE: 29
gcggcnnntt cngancctct tctgaganga gtttttgttc tgcggccccg tgnnggtgat      60
gnnnnngtgc ggccgcccgt ttgatttcca ccttggtccc ttggccgaac gtattagggg    120
tactgtaact ctgttgacag tagtaagttg caaaatcttc aggttgcaga ctgctgatgg    180
tgagagtgaa atctgtccca gatccactgc cactgaacct tgatgggacc ccactttgca    240
aactggatgc agcatagatc aggagcttag gggctttccc tggtttctgc tgataccaat    300
ttaaatagct gctaatgctc tgacttgccc ggcaagtgat ggtgactctg tctcctacag    360
atgcagacag ggaggatgga gactgggtca tctggatgtc cgtcgacccg ccaccgccgc    420
tgccacctcc gcctgaaccg cctccaccgc tcgagacggt gaccagggtt ccctggcccc    480
agtagtcaaa cgccggatga tatttcgcac agtaatatac ggccgtgtcc tcggctctca    540
ggctgttcat ttgcagatac agcgtgttct tggaattgtc tctggagatg gtgaaccggc    600
ccttcacggn gtctgcgtac tctgtcggca gaccctgcgg cgcaatcgat gagacccact    660 ccagccccctt ccctggagcc tggcggaccc agctcatggc atagctgcta aaggtgaatc    720
cagaggctgc acaggagagt ctcagggacc ccccaggctg taccaagcct ccccccagact    780 ccaacagctg cacctcggcc atggccggct gggccgcgag taataacaat ccagcggcng    840
ncgtanncaa taggtatttc attatgactg tctccttgaa atannatttg catgcaagct    900
tggngtantc atggncatag ctgtttnctg ngtgnaaatt gttatccgct cnnnaatttc    960
cac                                                                   963

<210> SEQ ID NO 30
<211> LENGTH: 283
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
```

```
<220> FEATURE:
<221> NAME/KEY: MOD_RES
<222> LOCATION: (85)..(85)
<223> OTHER INFORMATION: Any amino acid
<220> FEATURE:
<221> NAME/KEY: MOD_RES
<222> LOCATION: (266)..(267)
<223> OTHER INFORMATION: Any amino acid
<220> FEATURE:
<221> NAME/KEY: MOD_RES
<222> LOCATION: (270)..(270)
<223> OTHER INFORMATION: Any amino acid
<220> FEATURE:
<221> NAME/KEY: MOD_RES
<222> LOCATION: (279)..(279)
<223> OTHER INFORMATION: Any amino acid

<400> SEQUENCE: 30
```

Met Lys Tyr Leu Leu Xaa Thr Xaa Ala Ala Gly Leu Leu Leu Ala
1               5                   10                  15

Ala Gln Pro Ala Met Ala Glu Val Gln Leu Leu Glu Ser Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Ile Ala Pro Gln Gly Leu Pro Thr
65                  70                  75                  80

Glu Tyr Ala Asp Xaa Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Tyr His Pro Ala Phe Asp Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Thr Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ala Ala Ser Ser Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Ser Tyr Ser Thr Pro Asn Thr Phe Gly Gln Gly Thr
                245                 250                 255

Lys Val Glu Ile Lys Arg Ala Ala Ala Xaa Xaa His His Xaa His Gly
            260                 265                 270

Ala Ala Glu Gln Lys Leu Xaa Ser Glu Glu Asp
        275                 280

```
<210> SEQ ID NO 31
<211> LENGTH: 953
<212> TYPE: DNA
<213> ORGANISM: Artificial Sequence
<220> FEATURE:
```

```
<223> OTHER INFORMATION: Description of Artificial Sequence: Synthetic
      polynucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (7)..(8)
<223> OTHER INFORMATION: a, c, t, g, unknown or other
<220> FEATURE:
<221> NAME/KEY: modified_base
<222> LOCATION: (63)..(67)
<223> OTHER INFORMATION: a, c, t, g, unknown or other
<220> FEATURE:
<221> NAME/KEY: modified_base
<222> LOCATION: (688)..(688)
<223> OTHER INFORMATION: a, c, t, g, unknown or other
<220> FEATURE:
<221> NAME/KEY: modified_base
<222> LOCATION: (846)..(846)
<223> OTHER INFORMATION: a, c, t, g, unknown or other
<220> FEATURE:
<221> NAME/KEY: modified_base
<222> LOCATION: (853)..(853)
<223> OTHER INFORMATION: a, c, t, g, unknown or other
<220> FEATURE:
<221> NAME/KEY: modified_base
<222> LOCATION: (908)..(908)
<223> OTHER INFORMATION: a, c, t, g, unknown or other
<220> FEATURE:
<221> NAME/KEY: modified_base
<222> LOCATION: (915)..(915)
<223> OTHER INFORMATION: a, c, t, g, unknown or other
<220> FEATURE:
<221> NAME/KEY: modified_base
<222> LOCATION: (924)..(924)
<223> OTHER INFORMATION: a, c, t, g, unknown or other
<220> FEATURE:
<221> NAME/KEY: modified_base
<222> LOCATION: (941)..(941)
<223> OTHER INFORMATION: a, c, t, g, unknown or other
<220> FEATURE:
<221> NAME/KEY: modified_base
<222> LOCATION: (943)..(943)
<223> OTHER INFORMATION: a, c, t, g, unknown or other

<400> SEQUENCE: 31
gcgnccnntt cagatcctct tctgagatga gttttttgttc tgcggccccg tgatggtgat      60
gannnnntgc ggccgcccgt ttgatttcca ccttggtccc ttggccgaac gtagaaggag     120
aattaccagt ctgttgacag tagtaagttg caaaatcttc aggttgcaga ctgctgatgg     180
tgagagtgaa atctgtccca gatccactgc cactgaacct tgatgggacc ccactttgca     240
aagcggatgc agtatagatc aggagcttag gggctttccc tggtttctgc tgataccaat     300
ttaaatagct gctaatgctc tgacttgccc ggcaagtgat ggtgactctg tctcctacag     360
atgcagacag ggaggatgga gactgggtca tctggatgtc cgtcgacccg ccaccgccgc     420
tgccacctcc gcctgaaccg cctccaccgc tcgagacggt gaccagggtt ccctggcccc     480
agtagtcaaa agtactataa gatttcgcac agtaatatac ggccgtgtcc tcggctctca     540
ggctgttcat ttgcagatac agcgtgttct tggaattgtc tctggagatg gtgaaccggc     600
ccttcacgga gtctgcgtaa gctgtactag cactactagc agcaatacct gagacccact     660
ccagcccctt ccctggagcc tggcggancc agctcatggc atagctgcta aaggtgaatc     720
cagaggctgc acaggagagt ctcagggacc ccccaggctg taccaagcct cccccggact     780
ccaacagctg cacctcggcc atggccggct gggccgcgag taataacaat ccagcggctg     840
ccgtangcaa tangtatttc attatgactg tctccttgaa atagaatttg catgcaagct     900
```

```
tggcgtantc atggncatag ctgnttcctg tgtgaaattg ntnatccgct cac          953
```

<210> SEQ ID NO 32
<211> LENGTH: 284
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (59)..(59)
<223> OTHER INFORMATION: Any amino acid
<220> FEATURE:
<221> NAME/KEY: MOD_RES
<222> LOCATION: (266)..(267)
<223> OTHER INFORMATION: Any amino acid

<400> SEQUENCE: 32

Met Lys Tyr Xaa Leu Xaa Thr Ala Ala Ala Gly Leu Leu Leu Leu Ala
1               5                   10                  15

Ala Gln Pro Ala Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Xaa Arg Gln Ala Pro Gly
    50                  55                  60

Lys Gly Leu Glu Trp Val Ser Gly Ile Ala Ala Ser Ser Ala Ser Thr
65                  70                  75                  80

Ala Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Ser Tyr Ser Thr Phe Asp Tyr Trp
        115                 120                 125

Gly Gln Gly Thr Leu Val Thr Val Ser Ser Gly Gly Gly Gly Ser Gly
    130                 135                 140

Gly Gly Ser Gly Gly Gly Gly Ser Thr Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Thr Ala Ser Ala Leu
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Thr Gly Asn Ser Pro Ser Thr Phe Gly Gln Gly Thr
                245                 250                 255

Lys Val Glu Ile Lys Arg Ala Ala Ala Xaa Xaa His His His His Gly
            260                 265                 270

Ala Ala Glu Gln Lys Leu Ile Ser Glu Glu Asp Leu
            275                 280

<210> SEQ ID NO 33
<211> LENGTH: 696
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
atggccgagg tgcagctgtc ggagtctggg ggaggcttgg tacagcctgg ggggtccctg      60
agactctcct gtgcagcctc tggattcacc tttagcagct atgccatgag ctgggtccgc     120
caggctccag ggaaggggct ggagtgggtc tcaggtatta atagtaatgg tacttctaca     180
tcttacgcag actccgtgaa gggccggttc accatctcca gagacaattc caagaacacg     240
ctgtatctgc aaatgaacag cctgagagcc gaggacacgg ccgtatatta ctgtgcgaaa     300
tctgcttctg attttgacta ctggggccag ggaaccctgg tcaccgtctc gagcggtgga     360
ggcggttcag gcggaggtgg cagcggcggt ggcgggtcga cggacatcca gatgacccag     420
tctccatcct ccctgtctgc atctgtagga gacagagtca ccatcacttg ccgggcaagt     480
cagagcatta gcagctattt aaattggtat cagcagaaac cagggaaagc ccctaagctc     540
ctgatctata tgcatccac tttgcaaagt ggggtcccat caaggttcag tggcagtgga     600
tctgggacag atttcactct caccatcagc agtctgcaac ctgaagattt tgcaacttac     660
tactgtcaac agaatactta tagtcctact acgttc                              696

<210> SEQ ID NO 34
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Met Lys Tyr Leu Leu Pro Thr Asn Ala Ala Gly Leu Leu Leu Leu Ala
1               5                   10                  15

Ala Asn Pro Ala Met Ala Glu Val Gln Leu Ser Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Gly Ile Asn Ser Asn Gly Thr Ser Thr
65                  70                  75                  80

Ser Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Ser Ala Ser Asp Phe Asp Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Thr Asp Ile Gln Met Thr Gln
145                 150                 155                 160

Ser Pro Ser Ser Leu Ser Ala Ser Val Gly Asp Arg Val Thr Ile Thr
            165                 170                 175

Cys Arg Ala Ser Gln Ser Ile Ser Ser Tyr Leu Asn Trp Tyr Gln Gln
        180                 185                 190

Lys Pro Gly Lys Ala Pro Lys Leu Leu Ile Tyr Asn Ala Ser Thr Leu
    195                 200                 205

Gln Ser Gly Val Pro Ser Arg Phe Ser Gly Ser Gly Ser Gly Thr Asp
210                 215                 220

Phe Thr Leu Thr Ile Ser Ser Leu Gln Pro Glu Asp Phe Ala Thr Tyr
225                 230                 235                 240

Tyr Cys Gln Gln Asn Thr Tyr Ser Pro Thr Thr Phe Gly Asn Asn Asn
                245                 250                 255

Lys Val Glu Ile Lys Arg Ala Ala
            260

<210> SEQ ID NO 35
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (706)..(706)
<223> OTHER INFORMATION: a, c, t, g, unknown or other

<400> SEQUENCE: 35
atggccgaga tgcagctgtt ggagtctggg ggaggcttgg tacagcctgg ggggtccctg      60
agactctcct gtgcagcctc tggattcacc tttagcagct atgccatgag ctgggtccgc     120
caggctccag ggaaggggct ggagtgggtc tcatatatta ctgctaatgg tgatagtaca     180
acttacgcag actccgtgaa gggccggttc accatctcca gagacaattc caagaacacg     240
ctgtatctgc aaatgaacag cctgagagcc gaggacacgg ccgtatatta ctgtgcgaaa     300
agtactactg attttgacta ctggggccag ggaaccctgg tcaccgtctc gagcggtgga     360
ggcggttcag gcggaggtgg cagcggcggt ggcgggtcga cggacatcca gatgacccag     420
tctccatcct ccctgtctgc atctgtagga gacagagtca ccatcacttg ccgggcaagt     480
cagagcatta gcagctattt aaattggtat cagcagaaac cagggaaagc ccctaagctc     540
ctgatctata gtgcatccaa tttgcaaagt ggggtcccat caaggttcag tggcagtgga     600
tctgggacag atttcactct caccatcagc agtctgcaac tgaagatttt gcaacttac      660 tactgtcaac agacttctta tagtccttct acgttcggcc aagggnccaa ggtggaaatc     720
aaacgggcgg cc                                                         732

<210> SEQ ID NO 36
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (236)..(236)
<223> OTHER INFORMATION: Any amino acid

<400> SEQUENCE: 36

Met Ala Glu Met Gln Leu Leu Glu Ser Gly Gly Gly Leu Val Gln Pro

```
            1               5                   10                  15
Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
            35                  40                  45

Trp Val Ser Tyr Ile Thr Ala Asn Gly Asp Ser Thr Thr Tyr Ala Asp
            50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ser Thr Thr Asp Phe Asp Tyr Trp Gly Gln Gly Thr
            100                 105                 110

Leu Val Thr Val Ser Ser Gly Gly Gly Ser Gly Gly Gly Gly Ser
            115                 120                 125

Gly Gly Gly Gly Ser Thr Asp Ile Gln Met Thr Gln Ser Pro Ser Ser
130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Ser Ala Ser Asn Leu Gln Ser Gly Val
            180                 185                 190

Pro Ser Arg Phe Ser Gly Ser Gly Ser Gly Thr Asp Phe Thr Leu Thr
            195                 200                 205

Ile Ser Ser Leu Gln Pro Glu Asp Phe Ala Thr Tyr Tyr Cys Gln Gln
            210                 215                 220

Thr Ser Tyr Ser Pro Ser Thr Phe Gly Gln Gly Xaa Lys Val Glu Ile
225                 230                 235                 240

Lys Arg Ala Ala Ala
                245

<210> SEQ ID NO 37
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (54)..(54)
<223> OTHER INFORMATION: a, c, t, g, unknown or other

<400> SEQUENCE: 37
atggccgagg tgcagctgtt ggagtctggg ggaggcttgg tacagcctgg gggntccctg      60
agactctcct gtgcagcctc tggattcacc tttagcagct atgccatgag ctgggtccgc     120
caggctccag gaaggggct ggagtgggtc tcaactatta tgctagtgg tggtagtaca      180 ggttacgcag actccgtgaa gggccggttc accatctcca gagacaattc caagaacacg     240
ctgtatctgc aaatgaacag cctgagagcc gaggacacgg ccgtatatta ctgtgcgaaa     300
gctgatgctt attttgacta ctggggccag ggaaccctgg tcaccgtctc gagcggtgga     360
ggcggttcag gcggaggtgg cagcggcggt ggcgggtcga cggacatcca gatgacccag     420
tctccatcct ccctgtctgc atctgtagga gacagagtca ccatcacttg ccgggcaagt     480
cagagcatta gcagctattt aaattggtat cagcagaaac cagggaaagc ccctaagctc     540
```

```
ctgatctatt ctgcatcctc gttgcaaagt ggggtcccat caaggttcag tggcagtgga      600
tctgggacag atttcactct caccatcagc agtctgcaac ctgaagattt tgcaacttac      660
tactgtcaac aggatgctag tggtccttct acgttcggcc aagggaccaa ggtggaaatc      720
aaacgggcgg ccgca                                                       735
```

<210> SEQ ID NO 38
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Thr Ile Asn Ala Ser Gly Ser Thr Gly Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ala Asp Ala Tyr Phe Asp Tyr Trp Gly Gln Gly Thr
            100                 105                 110

Leu Val Thr Val Ser Ser Gly Gly Gly Ser Gly Gly Gly Ser
        115                 120                 125

Gly Gly Gly Gly Ser Thr Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Ser Ala Ser Ser Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Asp Ala Ser Gly Pro Ser Thr Phe Gly Gln Gly Thr Lys Val Glu Ile
225                 230                 235                 240

Lys Arg Ala Ala

<210> SEQ ID NO 39
<211> LENGTH: 736
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (706)..(706)
<223> OTHER INFORMATION: a, c, t, g, unknown or other -continued

```
<220> FEATURE:
<221> NAME/KEY: modified_base
<222> LOCATION: (731)..(731)
<223> OTHER INFORMATION: a, c, t, g, unknown or other

<400> SEQUENCE: 39
atggccgagg tgcagctgtt ggagtctggg ggaggcttgg tacagcctgg ggggtccctg      60
agactctcct gtgcagcctc tggattcacc tttagcagct atgccatgag ctgggtccgc     120
caggctccag ggaaggggct ggagtgggtc tcatatattg ctgatgatgg tgctaataca     180
gcttacgcag actccgtgaa gggccggttc accatctcca gagacaattc caagaacacg     240
ctgtatctgc aaatgaacag cctgagagcc gaggacacgg ccgtatatta ctgtgcgaaa     300
aataatgatg gttttgacta ctggggccag ggaaccctgg tcaccgtctc gagcggtgga     360
ggcggttcag gcggaggtgg cagcggcggt ggcgggtcga cgaacatcca gatgacccag     420
tctccatcct ccctgtctgc atctgtagga gacagagtca ccatcacttg ccgggcaagt     480
cagagcatta gcagctattt aaattggtat cagcagaaac cagggaaagc ccctaagctc     540
ctgatctatt ctgcatccac tttgcaaagt ggggtcccat caaggttcag tggcagtgga     600
tctgggacag atttcactct caccatcagc agtctgcaac tgaagatttt gcaacttac     660 tactgtcaac aggctgctac tagtccttct acgttcggcc aagggnccaa ggtggaaatc     720
aaacgggcgg ncgcac                                                     736

<210> SEQ ID NO 40
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (236)..(236)
<223> OTHER INFORMATION: Any amino acid
<220> FEATURE:
<221> NAME/KEY: MOD_RES
<222> LOCATION: (244)..(244)
<223> OTHER INFORMATION: Any amino acid

<400> SEQUENCE: 40

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Tyr Ile Ala Asp Asp Gly Ala Asn Thr Ala Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asn Asn Asp Gly Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Thr Asn Ile Gln Met Thr Gln Ser Pro Ser Ser
    130                 135                 140
```

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
            165                 170                 175

Ala Pro Lys Leu Leu Ile Tyr Ser Ala Ser Thr Leu Gln Ser Gly Val
        180                 185                 190

Pro Ser Arg Phe Ser Gly Ser Gly Ser Gly Thr Asp Phe Thr Leu Thr
    195                 200                 205

Ile Ser Ser Leu Gln Pro Glu Asp Phe Ala Thr Tyr Tyr Cys Gln Gln
210                 215                 220

Ala Ala Thr Ser Pro Ser Thr Phe Gly Gln Gly Xaa Lys Val Glu Ile
225                 230                 235                 240

Lys Arg Ala Xaa Ala
            245

<210> SEQ ID NO 41
<211> LENGTH: 886
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: modified_base
<222> LOCATION: (76)..(76)
<223> OTHER INFORMATION: a, c, t, g, unknown or other
<220> FEATURE:
<221> NAME/KEY: modified_base
<222> LOCATION: (78)..(78)
<223> OTHER INFORMATION: a, c, t, g, unknown or other
<220> FEATURE:
<221> NAME/KEY: modified_base
<222> LOCATION: (852)..(852)
<223> OTHER INFORMATION: a, c, t, g, unknown or other
<220> FEATURE:
<221> NAME/KEY: modified_base
<222> LOCATION: (875)..(876)
<223> OTHER INFORMATION: a, c, t, g, unknown or other
<220> FEATURE:
<221> NAME/KEY: modified_base
<222> LOCATION: (885)..(885)
<223> OTHER INFORMATION: a, c, t, g, unknown or other

<400> SEQUENCE: 41
ttcaaggaga cagtcataat gaaatancct attgcntacg gcanncgctg gattgttatt      60
actcgcggcc cagccngncc atggccgagg tgcagctgtt ggagtctggg ggaggcttgg     120
tacagcctgg ggggtccctg agactctcct gtgcagcctc tggattcacc tttagcagct     180
atgccatgag ctgggtccgc caggctccag ggaaggggct ggagtgggtc tcaaatatta     240
gttctgatgg tgattctaca gcttacgcag actccgtgaa gggccggttc accatctcca     300
gagacaattc caagaacacg ctgtatctgc aaatgaacag cctgagagcc gaggacacgg     360
ccgtatatta ctgtgcgaaa gcttctagta attttgacta ctggggccag ggaaccctgg     420
tcaccgtctc gagcggtgga ggcggttcag gcggaggtgg cagcggcggt ggcgggtcga     480

```
cggacatcca gatgacccag tctccatcct ccctgtctgc atctgtagga gacagagtca    540
ccatcacttg ccgggcaagt cagagcatta gcagctattt aaattggtat cagcagaaac    600
cagggaaagc ccctaagctc ctgatctatg ctgcatccaa tttgcaaagt ggggtcccat    660
caaggttcag tggcagtgga tctgggacag atttcactct caccatcagc agtctgcaac    720
ctgaagattt tgcaacttac tactgtcaac agtctaattc tgatcctact acgttcggcc    780
aagggaccaa ggtaatcaaa cgggcggccg cacatcatca tcaccatcac ggggccgcag    840
aacaaaaact cntctcagaa gaggatctga atggnnccgc atagnc                   886
```

<210> SEQ ID NO 42
<211> LENGTH: 267
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (258)..(258)
<223> OTHER INFORMATION: Any amino acid
<220> FEATURE:
<221> NAME/KEY: MOD_RES
<222> LOCATION: (265)..(266)
<223> OTHER INFORMATION: Any amino acid

<400> SEQUENCE: 42

```
Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Asn Ile Ser Ser Asp Gly Asp Ser Thr Ala Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ala Ser Ser Asn Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Thr Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Ala Ala Ser Asn Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Ser Asn Ser Asp Pro Thr Thr Phe Gly Gln Gly Thr Lys Val Ile Lys
225                 230                 235                 240
```

Arg Ala Ala Ala His His His His His His Gly Ala Ala Glu Gln Lys
                245                 250                 255

Leu Xaa Ser Glu Glu Asp Leu Asn Xaa Xaa Ala
        260                 265

<210> SEQ ID NO 43
<211> LENGTH: 909
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (907)..(907)
<223> OTHER INFORMATION: a, c, t, g, unknown or other

<400> SEQUENCE: 43 caggggggc ggngcctatg naaaaaacgc cagcaacgcg gccttttacg gttcctggcc      60
ctttgctggc cttttgctca catgttcttt cctgcgttat ccctgattc tgtggataac    120 cgtattaccg cctttgagtg agctgatacc gctcgccgca gccgaacgac cgagcgcagc    180
gagtcagtga gcgaggaagc ggaagagcgc ccaatacgca aaccgcctct ccccgcgcgt    240
tggccgattc attaatgcag ctggcacgac aggtttcccg actggaaagc gggcagtgag    300
cgcaacgcaa ttaatgtgag ttagctcact cattaggcac cccaggcttt acactttatg    360
ctcccggctc gtatgttgtg tggaattgtg agcggataac aatttcacac aggaaacagc    420
tatgaccatg attacgccaa gcttgcatgc aaattctatt tcaaggagac agtcatagct    480
agcatgaaaa agatttggct ggcgctggct ggtttagttt tagcgtttag cgcatcggcg    540
gactacaaag aggcccagcc ggccatggac ctgggtaaga aactgctgga agctgctcgt    600
gctggtcagg acgacgaagt tcgtatcctg atggctaacg gtgctgacgt taacgctcat    660
gacgaacagg gtactactcc gctgcacctg gctgctaaag aaggtcacct ggaaatcgtt    720
gaagttctgc tgaagtacgg tgctgacgtt aacgctcagg acaaattcgg taagaccgct    780
ttcgacatct ccatcgacaa cggtaacgag gacctggctg aaatcctgca gcggccgca    840 catcatcatc accatcacgg ggccgcagaa caaaaactca tctcagaaga ggatctgaat    900 ggccgcnta                                                            909

<210> SEQ ID NO 44
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (183)..(183)
<223> OTHER INFORMATION: Any amino acid

<400> SEQUENCE: 44

Met Leu Pro Ala Arg Met Leu Cys Gly Ile Val Ser Gly Gln Phe His
1               5                   10                  15

```
Thr Gly Asn Ser Tyr Asp His Asp Tyr Ala Lys Leu Ala Cys Lys Phe
             20                  25                  30

Tyr Phe Lys Glu Thr Val Ile Ala Ser Met Lys Lys Ile Trp Leu Ala
         35                  40                  45

Leu Ala Gly Leu Val Leu Ala Phe Ser Ala Ser Ala Asp Tyr Lys Glu
 50                  55                  60

Ala Gln Pro Ala Met Asp Leu Gly Lys Lys Leu Leu Glu Ala Ala Arg
 65                  70                  75                  80

Ala Gly Gln Asp Asp Glu Val Arg Ile Leu Met Ala Asn Gly Ala Asp
                 85                  90                  95

Val Asn Ala His Asp Glu Gln Gly Thr Thr Pro Leu His Leu Ala Ala
                100                 105                 110

Lys Glu Gly His Leu Glu Ile Val Glu Val Leu Leu Lys Tyr Gly Ala
            115                 120                 125

Asp Val Asn Ala Gln Asp Lys Phe Gly Lys Thr Ala Phe Asp Ile Ser
    130                 135                 140

Ile Asp Asn Gly Asn Glu Asp Leu Ala Glu Ile Leu Gln Ala Ala Ala
145                 150                 155                 160

His His His His His His Gly Ala Ala Glu Gln Lys Leu Ile Ser Glu
                165                 170                 175

Glu Asp Leu Asn Gly Arg Xaa
            180

<210> SEQ ID NO 45
<211> LENGTH: 930
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (12)..(17)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (64)..(64)
<223> OTHER INFORMATION: a, c, t, g, unknown or other
<220> FEATURE:
<221> NAME/KEY: modified_base
<222> LOCATION: (98)..(99)
<223> OTHER INFORMATION: a, c, t, g, unknown or other
<220> FEATURE:
<221> NAME/KEY: modified_base
<222> LOCATION: (101)..(101)
<223> OTHER INFORMATION: a, c, t, g, unknown or other
<220> FEATURE:
<221> NAME/KEY: modified_base
<222> LOCATION: (139)..(140)
<223> OTHER INFORMATION: a, c, t, g, unknown or other
<220> FEATURE:
<221> NAME/KEY: modified_base
<222> LOCATION: (898)..(898)
<223> OTHER INFORMATION: a, c, t, g, unknown or other
<220> FEATURE:
<221> NAME/KEY: modified_base
<222> LOCATION: (914)..(914)
<223> OTHER INFORMATION: a, c, t, g, unknown or other
<220> FEATURE:
<221> NAME/KEY: modified_base
<222> LOCATION: (918)..(922)
<223> OTHER INFORMATION: a, c, t, g, unknown or other
<220> FEATURE:
<221> NAME/KEY: modified_base
```

<222> LOCATION: (926)..(926)
<223> OTHER INFORMATION: a, c, t, g, unknown or other

<400> SEQUENCE: 45

```
gagctatgag annnnnncca cgcttccccn aagggagaaa ggcggacagg tatcccggta      60
agcnggcagg gtcggaacag gagagcgcac gagggagnnt ncagggggaa acgcctggta     120
tctttatagt cctgtcggnn tttcgccacc tctgacttga gcgtcgattt tttgtgatgc     180
tcgtcagggg ggcggagcct atggaaaaac gccagcaacg cggccttttt acggttcctg     240
gccttttgct ggccttttgc tcacatgttc tttcctgcgt tatcccctga ttctgtggat     300
aaccgtatta ccgcctttga gtgagctgat accgctcgcc gcagccgaac gaccgagcgc     360
agcgagtcag tgagcgagga agcggaagag cgcccaatac gcaaaccgcc tctccccgcg     420
cgttggccga ttcattaatg cagctggcac gacaggtttc ccgactggaa agcgggcagt     480
gagcgcaacg caattaatgt gagttagctc actcattagg caccccaggc tttacacttt     540
atgctcccgg ctcgtatgtt gtgtggaatt gtgagcggat aacaatttca cacaggaaac     600
agctatgacc atgattacgc caagcttgca tgcaaattct atttcaagga dacagtcata     660
gctagcatga aaaagatttg gctggcgctg gctggtttag ttttagcgtt tagcgcatcg     720
gcggactaca aagaggccca gccggccatg gtaggaagac ctgacgttaa cgctcaggac     780
aaattcggta agaccgcttt cgacatctcc atcgacaacg gtaacgagga cctggctgaa     840
atcctgcaag cggccgcaca tcatcatcac catcacgggg ccgcagaaca aaaactcntc     900
tcagaagagg atcngaannn nncgcntaga                                      930
```

<210> SEQ ID NO 46
<211> LENGTH: 211
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (207)..(207)
<223> OTHER INFORMATION: Any amino acid

<400> SEQUENCE: 46

```
Met Phe Phe Pro Ala Leu Ser Pro Asp Ser Val Asp Asn Arg Ile Thr
 1               5                  10                  15

Ala Phe Glu Ala Asp Thr Ala Arg Arg Ser Arg Thr Thr Glu Arg Ser
             20                  25                  30

Glu Ser Val Ser Glu Glu Ala Glu Glu Arg Pro Ile Arg Lys Pro Pro
         35                  40                  45

Leu Pro Ala Arg Trp Pro Ile His Cys Ser Trp His Asp Arg Phe Pro
     50                  55                  60

Asp Trp Lys Ala Gly Ser Glu Arg Asn Ala Ile Asn Val Ser Leu Thr
 65                  70                  75                  80

His Ala Pro Gln Ala Leu His Phe Met Leu Pro Ala Arg Met Leu Cys
                 85                  90                  95

Gly Ile Val Ser Gly Gln Phe His Thr Gly Asn Ser Tyr Asp His Asp
            100                 105                 110

Tyr Ala Lys Leu Ala Cys Lys Phe Tyr Phe Lys Glu Thr Val Ile Ala
        115                 120                 125

Ser Met Lys Lys Ile Trp Leu Ala Leu Ala Gly Leu Val Leu Ala Phe
    130                 135                 140
```

```
Ser Ala Ser Ala Asp Tyr Lys Glu Ala Gln Pro Ala Met Val Gly Arg
145                 150                 155                 160

Pro Asp Val Asn Ala Gln Asp Lys Phe Gly Lys Thr Ala Phe Asp Ile
            165                 170                 175

Ser Ile Asp Asn Gly Asn Glu Asp Leu Ala Glu Ile Leu Gln Ala Ala
        180                 185                 190

Ala His His His His His Gly Ala Ala Glu Gln Lys Leu Xaa Ser
        195                 200                 205

Glu Glu Asp
    210

<210> SEQ ID NO 47
<211> LENGTH: 915
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: modified_base
<222> LOCATION: (44)..(44)
<223> OTHER INFORMATION: a, c, t, g, unknown or other
<220> FEATURE:
<221> NAME/KEY: modified_base
<222> LOCATION: (46)..(46)
<223> OTHER INFORMATION: a, c, t, g, unknown or other
<220> FEATURE:
<221> NAME/KEY: modified_base
<222> LOCATION: (48)..(48)
<223> OTHER INFORMATION: a, c, t, g, unknown or other
<220> FEATURE:
<221> NAME/KEY: modified_base
<222> LOCATION: (58)..(61)
<223> OTHER INFORMATION: a, c, t, g, unknown or other
<220> FEATURE:
<221> NAME/KEY: modified_base
<222> LOCATION: (77)..(77)
<223> OTHER INFORMATION: a, c, t, g, unknown or other
<220> FEATURE:
<221> NAME/KEY: modified_base
<222> LOCATION: (104)..(105)
<223> OTHER INFORMATION: a, c, t, g, unknown or other
<220> FEATURE:
<221> NAME/KEY: modified_base
<222> LOCATION: (124)..(124)
<223> OTHER INFORMATION: a, c, t, g, unknown or other
<220> FEATURE:
<221> NAME/KEY: modified_base
<222> LOCATION: (141)..(141)
<223> OTHER INFORMATION: a, c, t, g, unknown or other
<220> FEATURE:
<221> NAME/KEY: modified_base
<222> LOCATION: (158)..(158)
<223> OTHER INFORMATION: a, c, t, g, unknown or other
<220> FEATURE:
<221> NAME/KEY: modified_base
<222> LOCATION: (901)..(902)
<223> OTHER INFORMATION: a, c, t, g, unknown or other
<220> FEATURE:
<221> NAME/KEY: modified_base
<222> LOCATION: (906)..(906)
<223> OTHER INFORMATION: a, c, t, g, unknown or other
```

```
<220> FEATURE:
<221> NAME/KEY: modified_base
<222> LOCATION: (908)..(910)
<223> OTHER INFORMATION: a, c, t, g, unknown or other

<400> SEQUENCE: 47
tcgtcagggg ggncggnagc ctatggaaaa acgnnagca acgngncttt tttacggnnn      60 ntggccttt gctggcnttt gctcacatgt tctttcctgc gttnncccct gattctgtgg     120
atanccgtat taccgccttt ngagtgagct gataccgntc gccgcagccg aacgaccgag    180
cgcagcgagt cagtgagcga ggaagcggaa gagcgcccaa tacgcaaacc gcctctcccc    240
gcgcgttggc cgattcatta atgcagctgg cacgacaggt ttcccgactg gaaagcgggc    300
agtgagcgca acgcaattaa tgtgagttag ctcactcatt aggcacccca ggctttacac    360
tttatgctcc cggctcgtat gttgtgtgga attgtgagcg gataacaatt tcacacagga    420
aacagctatg accatgatta cgccaagctt gcatgcaaat tctatttcaa ggagacagtc    480
atagctagca tgaaaaagat ttggctggcg ctggctggtt tagttttagc gtttagcgca    540
tcggcggact acaaagaggc ccagccggcc atggacctgg gtaagaaact gctggaagct    600
gctcgtgctg gtcaggacga cgaagttcgt atcctgatgg ctaacggtgc tgacgttaac    660
gcttgggaca tgactggtca tactccgctg cacctggctg ctcagttcgg tcacctggaa    720
atcgttgaag ttctgctgaa gcacggtgct gacgttaacg ctcaggacaa attcggtaag    780
accgctttcg acatctccat cgacaacggt aacgaggacc tggctgaaat cctgcaagcg    840
gccgcacatc atcatcacca tcacggggcc gcagaacaaa aactcatctc agaagaggat    900
nngaangnnn ccgca                                                     915

<210> SEQ ID NO 48
<211> LENGTH: 178
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Leu Pro Ala Arg Met Leu Cys Gly Ile Val Ser Gly Gln Phe His
1               5                   10                  15

Thr Gly Asn Ser Tyr Asp His Asp Tyr Ala Lys Leu Ala Cys Lys Phe
            20                  25                  30

Tyr Phe Lys Glu Thr Val Ile Ala Ser Met Lys Lys Ile Trp Leu Ala
        35                  40                  45

Leu Ala Gly Leu Val Leu Ala Phe Ser Ala Ser Ala Asp Tyr Lys Glu
    50                  55                  60

Ala Gln Pro Ala Met Asp Leu Gly Lys Lys Leu Leu Glu Ala Ala Arg
65                  70                  75                  80

Ala Gly Gln Asp Asp Glu Val Arg Ile Leu Met Ala Asn Gly Ala Asp
                85                  90                  95

Val Asn Ala Trp Asp Met Thr Gly His Thr Pro Leu His Leu Ala Ala
            100                 105                 110

Gln Phe Gly His Leu Glu Ile Val Glu Val Leu Leu Lys His Gly Ala
        115                 120                 125

Asp Val Asn Ala Gln Asp Lys Phe Gly Lys Thr Ala Phe Asp Ile Ser
    130                 135                 140

Ile Asp Asn Gly Asn Glu Asp Leu Ala Glu Ile Leu Gln Ala Ala Ala
145                 150                 155                 160
```

His His His His His His Gly Ala Ala Glu Gln Lys Leu Ile Ser Glu
                165                 170                 175

Glu Asp

<210> SEQ ID NO 49
<211> LENGTH: 848
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: modified_base
<222> LOCATION: (28)..(28)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (35)..(35)
<223> OTHER INFORMATION: a, c, t, g, unknown or other
<220> FEATURE:
<221> NAME/KEY: modified_base
<222> LOCATION: (41)..(41)
<223> OTHER INFORMATION: a, c, t, g, unknown or other
<220> FEATURE:
<221> NAME/KEY: modified_base
<222> LOCATION: (47)..(47)
<223> OTHER INFORMATION: a, c, t, g, unknown or other
<220> FEATURE:
<221> NAME/KEY: modified_base
<222> LOCATION: (51)..(54)
<223> OTHER INFORMATION: a, c, t, g, unknown or other
<220> FEATURE:
<221> NAME/KEY: modified_base
<222> LOCATION: (60)..(61)
<223> OTHER INFORMATION: a, c, t, g, unknown or other
<220> FEATURE:
<221> NAME/KEY: modified_base
<222> LOCATION: (89)..(89)
<223> OTHER INFORMATION: a, c, t, g, unknown or other
<220> FEATURE:
<221> NAME/KEY: modified_base
<222> LOCATION: (100)..(100)
<223> OTHER INFORMATION: a, c, t, g, unknown or other
<220> FEATURE:
<221> NAME/KEY: modified_base
<222> LOCATION: (102)..(102)
<223> OTHER INFORMATION: a, c, t, g, unknown or other
<220> FEATURE:
<221> NAME/KEY: modified_base
<222> LOCATION: (106)..(106)
<223> OTHER INFORMATION: a, c, t, g, unknown or other
<220> FEATURE:
<221> NAME/KEY: modified_base
<222> LOCATION: (108)..(108)
<223> OTHER INFORMATION: a, c, t, g, unknown or other
<220> FEATURE:
<221> NAME/KEY: modified_base
<222> LOCATION: (114)..(115)
<223> OTHER INFORMATION: a, c, t, g, unknown or other
<220> FEATURE:

```
<221> NAME/KEY: modified_base
<222> LOCATION: (118)..(118)
<223> OTHER INFORMATION: a, c, t, g, unknown or other
<220> FEATURE:
<221> NAME/KEY: modified_base
<222> LOCATION: (120)..(120)
<223> OTHER INFORMATION: a, c, t, g, unknown or other
<220> FEATURE:
<221> NAME/KEY: modified_base
<222> LOCATION: (152)..(152)
<223> OTHER INFORMATION: a, c, t, g, unknown or other
<220> FEATURE:
<221> NAME/KEY: modified_base
<222> LOCATION: (164)..(164)
<223> OTHER INFORMATION: a, c, t, g, unknown or other
<220> FEATURE:
<221> NAME/KEY: modified_base
<222> LOCATION: (170)..(170)
<223> OTHER INFORMATION: a, c, t, g, unknown or other
<220> FEATURE:
<221> NAME/KEY: modified_base
<222> LOCATION: (179)..(179)
<223> OTHER INFORMATION: a, c, t, g, unknown or other
<220> FEATURE:
<221> NAME/KEY: modified_base
<222> LOCATION: (221)..(222)
<223> OTHER INFORMATION: a, c, t, g, unknown or other
<220> FEATURE:
<221> NAME/KEY: modified_base
<222> LOCATION: (240)..(240)
<223> OTHER INFORMATION: a, c, t, g, unknown or other
<220> FEATURE:
<221> NAME/KEY: modified_base
<222> LOCATION: (292)..(292)
<223> OTHER INFORMATION: a, c, t, g, unknown or other
<220> FEATURE:
<221> NAME/KEY: modified_base
<222> LOCATION: (337)..(339)
<223> OTHER INFORMATION: a, c, t, g, unknown or other
<220> FEATURE:
<221> NAME/KEY: modified_base
<222> LOCATION: (480)..(480)
<223> OTHER INFORMATION: a, c, t, g, unknown or other
<220> FEATURE:
<221> NAME/KEY: modified_base
<222> LOCATION: (603)..(603)
<223> OTHER INFORMATION: a, c, t, g, unknown or other
<220> FEATURE:
<221> NAME/KEY: modified_base
<222> LOCATION: (645)..(645)
<223> OTHER INFORMATION: a, c, t, g, unknown or other
<220> FEATURE:
<221> NAME/KEY: modified_base
<222> LOCATION: (707)..(707)
<223> OTHER INFORMATION: a, c, t, g, unknown or other
<220> FEATURE:
<221> NAME/KEY: modified_base
<222> LOCATION: (719)..(719)
<223> OTHER INFORMATION: a, c, t, g, unknown or other
<220> FEATURE:
<221> NAME/KEY: modified_base
<222> LOCATION: (753)..(753)
<223> OTHER INFORMATION: a, c, t, g, unknown or other

<400> SEQUENCE: 49
tttatagtnc ntgtcgggtt tcnccacntn tgacntgagc ntcgatnttt nnnntgctcn      60 ncagggggc ggagcctatg gaaaaacgnc agcaacgcgn cntttntncg gttnntgncn      120
ttttgctggc cttttgctca catgttcttt cntgcgttat cccntgattn tgtggatanc     180
cgtattaccg cctttgagtg agctgatacc gctcgccgca nncgaacgac cgagcgcagn    240
gagtcagtga gcgaggaagc ggaagagcgc ccaatacgca aaccgcctct cnccgcgcgt    300
tggccgattc attaatgcag ctggcacgac aggtttnnng actggaaagc gggcagtgag    360
cgcaacgcaa ttaatgtgag ttagctcact cattaggcac cccaggcttt acactttatg    420
```

```
ctcccggctc gtatgttgtg tggaattgtg agcggataac aatttcacac aggaaacagn    480
tatgaccatg attacgccaa gcttgcatgc aaattctatt tcaaggagac agtcatagct    540
agcatgaaaa agatttggct ggcgctggct ggtttagttt tagcgtttag cgcatcggcg    600
gantacaaag aggcccagcc ggccatgggc ggaaccagca gtttnttacc caggtccatg    660
gacctgggtc acctggaaat cgttgaagtt ctgctgaagt acggtgntga cgttaacgnt    720
caggacaaat tcggtaagac cgctttcgac atntccatcg acaacggtaa cgaggacctg    780
gctgaaatcc tgcaagcggc cgcacatcat catcaccatc atcgggctcg cagaacaaaa    840
atcatctc                                                             848
```

```
<210> SEQ ID NO 50
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (10)..(10)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (26)..(26)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (50)..(50)
<223> OTHER INFORMATION: Any amino acid
<220> FEATURE:
<221> NAME/KEY: MOD_RES
<222> LOCATION: (64)..(64)
<223> OTHER INFORMATION: Any amino acid
<220> FEATURE:
<221> NAME/KEY: MOD_RES
<222> LOCATION: (108)..(108)
<223> OTHER INFORMATION: Any amino acid
<220> FEATURE:
<221> NAME/KEY: MOD_RES
<222> LOCATION: (149)..(149)
<223> OTHER INFORMATION: Any amino acid
<220> FEATURE:
<221> NAME/KEY: MOD_RES
<222> LOCATION: (163)..(163)
<223> OTHER INFORMATION: Any amino acid
<220> FEATURE:
<221> NAME/KEY: MOD_RES
<222> LOCATION: (184)..(184)
<223> OTHER INFORMATION: Any amino acid
<220> FEATURE:
<221> NAME/KEY: MOD_RES
<222> LOCATION: (188)..(188)
<223> OTHER INFORMATION: Any amino acid
<220> FEATURE:
<221> NAME/KEY: MOD_RES
```

<222> LOCATION: (199)..(199)
<223> OTHER INFORMATION: Any amino acid

<400> SEQUENCE: 50

Met Phe Phe Xaa Ala Leu Ser Xaa Asp Xaa Val Asp Xaa Arg Ile Thr
1               5                   10                  15

Ala Phe Glu Ala Asp Thr Ala Arg Arg Xaa Arg Thr Thr Glu Arg Xaa
            20                  25                  30

Glu Ser Val Ser Glu Glu Ala Glu Arg Pro Ile Arg Lys Pro Pro
        35                  40                  45

Leu Xaa Ala Arg Trp Pro Ile His Cys Ser Trp His Asp Arg Phe Xaa
    50                  55                  60

Asp Trp Lys Ala Gly Ser Glu Arg Asn Ala Ile Asn Val Ser Leu Thr
65                  70                  75                  80

His Ala Pro Gln Ala Leu His Phe Met Leu Pro Ala Arg Met Leu Cys
                85                  90                  95

Gly Ile Val Ser Gly Gln Phe His Thr Gly Asn Xaa Tyr Asp His Asp
            100                 105                 110

Tyr Ala Lys Leu Ala Cys Lys Phe Tyr Phe Lys Glu Thr Val Ile Ala
        115                 120                 125

Ser Met Lys Lys Ile Trp Leu Ala Leu Ala Gly Leu Val Leu Ala Phe
130                 135                 140

Ser Ala Ser Ala Xaa Tyr Lys Glu Ala Gln Pro Ala Met Gly Gly Thr
145                 150                 155                 160

Ser Ser Xaa Leu Pro Arg Ser Met Asp Leu Gly His Leu Glu Ile Val
            165                 170                 175

Glu Val Leu Leu Lys Tyr Gly Xaa Asp Val Asn Xaa Gln Asp Lys Phe
        180                 185                 190

Gly Lys Thr Ala Phe Asp Xaa Ser Ile Asp Asn Gly Asn Glu Asp Leu
    195                 200                 205

Ala Glu Ile Leu Gln Ala Ala Ala His His His His His His Arg Ala
210                 215                 220

Arg Arg Thr Lys Ile Ile
225                 230

<210> SEQ ID NO 51
<211> LENGTH: 900
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (33)..(33)
<223> OTHER INFORMATION: a, c, t, g, unknown or other
<220> FEATURE:
<221> NAME/KEY: modified_base
<222> LOCATION: (59)..(59)
<223> OTHER INFORMATION: a, c, t, g, unknown or other
<220> FEATURE:
<221> NAME/KEY: modified_base
<222> LOCATION: (61)..(61)
<223> OTHER INFORMATION: a, c, t, g, unknown or other
<220> FEATURE:
<221> NAME/KEY: modified_base
<222> LOCATION: (63)..(63)
<223> OTHER INFORMATION: a, c, t, g, unknown or other
<220> FEATURE:
<221> NAME/KEY: modified_base
<222> LOCATION: (69)..(69)
<223> OTHER INFORMATION: a, c, t, g, unknown or other
<220> FEATURE:

```
<221> NAME/KEY: modified_base
<222> LOCATION: (133)..(136)
<223> OTHER INFORMATION: a, c, t, g, unknown or other
<220> FEATURE:
<221> NAME/KEY: modified_base
<222> LOCATION: (833)..(838)
<223> OTHER INFORMATION: a, c, t, g, unknown or other
<220> FEATURE:
<221> NAME/KEY: modified_base
<222> LOCATION: (872)..(874)
<223> OTHER INFORMATION: a, c, t, g, unknown or other
<220> FEATURE:
<221> NAME/KEY: modified_base
<222> LOCATION: (886)..(887)
<223> OTHER INFORMATION: a, c, t, g, unknown or other
<220> FEATURE:
<221> NAME/KEY: modified_base
<222> LOCATION: (891)..(894)
<223> OTHER INFORMATION: a, c, t, g, unknown or other

<400> SEQUENCE: 51
gagcctatgg aaaaaacgcc cagcaacgcg gcnttttac ggttcctggc cttttgctng      60
ncntttgnt cacatgttct ttcctgcgtt atccctgat tctgtggata accgtattac     120
cgcctttgag tgnnnngata ccgctcgccg cagccgaacg accgagcgca gcgagtcagt   180
gagcgaggaa gcggaagagc gcccaatacg caaaccgcct ctccccgcgc gttggccgat   240
tcattaatgc agctggcacg acaggtttcc cgactggaaa gcgggcagtg agcgcaacgc   300
aattaatgtg agttagctca ctcattaggc accccaggct ttacacttta tgctcccggc   360
tcgtatgttg tgtggaattg tgagcggata acaatttcac acaggaaaca gctatgacca   420
tgattacgcc aagcttgcat gcaaattcta tttcaaggag acagtcatag ctagcatgaa   480
aaagatttgg ctggcgctgg ctggtttagt tttagcgttt agcgcatcgg cggactacaa   540
agaggcccag ccggccatgg acctgggtaa gaaactgctg gaagctgctc gtgctggtca   600
ggacgacgaa gttcgtatcc tgatggctaa cggtgctgac gttaacgctg acgacttctc   660
tggtactact ccgctgcacc tggctgctca tcatggtcac ctggaaatcg ttgaagttct   720
gctgaagtac ggtgctgacg ttaacgctca ggacaaattc ggtaagaccg ctttcgacat   780
ctccatcgac aacggtaacg aggacctggc tgaaatcctg caagcggccg cannnnnnca   840
tcaccatcac ggggccgcag aacaaaaact cnnncagaag aggatnngaa nnncgcata    900
```

```
<210> SEQ ID NO 52
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(21)
<223> OTHER INFORMATION: Any amino acid
<220> FEATURE:
<221> NAME/KEY: MOD_RES
<222> LOCATION: (250)..(251)
<223> OTHER INFORMATION: Any amino acid
<220> FEATURE:
<221> NAME/KEY: MOD_RES
<222> LOCATION: (263)..(263)
<223> OTHER INFORMATION: Any amino acid

<400> SEQUENCE: 52

Met Phe Phe Pro Ala Leu Ser Pro Asp Ser Val Asp Asn Arg Ile Thr
1               5                   10                  15

Ala Phe Glu Xaa Xaa Asp Thr Ala Arg Arg Ser Arg Thr Thr Glu Arg
```

```
                20                  25                  30
Ser Glu Ser Val Ser Glu Glu Ala Glu Arg Pro Ile Arg Lys Pro
                35                  40                  45

Pro Leu Pro Ala Arg Trp Pro Ile His Cys Ser Trp His Asp Arg Phe
 50                  55                  60

Pro Asp Trp Lys Ala Gly Ser Glu Arg Asn Ala Ile Asn Val Ser Leu
 65                  70                  75                  80

Thr His Ala Pro Gln Ala Leu His Phe Met Leu Pro Ala Arg Met Leu
                85                  90                  95

Cys Gly Ile Val Ser Gly Gln Phe His Thr Gly Asn Ser Tyr Asp His
                100                 105                 110

Asp Tyr Ala Lys Leu Ala Cys Lys Phe Tyr Phe Lys Glu Thr Val Ile
                115                 120                 125

Ala Ser Met Lys Lys Ile Trp Leu Ala Leu Ala Gly Leu Val Leu Ala
                130                 135                 140

Phe Ser Ala Ser Ala Asp Tyr Lys Glu Ala Gln Pro Ala Met Asp Leu
145                 150                 155                 160

Gly Lys Lys Leu Leu Glu Ala Ala Arg Ala Gly Gln Asp Asp Glu Val
                165                 170                 175

Arg Ile Leu Met Ala Asn Gly Ala Asp Val Asn Ala Asp Asp Phe Ser
                180                 185                 190

Gly Thr Thr Pro Leu His Leu Ala Ala His His Gly His Leu Glu Ile
                195                 200                 205

Val Glu Val Leu Leu Lys Tyr Gly Ala Asp Val Asn Ala Gln Asp Lys
                210                 215                 220

Phe Gly Lys Thr Ala Phe Asp Ile Ser Ile Asp Asn Gly Asn Glu Asp
225                 230                 235                 240

Leu Ala Glu Ile Leu Gln Ala Ala Xaa Xaa His His His His Gly
                245                 250                 255

Ala Ala Glu Gln Lys Leu Xaa
                260

<210> SEQ ID NO 53
<211> LENGTH: 919
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (8)..(9)
<223> OTHER INFORMATION: a, c, t, g, unknown or other
<220> FEATURE:
<221> NAME/KEY: modified_base
<222> LOCATION: (29)..(29)
<223> OTHER INFORMATION: a, c, t, g, unknown or other
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: modified_base
<222> LOCATION: (130)..(130)
<223> OTHER INFORMATION: a, c, t, g, unknown or other
```

<220> FEATURE:
<221> NAME/KEY: modified_base
<222> LOCATION: (910)..(912)
<223> OTHER INFORMATION: a, c, t, g, unknown or other
<220> FEATURE:
<221> NAME/KEY: modified_base
<222> LOCATION: (916)..(916)
<223> OTHER INFORMATION: a, c, t, g, unknown or other

<400> SEQUENCE: 53

```
gangntcnnc agggggggcg gagcctatng aaaaaacgcc agcaacgcgg cnttttttac    60
ggttcctggc cttttgctgg ccttttgctc acatgttctt tcctgcgtta tccctgatt    120
ctgtggatan ccgtattacc gcctttgagt gagctgatac cgctcgccgc agccgaacga   180
ccgagcgcag cgagtcagtg agcgaggaag cggaagagcg cccaatacgc aaaccgcctc   240
tccccgcgcg ttggccgatt cattaatgca gctggcacga caggtttccc gactggaaag   300
cgggcagtga gcgcaacgca attaatgtga gttagctcac tcattaggca ccccaggctt   360
tacactttat gctcccggct cgtatgttgt gtggaattgt gagcggataa caatttcaca   420
caggaaacag ctatgaccat gattacgcca agcttgcatg caaattctat ttcaaggaga   480
cagtcatagc tagcatgaaa aagatttggc tggcgctggc tggtttagtt ttagcgttta   540
gcgcatcggc ggactacaaa gaggcccagc cggccatgga cctgggtaag aaactgctgg   600
aagctgctcg tgctggtcag gacgacgaag ttcgtatcct gatggctaac ggtgctgacg   660
ttaacgctct ggacgaagtt ggttctactc cgctgcacct ggctgctatg gctggtcacc   720
tggaaatcgt tgaagtgctg aagcacggtg ctgacgttaa cgctcaggac aaattcggta   780
agaccgcttt cgacatctcc atcgacaacg gtaacgagga cctggctgaa atcctgcaag   840
cggccgcaca tcatcatcac catcacgggg ccgcagaaca aaaactcatc tcagaagagg   900
atctgaatgn nncgcntag                                                919
```

<210> SEQ ID NO 54
<211> LENGTH: 177
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

```
Met Leu Pro Ala Arg Met Leu Cys Gly Ile Val Ser Gly Gln Phe His
1               5                   10                  15
Thr Gly Asn Ser Tyr Asp His Asp Tyr Ala Lys Leu Ala Cys Lys Phe
            20                  25                  30
Tyr Phe Lys Glu Thr Val Ile Ala Ser Met Lys Lys Ile Trp Leu Ala
        35                  40                  45
Leu Ala Gly Leu Val Leu Ala Phe Ser Ala Ser Ala Asp Tyr Lys Glu
    50                  55                  60
Ala Gln Pro Ala Met Asp Leu Gly Lys Lys Leu Leu Glu Ala Ala Arg
65                  70                  75                  80
Ala Gly Gln Asp Asp Glu Val Arg Ile Leu Met Ala Asn Gly Ala Asp
                85                  90                  95
Val Asn Ala Leu Asp Glu Val Gly Ser Thr Pro Leu His Leu Ala Ala
            100                 105                 110
Met Ala Gly His Leu Glu Ile Val Glu Val Leu Lys His Gly Ala Asp
        115                 120                 125
Val Asn Ala Gln Asp Lys Phe Gly Lys Thr Ala Phe Asp Ile Ser Ile
```

| | | | | | | | | | |
|---|---|---|---|---|---|---|---|---|---|
| | | 130 | | | 135 | | | 140 | |

Asp Asn Gly Asn Glu Asp Leu Ala Glu Ile Leu Gln Ala Ala Ala His
145 150 155 160

His His His His His Gly Ala Ala Glu Gln Lys Leu Ile Ser Glu Glu
165 170 175

Asp

<210> SEQ ID NO 55
<211> LENGTH: 934
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (34)..(34)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: modified_base
<222> LOCATION: (58)..(59)
<223> OTHER INFORMATION: a, c, t, g, unknown or other
<220> FEATURE:
<221> NAME/KEY: modified_base
<222> LOCATION: (97)..(97)
<223> OTHER INFORMATION: a, c, t, g, unknown or other
<220> FEATURE:
<221> NAME/KEY: modified_base
<222> LOCATION: (923)..(927)
<223> OTHER INFORMATION: a, c, t, g, unknown or other
<220> FEATURE:
<221> NAME/KEY: modified_base
<222> LOCATION: (931)..(931)
<223> OTHER INFORMATION: a, c, t, g, unknown or other

<400> SEQUENCE: 55

| | |
|---|---|
| ggacaggnta tccggtaaag cggcagggtc ggancannag agcgcacgag ggagcttnnc | 60 |
| aggggggaaac gcctggtatc tttatagtcc tgtcggnttt cgcccacctc tgacttgagc | 120 |
| gtcgattttt gtgatgctcg tcagggggg cggagcctat ggaaaaacgc cagcaacgcg | 180 |
| gccttttac ggttcctggc cttttgctgg ccttttgctc acatgttctt tcctgcgtta | 240 |
| tcccctgatt ctgtggataa ccgtattacc gcctttgagt gagctgatac cgctcgccgc | 300 |
| agccgaacga ccgagcgcag cgagtcagtg agcgaggaag cggaagagcg cccaatacgc | 360 |
| aaaccgcctc tccccgcgcg ttggccgatt cattaatgca gctggcacga caggtttccc | 420 |
| gactggaaag cgggcagtga gcgcaacgca attaatgtga gttagctcac tcattaggca | 480 |
| ccccaggctt tacactttat gctcccggct cgtatgttgt gtggaattgt gagcggataa | 540 |
| caatttcaca caggaaacag ctatgaccat gattacgcca agcttgcatg caaattctat | 600 |
| ttcaaggaga cagtcatagc tagcatgaaa aagatttggc tggcgctggc tggtttagtt | 660 |
| ttagcgttta gcgcatcggc ggactacaaa gaggcccagc cggccatgga cctggctgct | 720 |
| catgttggtc acctggaaat cgttgaagtt ctgctgaagt acggtgctga cgttaacgct | 780 |
| caggacaaat tcggtaagac cgcttttcgac atctccatcg acaacggtaa cgaggacctg | 840 |
| gctgaaatcc tgcaagcggc cgcacatcat catcaccatc acgggccgc agaacaaaaa | 900 | ctcatctcag aagaggatct gannnnncgc ntag                                                    934

<210> SEQ ID NO 56
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Phe Phe Pro Ala Leu Ser Pro Asp Ser Val Asp Asn Arg Ile Thr
1               5                   10                  15

Ala Phe Glu Ala Asp Thr Ala Arg Arg Ser Arg Thr Thr Glu Arg Ser
            20                  25                  30

Glu Ser Val Ser Glu Glu Ala Glu Arg Pro Ile Arg Lys Pro Pro
        35                  40                  45

Leu Pro Ala Arg Trp Pro Ile His Cys Ser Trp His Asp Arg Phe Pro
    50                  55                  60

Asp Trp Lys Ala Gly Ser Glu Arg Asn Ala Ile Asn Val Ser Leu Thr
65                  70                  75                  80

His Ala Pro Gln Ala Leu His Phe Met Leu Pro Ala Arg Met Leu Cys
                85                  90                  95

Gly Ile Val Ser Gly Gln Phe His Thr Gly Asn Ser Tyr Asp His Asp
            100                 105                 110

Tyr Ala Lys Leu Ala Cys Lys Phe Tyr Phe Lys Glu Thr Val Ile Ala
        115                 120                 125

Ser Met Lys Lys Ile Trp Leu Ala Leu Ala Gly Leu Val Leu Ala Phe
130                 135                 140

Ser Ala Ser Ala Asp Tyr Lys Glu Ala Gln Pro Ala Met Asp Leu Ala
145                 150                 155                 160

Ala His Val Gly His Leu Glu Ile Val Glu Val Leu Leu Lys Tyr Gly
                165                 170                 175

Ala Asp Val Asn Ala Gln Asp Lys Phe Gly Lys Thr Ala Phe Asp Ile
            180                 185                 190

Ser Ile Asp Asn Gly Asn Glu Asp Leu Ala Glu Ile Leu Gln Ala Ala
        195                 200                 205

Ala His His His His His His Gly Ala Ala Glu Gln Lys Leu Ile Ser
    210                 215                 220

Glu Glu Asp Leu
225

<210> SEQ ID NO 57
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(100)
<223> OTHER INFORMATION: This region may encompass 3-100 residues
<220> FEATURE:
<221> NAME/KEY: MISC_FEATURE
<222> LOCATION: (102)..(201)
<223> OTHER INFORMATION: This region may encompass 3-100 residues

<400> SEQUENCE: 57

Gly Gly Gly Gly Gly Gly Gly Gly Gly Gly Gly Gly Gly Gly Gly Gly
1               5                   10                  15

-continued

```
Gly Gly Gly Gly Gly Gly Gly Gly Gly Gly Gly Gly Gly Gly Gly
            20                  25                  30
Gly Gly Gly Gly Gly Gly Gly Gly Gly Gly Gly Gly Gly Gly Gly
            35                  40                  45
Gly Gly Gly Gly Gly Gly Gly Gly Gly Gly Gly Gly Gly Gly Gly
50                  55                  60
Gly Gly Gly Gly Gly Gly Gly Gly Gly Gly Gly Gly Gly Gly Gly
65                  70                  75                  80
Gly Gly Gly Gly Gly Gly Gly Gly Gly Gly Gly Gly Gly Gly Gly
            85                  90                  95
Gly Gly Gly Gly Pro Gly Gly Gly Gly Gly Gly Gly Gly Gly Gly
            100                 105                 110
Gly Gly Gly Gly Gly Gly Gly Gly Gly Gly Gly Gly Gly Gly Gly
            115                 120                 125
Gly Gly Gly Gly Gly Gly Gly Gly Gly Gly Gly Gly Gly Gly Gly
            130                 135                 140
Gly Gly Gly Gly Gly Gly Gly Gly Gly Gly Gly Gly Gly Gly Gly
145                 150                 155                 160
Gly Gly Gly Gly Gly Gly Gly Gly Gly Gly Gly Gly Gly Gly Gly
            165                 170                 175
Gly Gly Gly Gly Gly Gly Gly Gly Gly Gly Gly Gly Gly Gly Gly
            180                 185                 190
Gly Gly Gly Gly Gly Gly Gly Gly Gly
            195                 200
```